US012624047B2

(12) United States Patent
Ran et al.

(10) Patent No.: US 12,624,047 B2
(45) Date of Patent: May 12, 2026

(54) ORGANIC COMPOUND AND APPLICATION THEREOF

(71) Applicants: Wuhan Tianma Microelectronics Co., Ltd., Wuhan (CN); Wuhan Tianma Microelectronics Co., Ltd. Shanghai Branch, Shanghai (CN)

(72) Inventors: Quan Ran, Wuhan (CN); Xinyuan Zheng, Wuhan (CN); Mingzhi Dai, Wuhan (CN); Yuhao Liu, Wuhan (CN); Shuang Cheng, Wuhan (CN); Ji Nan, Wuhan (CN); Xiaolei Pang, Wuhan (CN); Qingsong Yuan, Wuhan (CN)

(73) Assignees: Wuhan Tianma Microelectronics Co., Ltd., Wuhan (CN); Wuhan Tianma Microelectronics Co., Ltd, Shanghai Branch, Shanghai (CN)

(*) Notice: Subject to any disclaimer, the term of this patent is extended or adjusted under 35 U.S.C. 154(b) by 1034 days.

(21) Appl. No.: 17/675,959

(22) Filed: Feb. 18, 2022

(65) Prior Publication Data

US 2022/0169657 A1 Jun. 2, 2022

(30) Foreign Application Priority Data

Nov. 26, 2021 (CN) ......................... 202111423743.6

(51) Int. Cl.
*C07D 493/00* (2006.01)
*C07D 519/00* (2006.01)
(Continued)

(52) U.S. Cl.
CPC ......... *C07D 493/00* (2013.01); *C07D 519/00* (2013.01); *H10K 85/615* (2023.02); *H10K 85/654* (2023.02); *H10K 85/6574* (2023.02); *H10K 85/6576* (2023.02); *H10K 50/16* (2023.02); *H10K 50/18* (2023.02)

(58) Field of Classification Search
None
See application file for complete search history.

(56) References Cited

U.S. PATENT DOCUMENTS

2002/0121860 A1* 9/2002 Seo ............................... 313/506
2009/0015140 A1* 1/2009 Kawakami .................... 313/504
(Continued)

FOREIGN PATENT DOCUMENTS

CN 103153974 A 6/2013

*Primary Examiner* — Seokmin Jeon
(74) *Attorney, Agent, or Firm* — KDW FIRM PLLC

(57) ABSTRACT

Provided are an organic compound and an application thereof. The compound has a relatively deep LUMO energy level, which may reduce a potential barrier of electron transport, improve an electron injection capability and effectively reduce a voltage of an OLED device. The compounds each have a relatively deep HOMO energy level, which may effectively block holes so that more holes and electrons are recombined in a light-emitting region, achieving relatively high luminescence efficiency. An electron transport layer material and/or a hole blocking layer material suitable for the OLED device can reduce the voltage and power consumption of the device, improve the luminescence efficiency and extend a working lifetime so that the OLED device has better comprehensive performance.

15 Claims, 1 Drawing Sheet

(51) Int. Cl.

| | |
|---|---|
| ***H10K 50/16*** | (2023.01) |
| ***H10K 50/18*** | (2023.01) |
| ***H10K 85/60*** | (2023.01) |

(56) References Cited

U.S. PATENT DOCUMENTS

| | | | | |
|---|---|---|---|---|
| 2012/0095222 | A1* | 4/2012 | Schaefer | 544/216 |
| 2016/0072072 | A1 | 3/2016 | Kim et al. | |
| 2020/0203632 | A1 | 6/2020 | Yen et al. | |

* cited by examiner

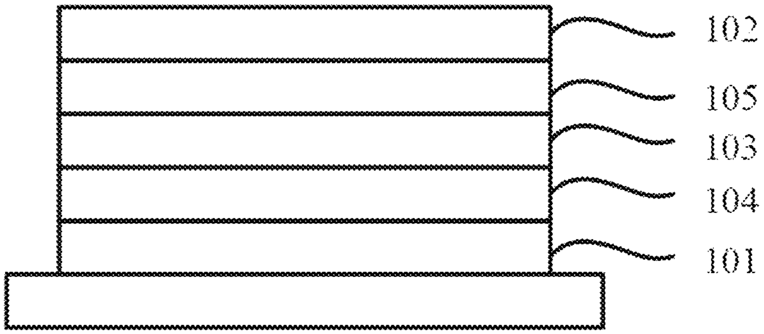
102
105
103
104
101

ORGANIC COMPOUND AND APPLICATION THEREOF

CROSS-REFERENCE TO RELATED APPLICATION(S)

This application claims priority to Chinese Patent Application No. CN 202111423743.6 filed Nov. 26, 2021, the disclosure of which is incorporated herein by reference in its entirety.

TECHNICAL FIELD

The present disclosure belongs to the technical field of organic electroluminescent materials and, in particular, to an organic compound and an application thereof.

BACKGROUND

An electron transport material used in a conventional electroluminescent device is Alq3. However, Alq3 has a relatively low electron mobility (of about $10^{-6}$ $cm^2/Vs$), such that Alq3 cannot achieve a balance between electron transport and hole transport in the device. With the commercialization and practical application of electroluminescent devices, it is desired to obtain an ETL material with higher transport efficiency and better performance. In this field, researchers have made a large amount of exploratory work.

WO 2007/011170 A1 and CN 101003508A of LG Chem disclose a series of derivatives of naphthoimidazole and pyrene, respectively, which are used as electron transport and injection materials in an electroluminescent device and improve luminescence efficiency of the device.

In Publication Nos. US 2006/0204784 and US 2007/0048545, Eastman Kodak Company discloses an organic electroluminescent device using a hybrid electron transport material obtained by doping the following materials: (a) a first compound having a lowest LUMO energy level in the layer, (b) a second compound having a higher LUMO energy level than the first compound and a low turn-on voltage, and a metal material having a work function of less than 4.2 eV. However, the above electron transport material has a planar molecular structure and a large intermolecular attractive force, which are not conducive to evaporation and application. Further, the electron transport material has the disadvantages of relatively low mobility, poor energy level matching, poor thermal stability, a short lifetime, doping and the like, which limit the further development of OLED display devices.

Therefore, to design and develop stable and efficient electron transport materials and/or electron injection materials that can have both high electron mobility and a high glass transition temperature and be effectively doped with a metal Yb or Liq has very important practical application value in reducing a threshold voltage, improving device efficiency and extending the lifetime of the device.

In the market, commonly used electron transport materials such as batho-phenanthroline (BPhen), bathocuproine (BCP) and TmPyPB can generally meet market requirements for an organic electroluminescent panel. However, they have a relatively low glass transition temperature which is generally less than 85° C. When the device is working, generated Joule heat causes molecular degradation and a change in molecular structure, resulting in relatively low panel efficiency and relatively poor thermal stability. Moreover, the molecular structure has a very regular symmetry and is easy to crystallize after a long time. Once the electron transport material crystallizes, an intermolecular charge transition mechanism differs from the mechanism of the normally working amorphous film, resulting in poorer performance of the electron transport, an imbalance between electron mobility and hole mobility of the entire device and significantly reduced formation efficiency of excitons. Further, the formed excitons are concentrated at an interface between an electron transport layer and a light-emitting layer, resulting in significantly reduced device efficiency and a significantly shortened lifetime.

Therefore, it is urgent to develop electron transport material with more types and better performance in the art to meet application requirements of the OLED display devices.

SUMMARY

In view of the deficiencies in the related art, an object of the present disclosure is to provide an organic compound and an application thereof.

To achieve this object, the present disclosure adopts technical solutions described below.

A first aspect of the present disclosure is to provide an organic compound having a structure represented by Formula I:

Formula I

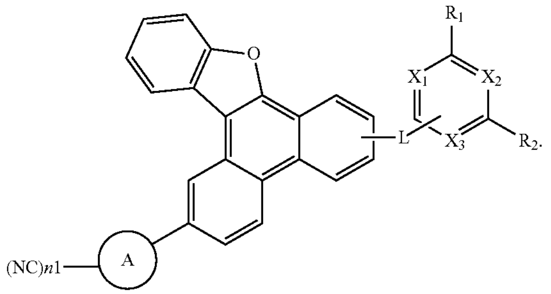

The ring A is selected from a substituted or unsubstituted C6-C30 aryl ring or a substituted or unsubstituted C5-C30 heteroaryl ring.

L is selected from a single bond, substituted or unsubstituted C6-C30 aryl or substituted or unsubstituted C5-C30 heteroaryl.

$X_1$ to $X_3$ are independently selected from a C atom or a N atom, and at least one of $X_1$ to $X_3$ is N.

$R_1$ and $R_2$ are independently selected from substituted or unsubstituted C6-C30 aryl or substituted or unsubstituted C5-C30 heteroaryl.

$n_1$ is an integer from 0 to 3.

In the present disclosure, C5-C30 may each independently be C6, C7, C8, C9, C10, C12, C13, C14, C15, C16, C18, C20, C22, C24, C26, C28, C29 or the like.

C6-C30 may each independently be C7, C8, C9, C10, C12, C13, C14, C15, C16, C18, C20, C22, C24, C26, C28, C29 or the like.

The organic compound provided by the present disclosure contains both

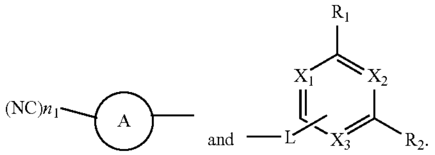

A skeletal structure and a substituent cooperate with each other so that the compound has a relatively deep LUMO energy level, which is conducive to reducing a potential barrier of electron injection, improving an electron injection capability and effectively reducing a voltage of an OLED device. The HOMO energy level and LUMO energy level of the compound are suitable, which are conducive to matching energy levels in adjacent layers. The HOMO energy level is relatively deep so that the compound has a hole-blocking capability and more holes and electrons are recombined in a light-emitting region, achieving relatively high luminescence efficiency.

A second aspect of the present disclosure is to provide an electron transport layer material. The electron transport layer material includes the organic compound according to the first aspect.

A third aspect of the present disclosure is to provide a hole blocking layer material. The hole blocking layer material includes the organic compound according to the first aspect.

A fourth aspect of the present disclosure is to provide an OLED device. The OLED device includes an anode, a cathode and an organic thin film disposed between the anode and the cathode, where a material of the organic thin film includes at least one of the organic compounds each according to the first aspect.

A fifth aspect of the present disclosure is to provide a display panel. The display panel includes the OLED device according to the fourth aspect.

A sixth aspect of the present disclosure is to provide an electronic device. The electronic device includes the display panel according to the fifth aspect.

BRIEF DESCRIPTION OF DRAWINGS

The FIGURE is a structure diagram of an OLED device provided in the present disclosure.

REFERENCE LIST

101 anode
102 cathode
103 light-emitting layer
104 first organic thin film
105 second organic thin film

DETAILED DESCRIPTION

Technical solutions of the present disclosure are further described below through the detailed description. Those skilled in the art are to understand that the embodiments are merely used for understanding the present disclosure and are not to be construed as specific limitations to the present disclosure.

A first aspect of the present disclosure is to provide an organic compound having a structure represented by Formula I:

Formula I

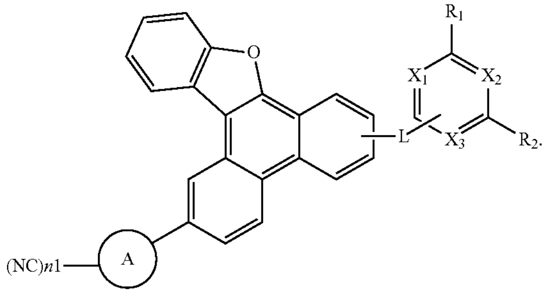

The ring A is selected from substituted or unsubstituted C6-C30 aryl, or substituted or unsubstituted C5-C30 heteroaryl.

L is selected from a single bond, substituted or unsubstituted C6-C30 aryl, or substituted or unsubstituted C5-C30 heteroaryl.

$X_1$ to $X_3$ are independently selected from a C atom or a N atom, and at least one of $X_1$ to $X_3$ is N.

$R_1$ and $R_2$ are independently selected from substituted or unsubstituted C6-C30 aryl or substituted or unsubstituted C5-C30 heteroaryl.

$n_1$ is an integer from 0 to 3 (for example, 0, 1, 2 or 3).

In the present disclosure, C5-C30 may each independently be C6, C7, C8, C9, C10, C12, C13, C14, C15, C16, C18, C20, C22, C24, C26, C28, C29 or the like.

C6-C30 may each independently be C7, C8, C9, C10, C12, C13, C14, C15, C16, C18, C20, C22, C24, C26, C28, C29 or the like.

The organic compound provided by the present disclosure contains both

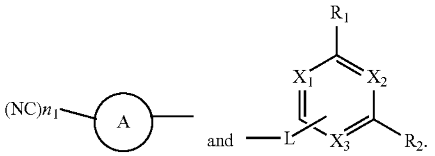

A skeletal structure and a substituent cooperate with each other so that the compound has a relatively deep LUMO energy level, which is conducive to reducing a potential barrier of electron injection, improving an electron injection capability and effectively reducing a voltage of an OLED device. The HOMO energy level and LUMO energy level of the compound are suitable, which are conducive to matching energy levels in adjacent layers. The HOMO energy level is relatively deep so that the compound has a hole-blocking capability and more holes and electrons are recombined in a light-emitting region, achieving relatively high luminescence efficiency. The compound material has a relatively high glass transition temperature $T_g$ and good thermal stability so that the material shows a form of an amorphous thin film when deposited by means of evaporation, thereby avoiding an effect of Joule heat generated by the device in operation on the lifetime and efficiency of the device.

In an embodiment, the organic compound has a structure represented by Formula II:

Formula II

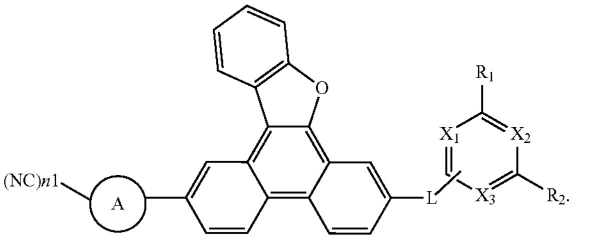

In the present disclosure, the connection manner shown in Formula II is preferred. Benzophenanthrofuran at the center,

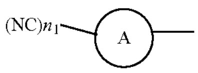

and

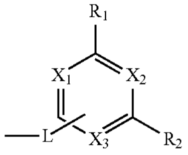

have better planarity, are more conducive to the electron transport and may be more matched with the mobility of a hole transport layer, which is conducive to improving a charge balance and achieving relatively high luminescence efficiency. Moreover, two sides of benzophenanthrofuran at the center are in symmetrical positions, which is more conducive to obtaining a raw material and the subsequent synthesis and conducive to mass production.

In an embodiment, when substituted or unsubstituted C6-C30 aryl, or substituted or unsubstituted C5-C30 heteroaryl contains a substituent, the substituent is selected from at least one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C9, C10, C12, C14, C16, C18 or the like) aryl, C5-C20 (for example, C6, C9, C10, C12, C14, C16, C18 or the like) heteroaryl, or C6-C18 (for example, C6, C9, C10, C12, C14, C16, C18 or the like) arylamine.

In an embodiment, the ring A is any one of phenylene, biphenylene, naphthylene, terphenylene, pyridinylene or phenylene-naphthylene.

In an embodiment, L is selected from any one of a single bond, phenylene, biphenylene, naphthylene, terphenylene, pyridinylene or phenylene-pyridinylene.

In an embodiment, two of $X_1$ to $X_3$ are N or each of $X_1$ to $X_3$ is N.

In an embodiment, $R_1$ and $R_2$ are independently selected from any one of the following groups:

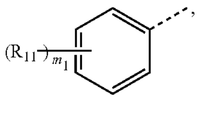

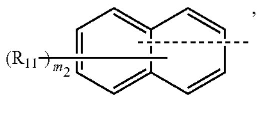

-continued

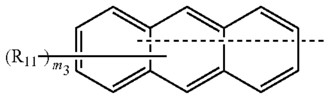

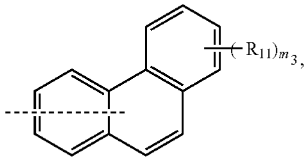

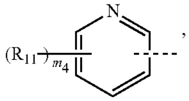

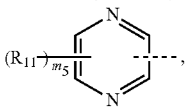

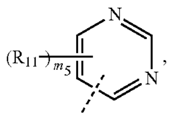

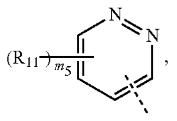

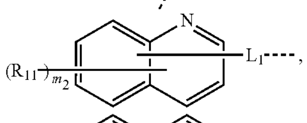

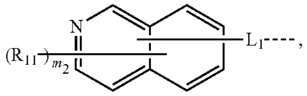

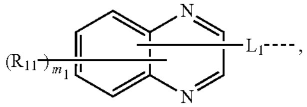

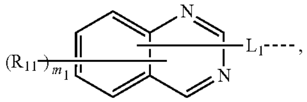

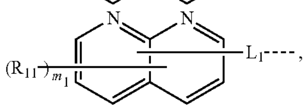

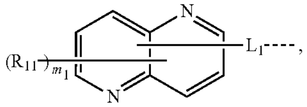

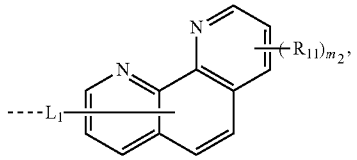

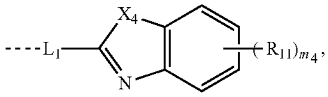

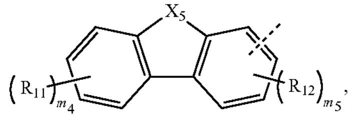

and

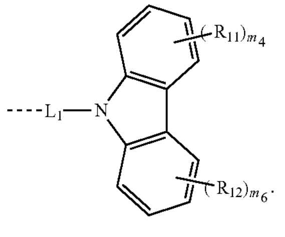

The dashed line represents a linkage site of the group.

$L_1$ is selected from any one of a single bond, or substituted or unsubstituted C6-C20 (for example, C6, C9, C10, C12, C14, C16, C18 or the like) arylene.

$X_4$ is selected from O, S or $NR_{N1}$.

$X_5$ is selected from O, S, $NR_{N2}$ or $CR_{C3}R_{C4}$.

$R_{N1}$, $R_{N2}$, $R_{C3}$ and $R_{C4}$ are each independently selected from any one of hydrogen, substituted or unsubstituted C1-C20 (for example, C2, C3, C4, C5, C6, C8, C10, C12, C14, C16, C18, C19 or the like) linear or branched alkyl, substituted or unsubstituted C6-C20 (for example, C6, C9, C10, C12, C14, C16, C18 or the like) aryl, or substituted or unsubstituted C5-C20 (for example, C6, C8, C10, C12, C14, C16, C18 or the like) heteroaryl.

$R_{11}$ and $R_{12}$ are each independently selected from any one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C8, C10, C12, C14, C16, C18 or the like) aryl, C5-C20 (for example, C6, C8, C10, C12, C14, C16, C18 or the like) heteroaryl or C6-C18 arylamine.

$m_1$ is selected from an integer from 0 to 5 and may be, for example, 0, 1, 2, 3, 4 or 5.

$m_2$ is selected from an integer from 0 to 6 and may be, for example, 0, 1, 2, 3, 4, 5 or 6.

$m_3$ is selected from an integer from 0 to 9 and may be, for example, 0, 1, 2, 3, 4, 5, 6, 7, 8 or 9.

$m_4$ and $m_6$ are each independently selected from an integer from 0 to 4 and may be, for example, 0, 1, 2, 3 or 4.

$m_5$ is selected from an integer from 0 to 3 and may be, for example, 0, 1, 2 or 3.

In an embodiment, $R_1$ and $R_2$ are independently selected from any one of the following groups, or any one of the following groups substituted with a substituent:

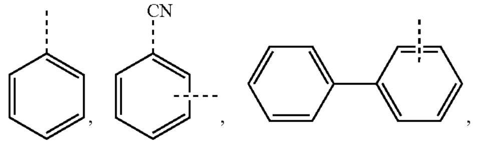

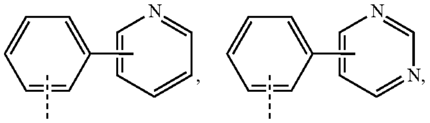

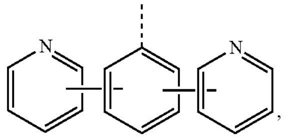

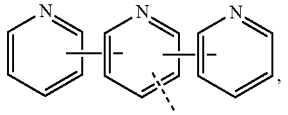

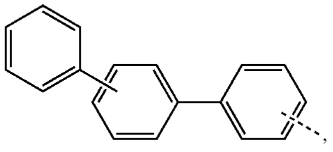

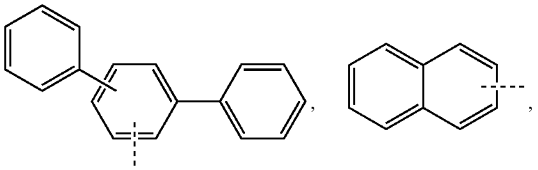

-continued

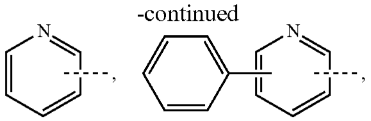

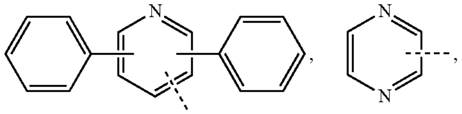

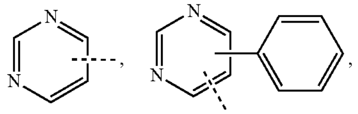

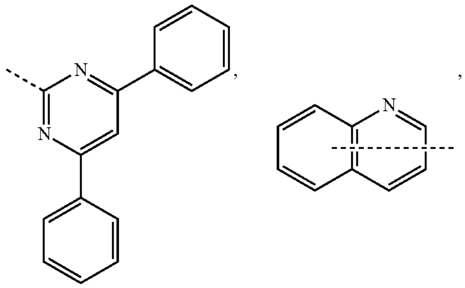

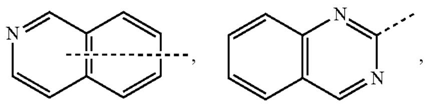

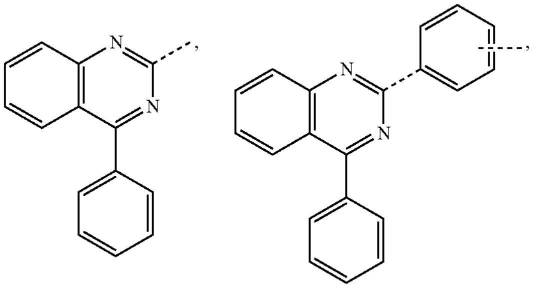

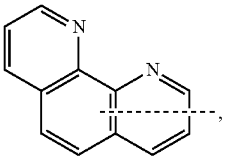

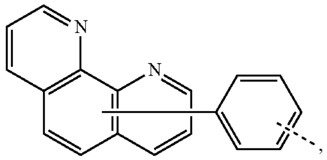

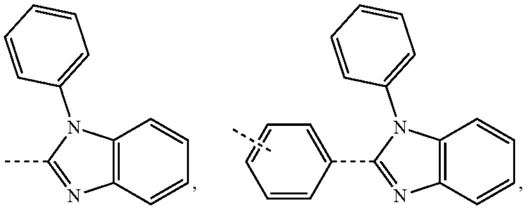

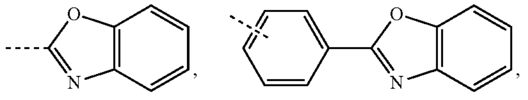

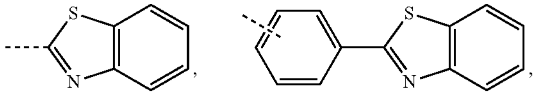

-continued

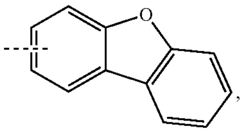
,
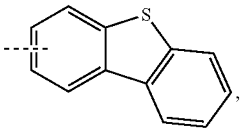
,
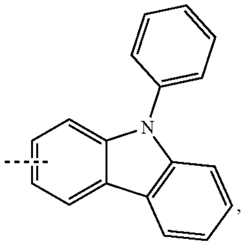
,
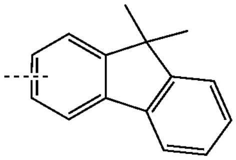
,
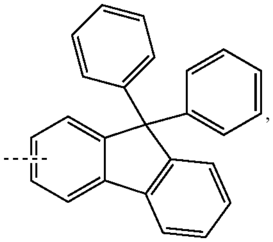
,

-continued

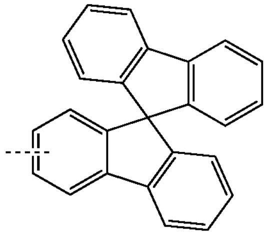
, and
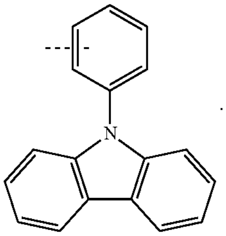
.

The dashed line represents a linkage site of the group.

The substituted substituents are each independently selected from at least one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C9, C10, C12, C14, C16, C18 or the like) aryl, C5-C20 (for example, C6, C9, C10, C12, C14, C16, C18 or the like) heteroaryl or C6-C18 (for example, C6, C9, C10, C12, C14, C16, C18 or the like) arylamine.

In a specific embodiment, the organic compound is selected from any one of the following compounds:

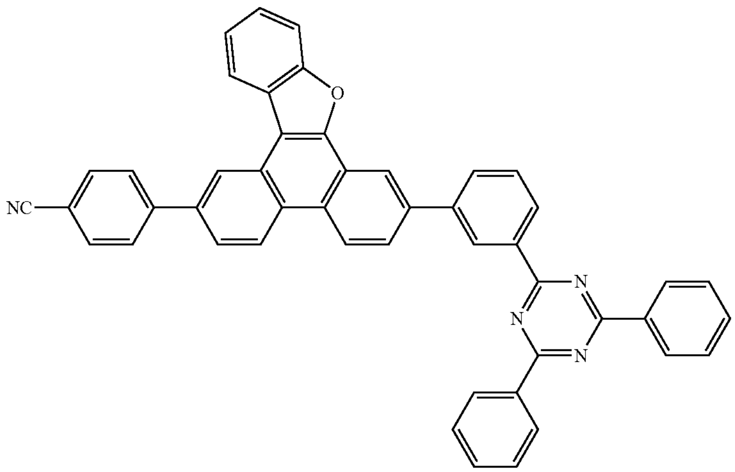

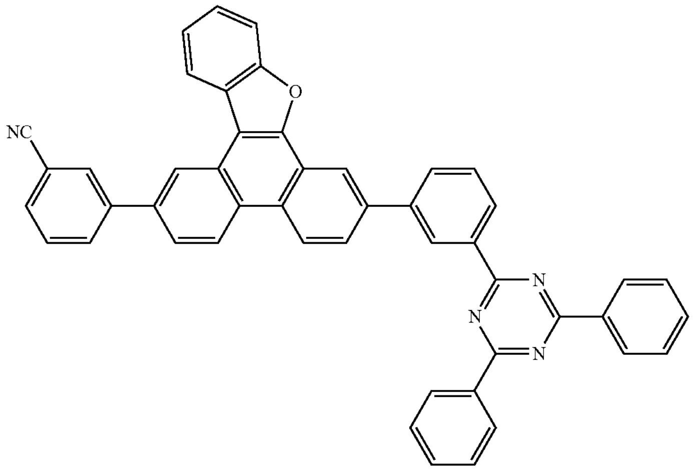

-continued
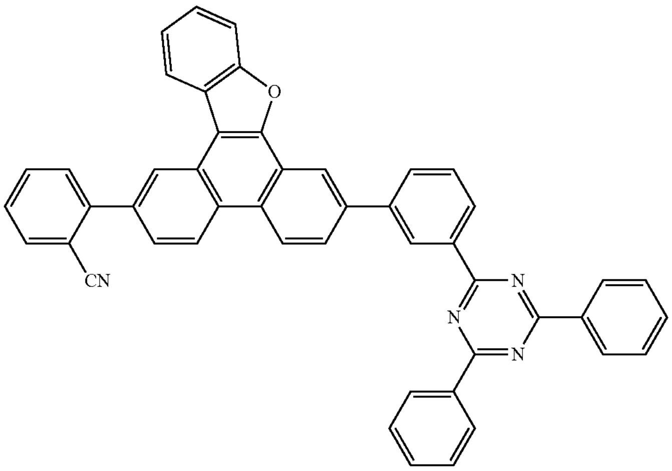
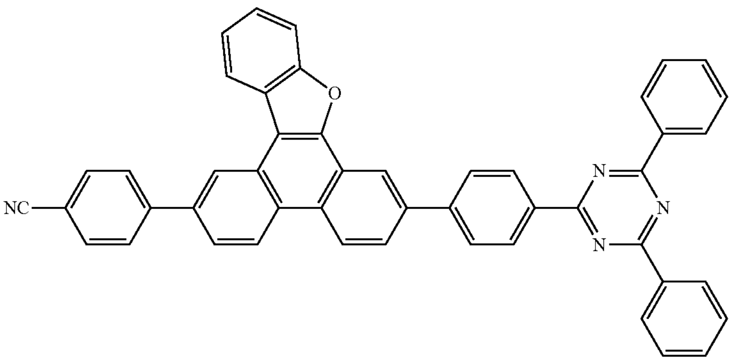
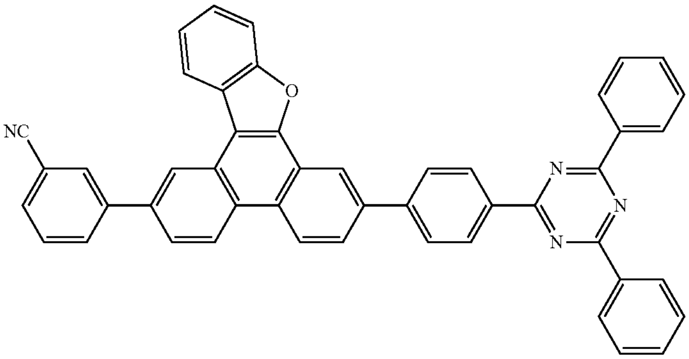
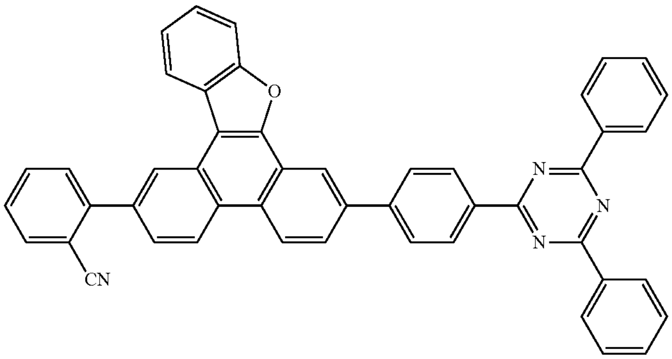

-continued
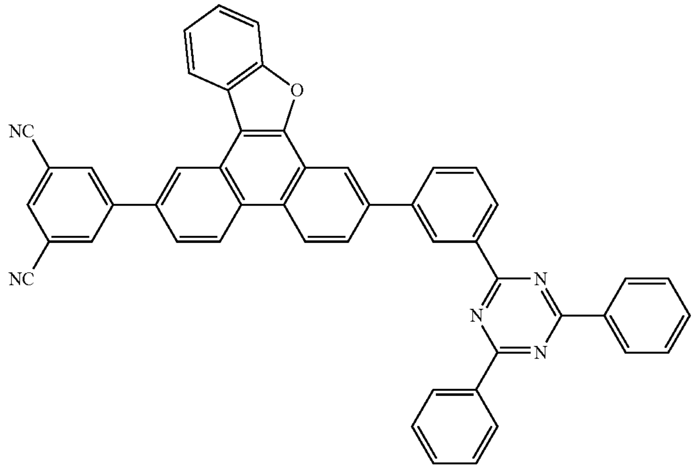
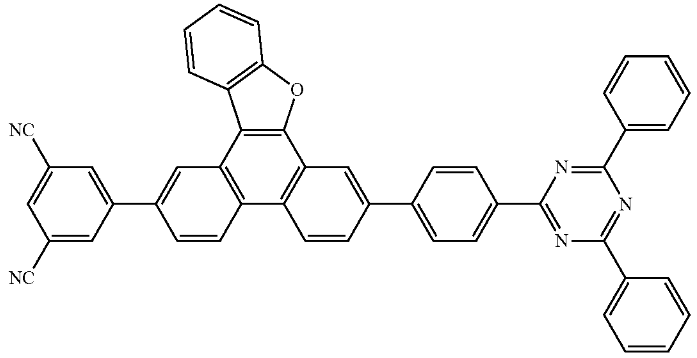
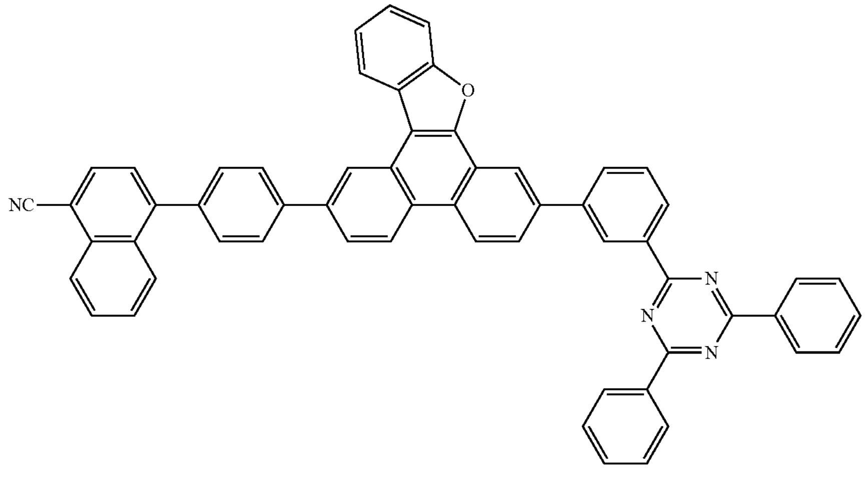

-continued
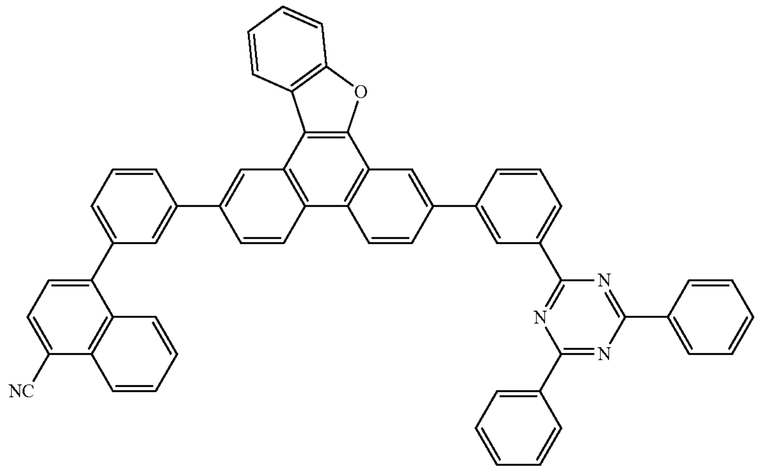
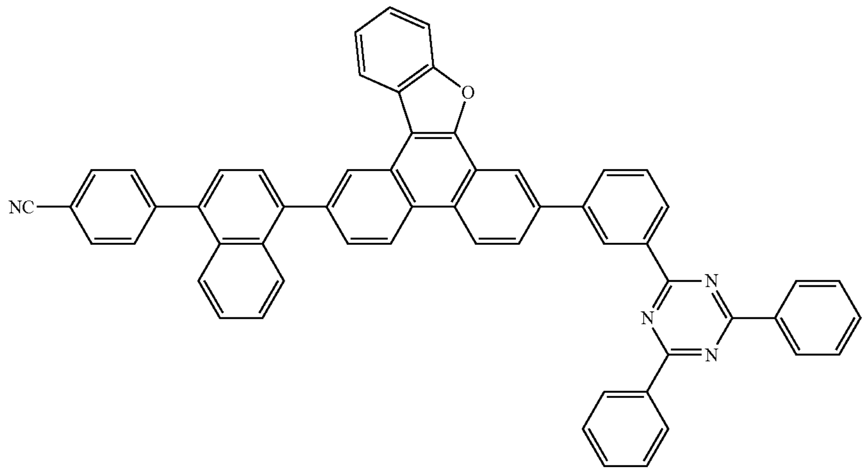
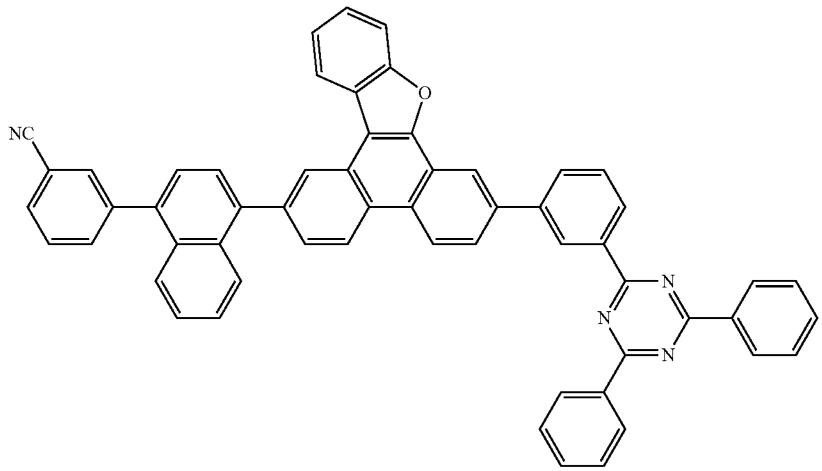

-continued
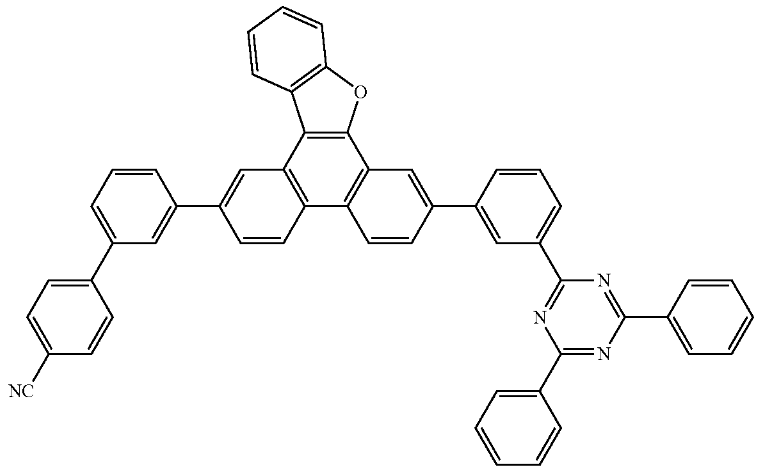
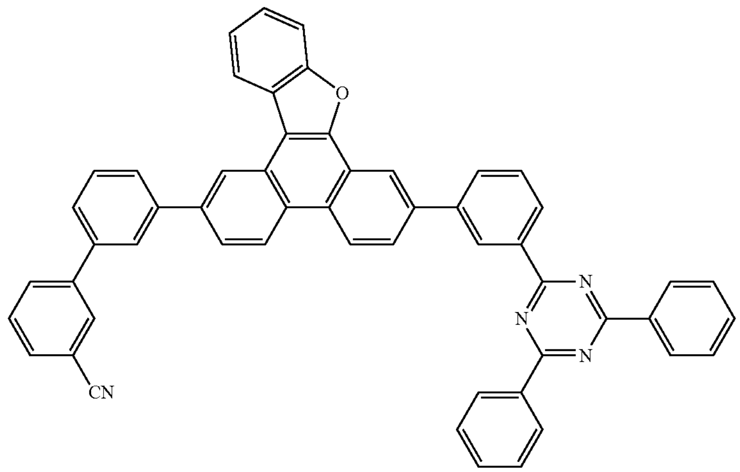
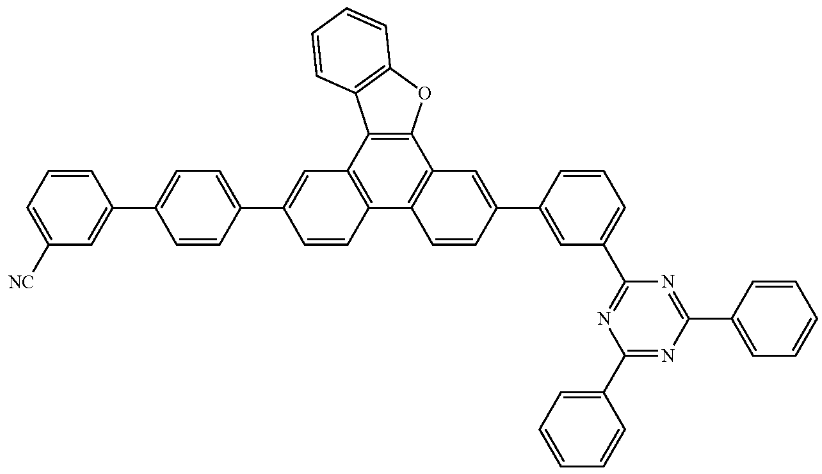

-continued
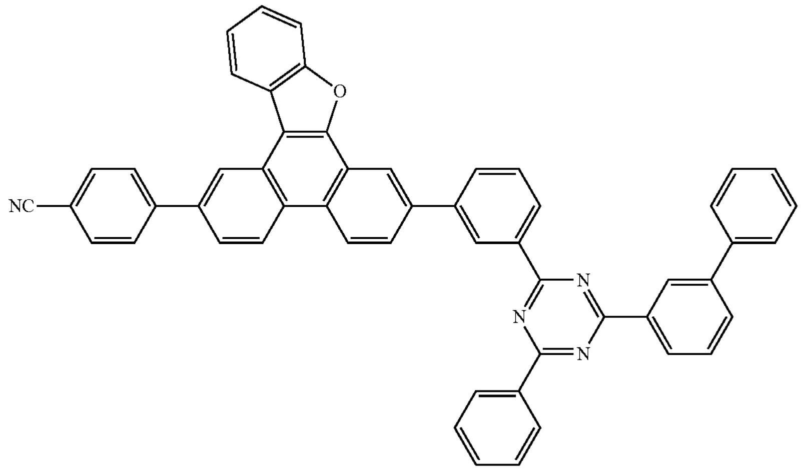
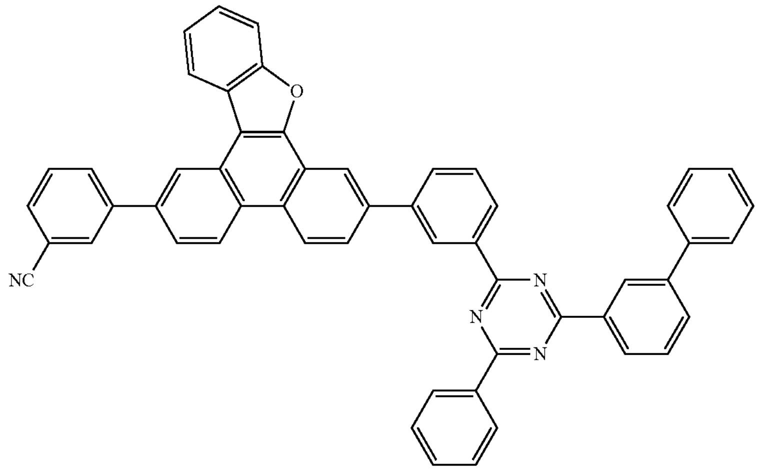
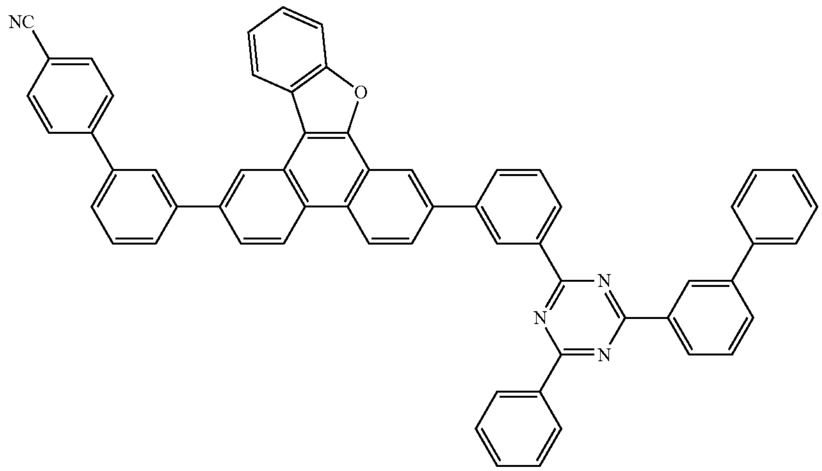

-continued
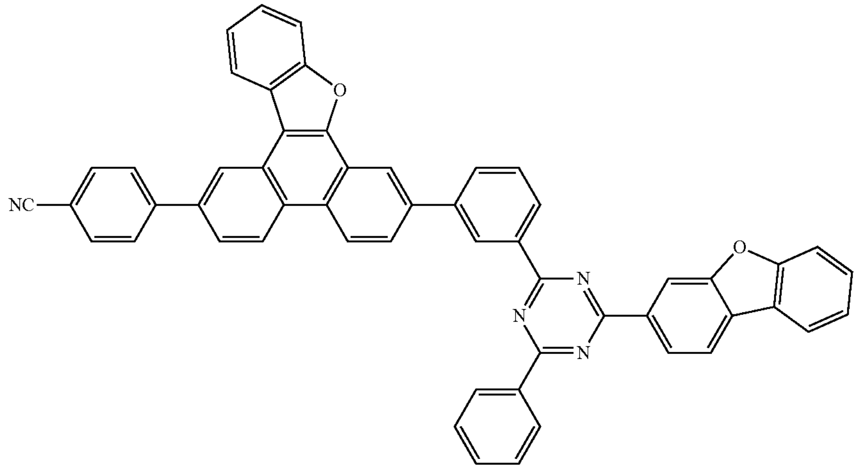
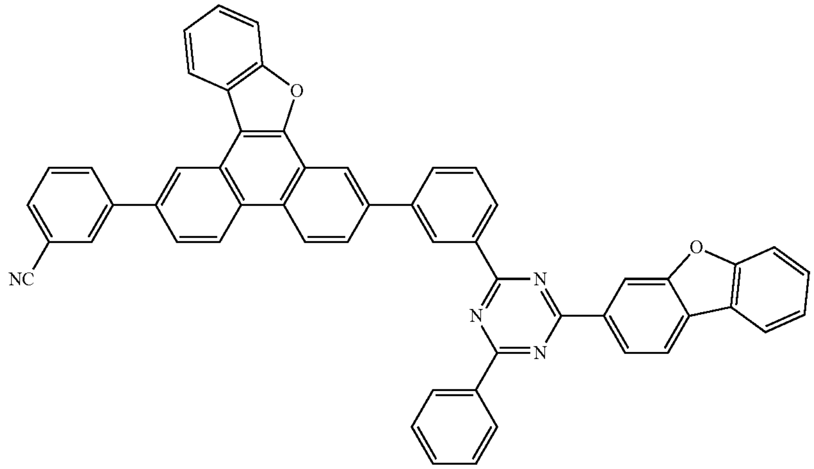
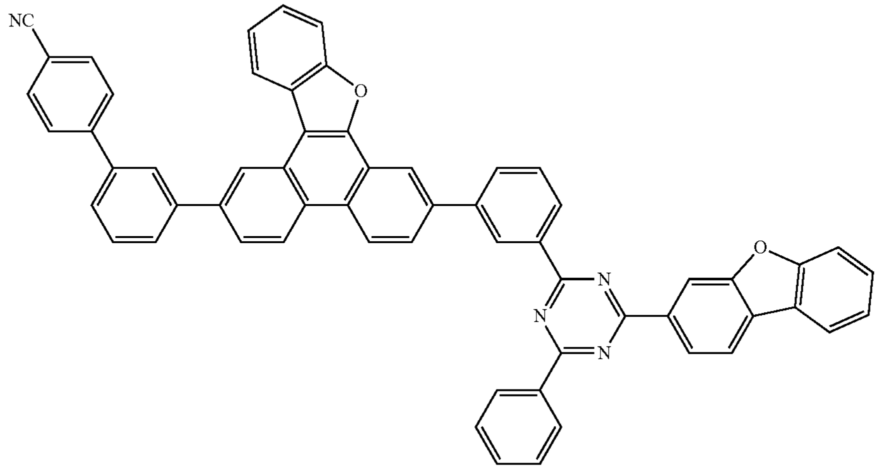

-continued
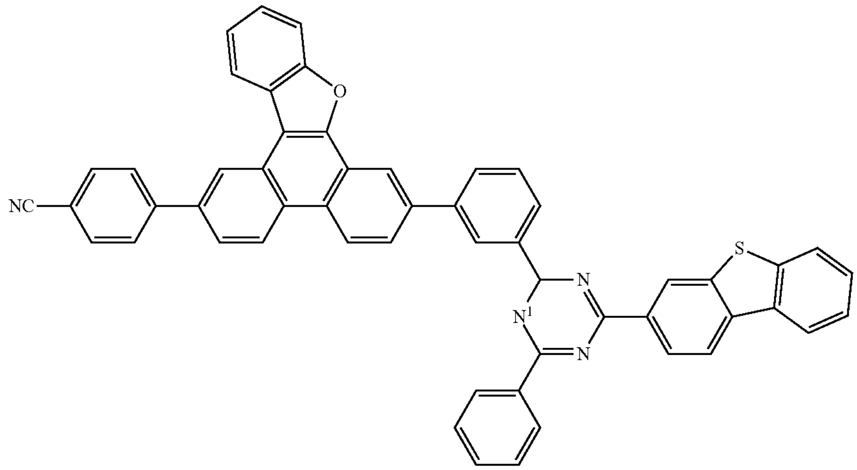
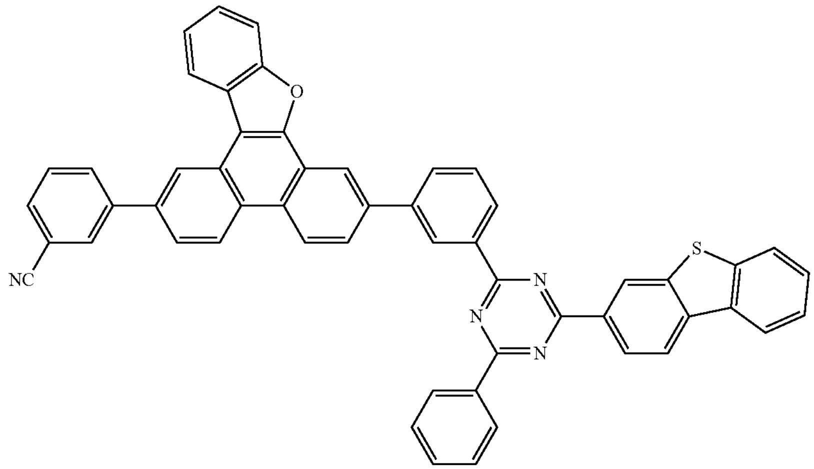
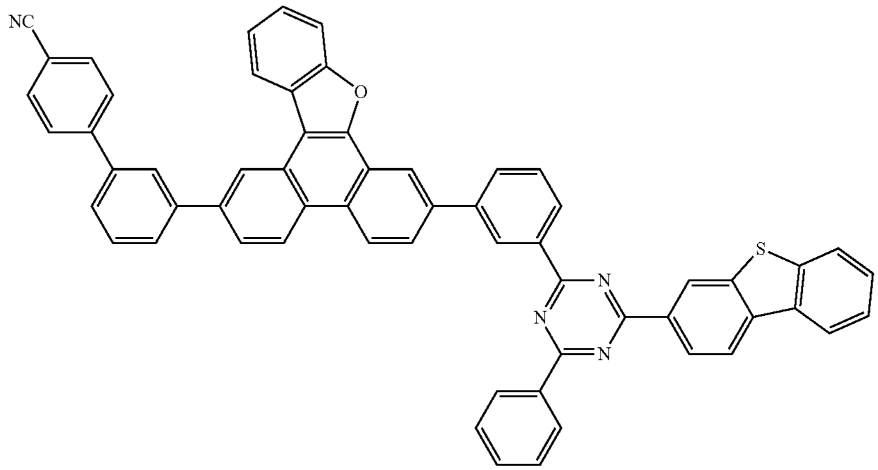

-continued
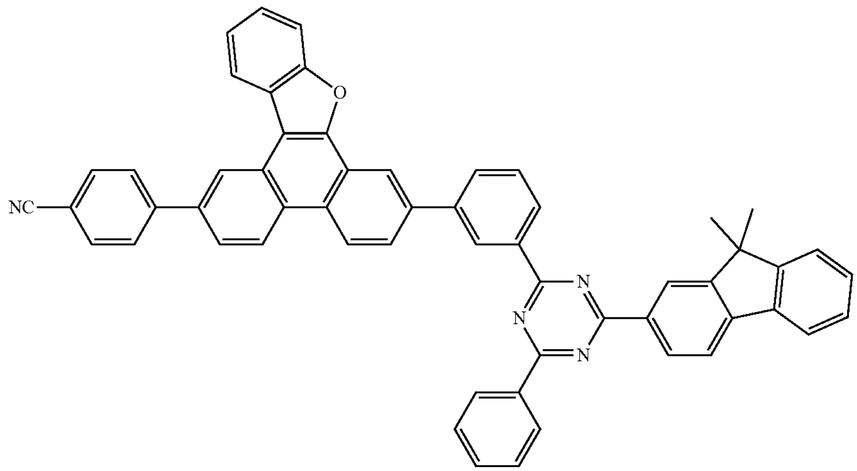
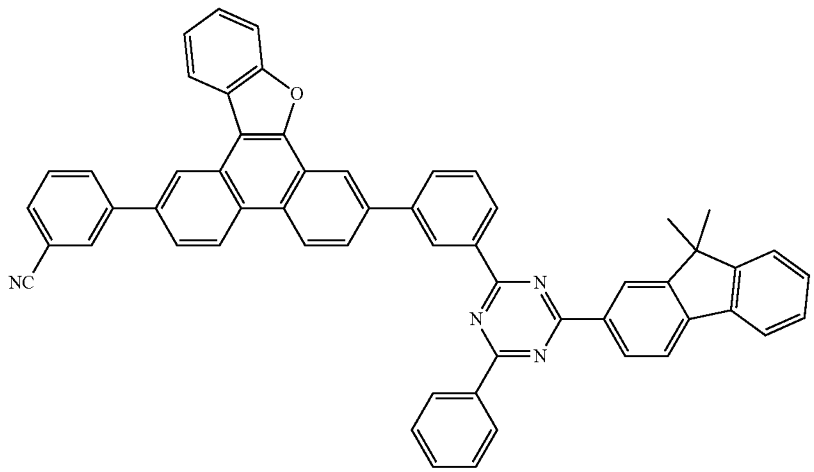
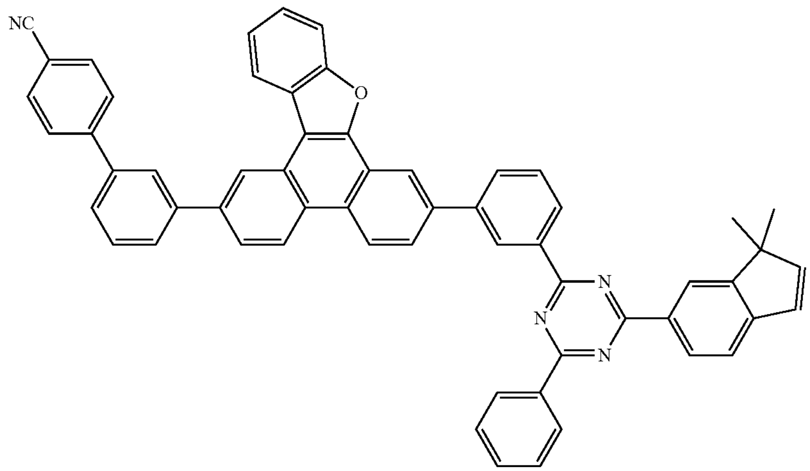

-continued
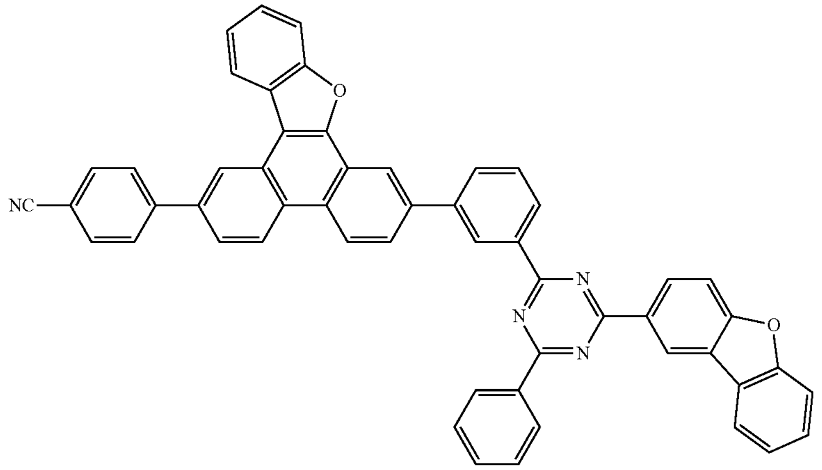
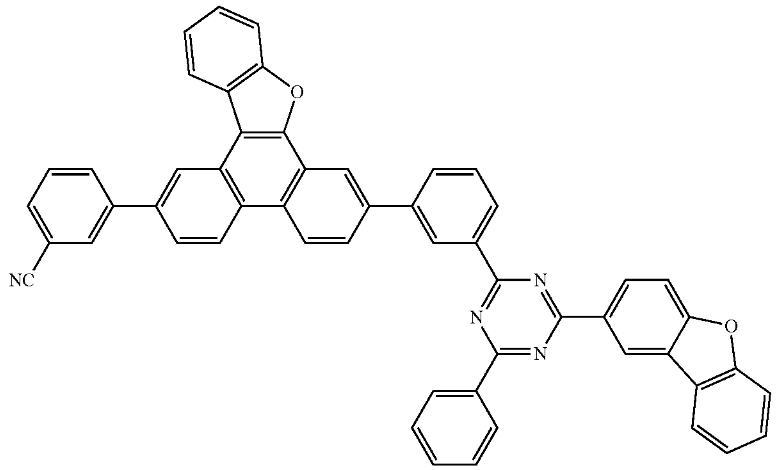
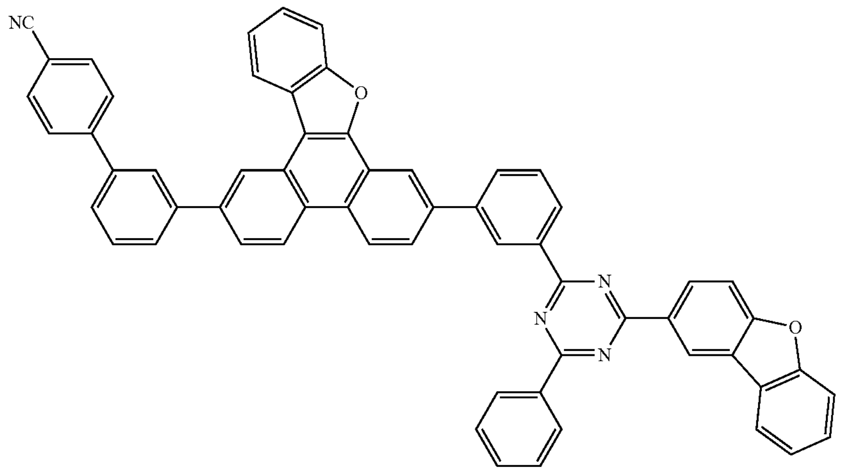

-continued
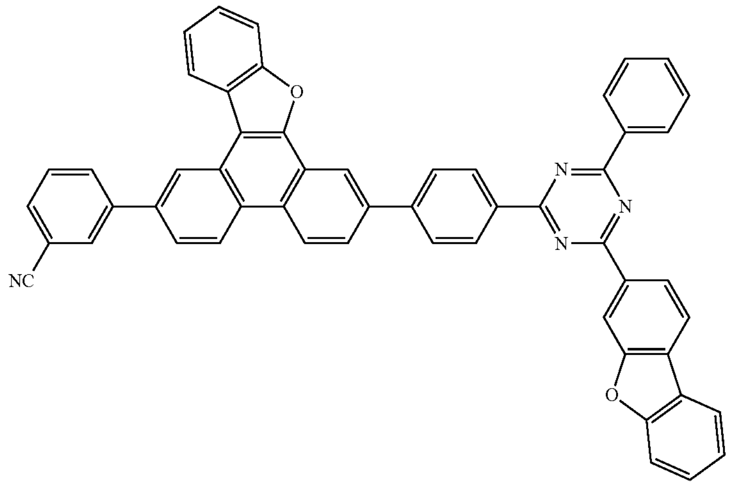
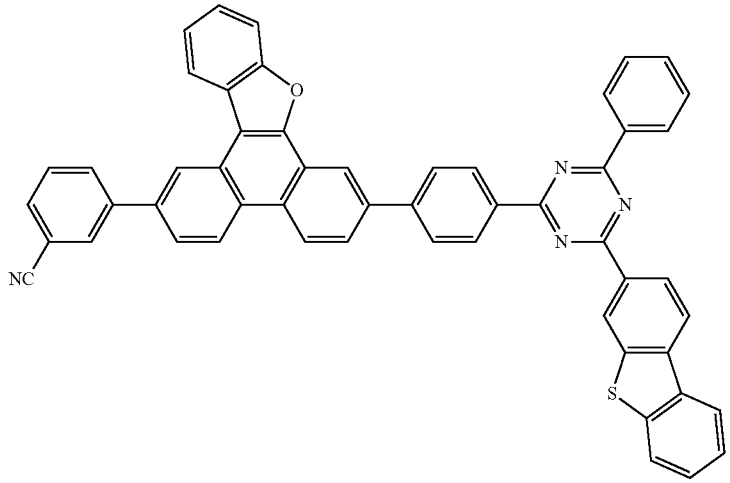
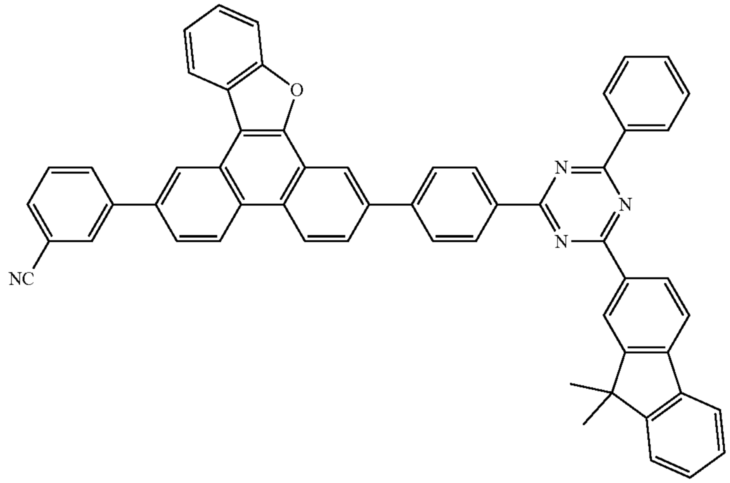

-continued
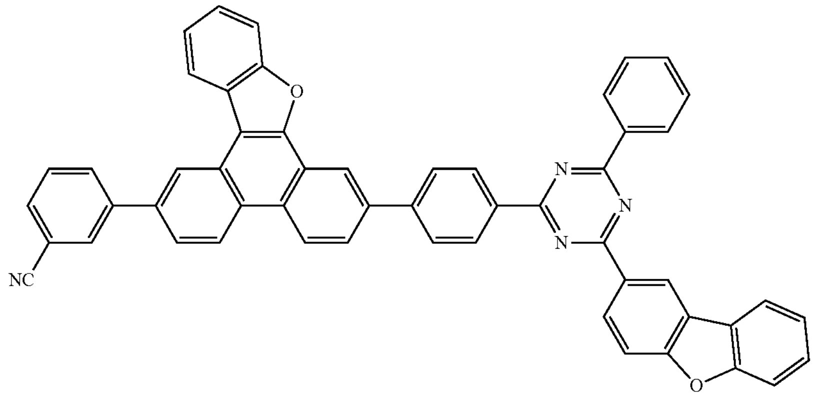
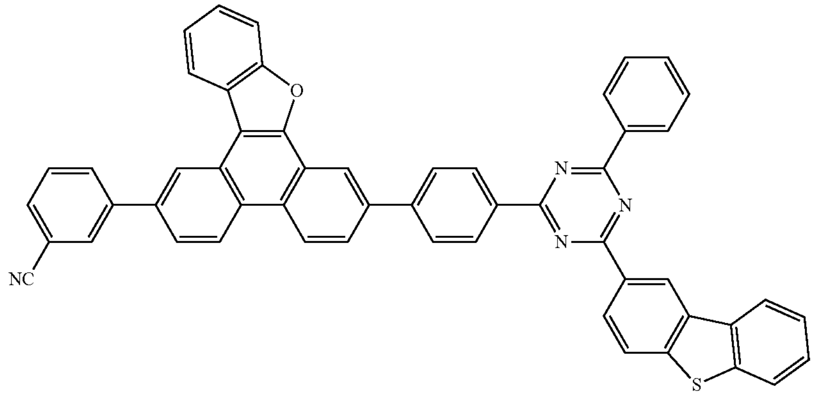
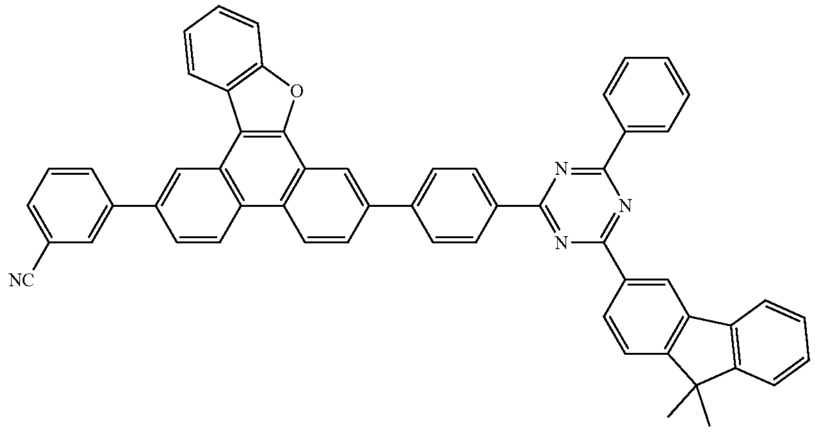
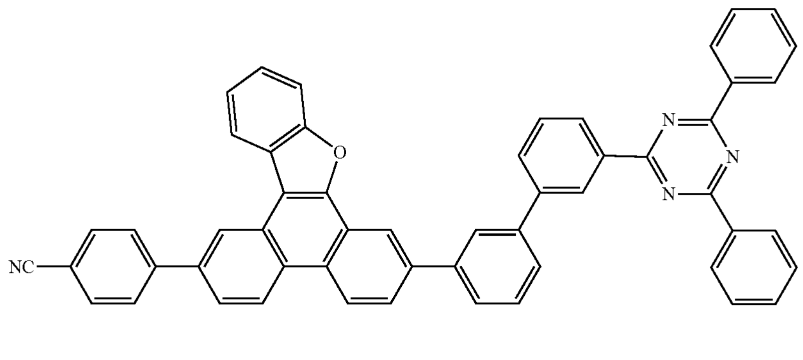

-continued
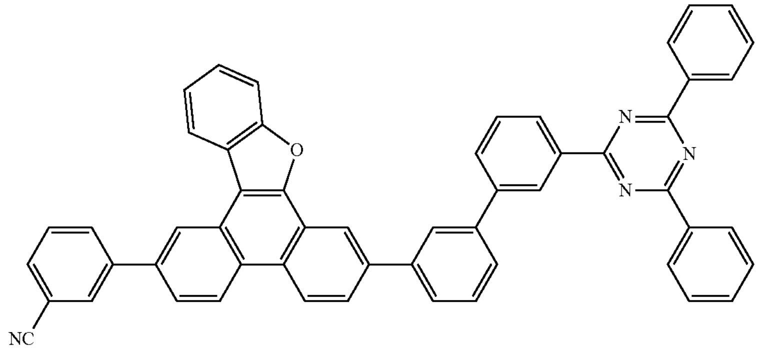
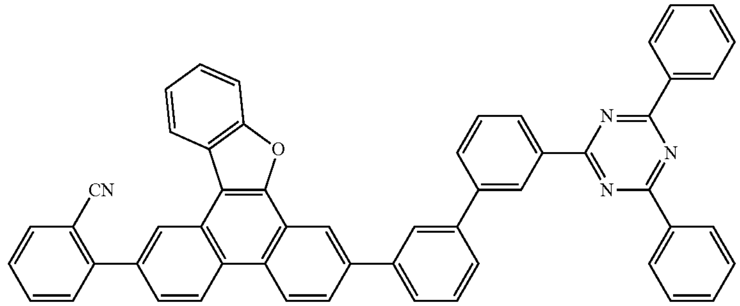
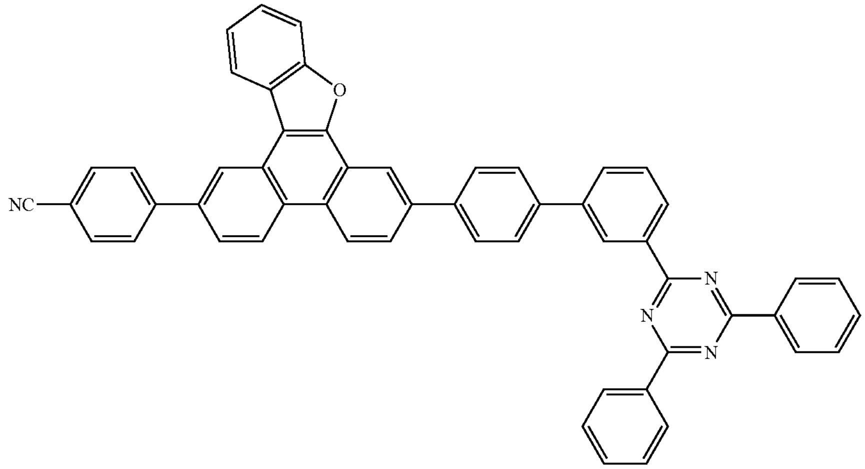
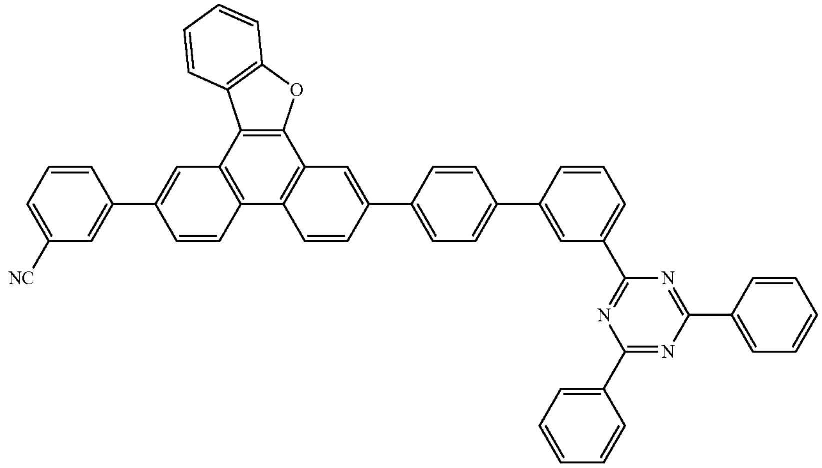

-continued
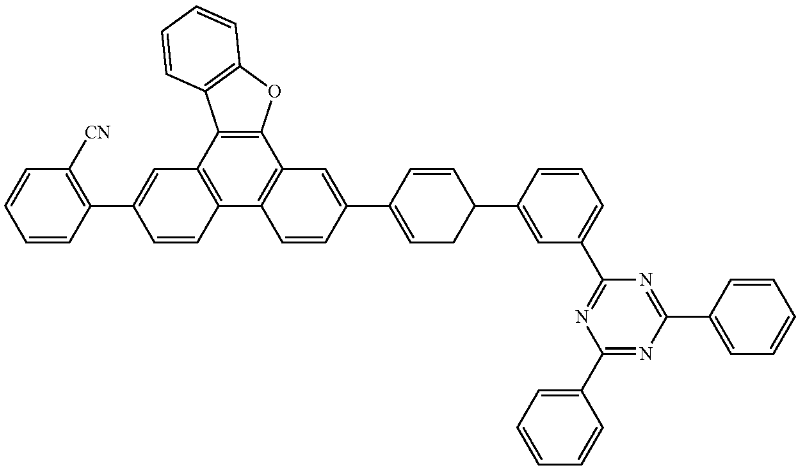
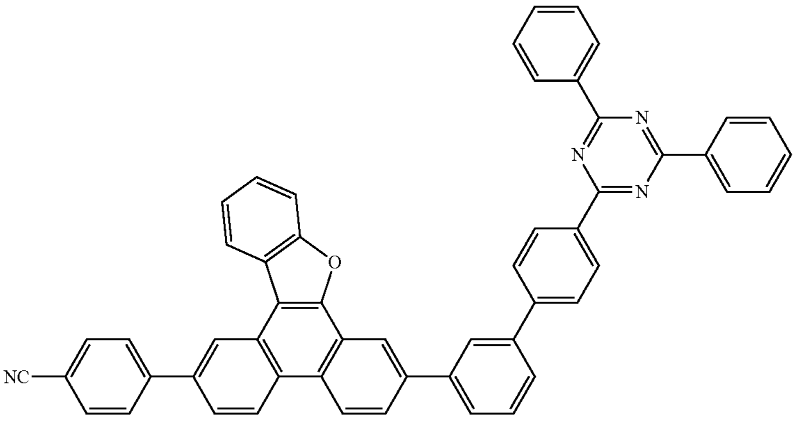
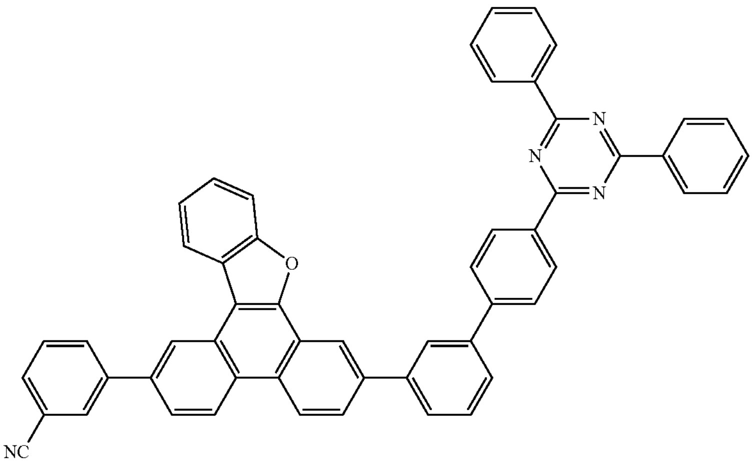

-continued
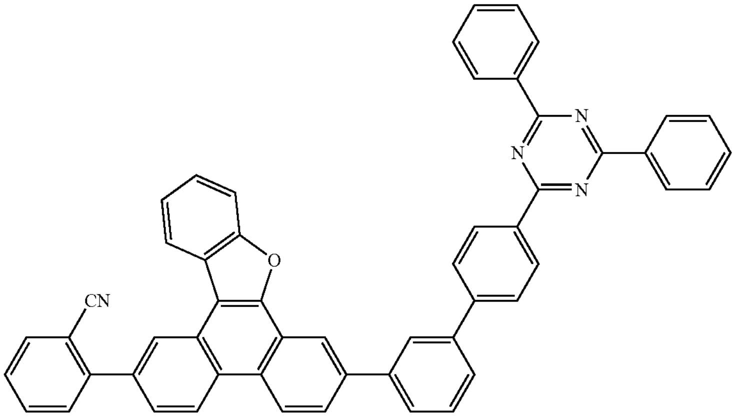
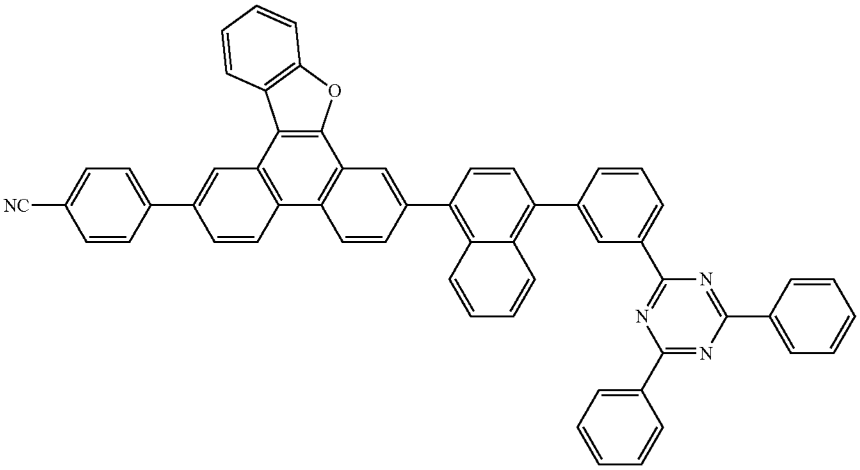
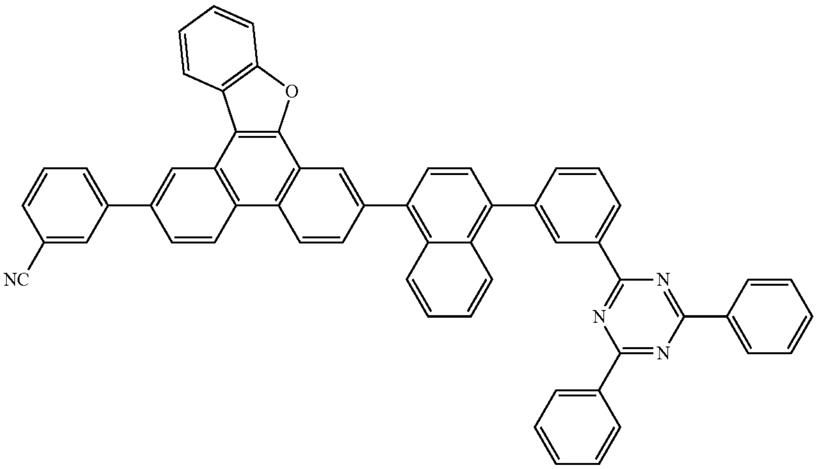

-continued
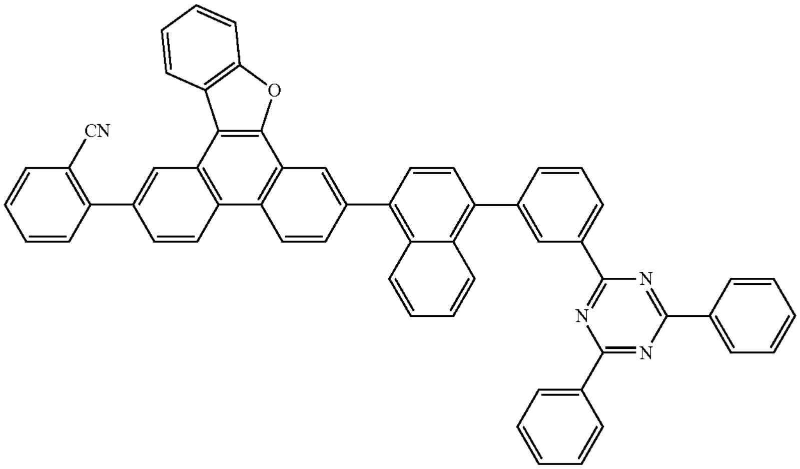
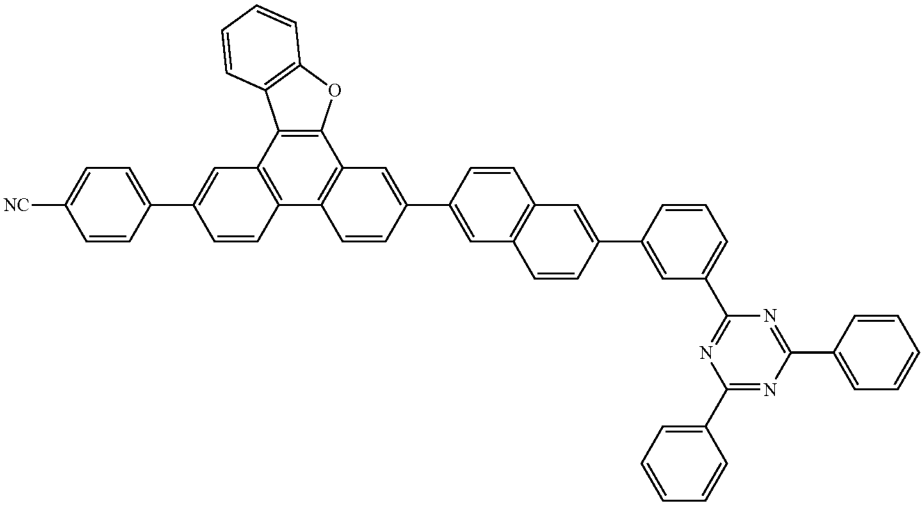
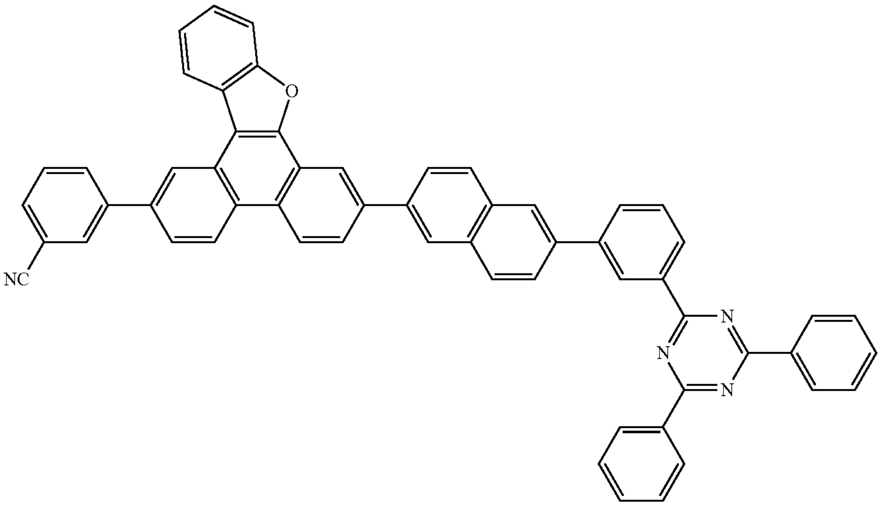

-continued
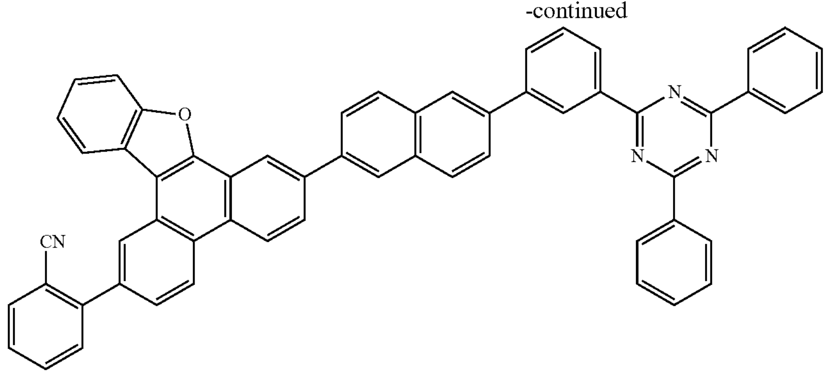
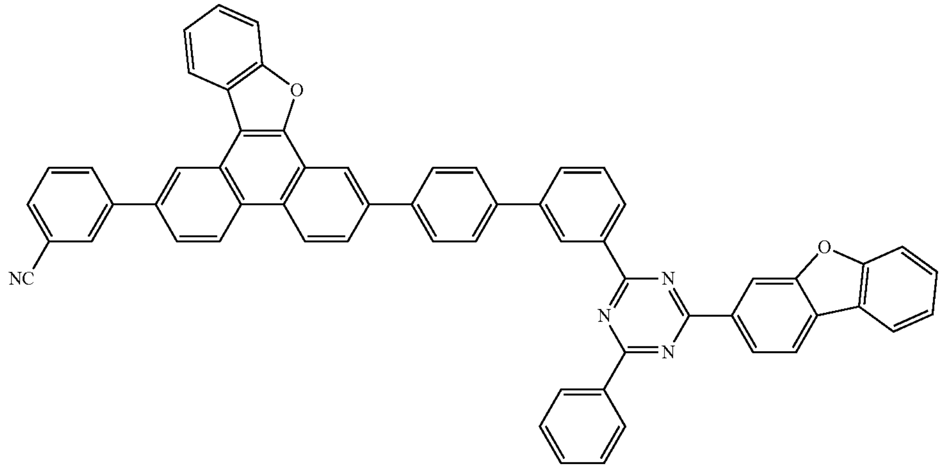
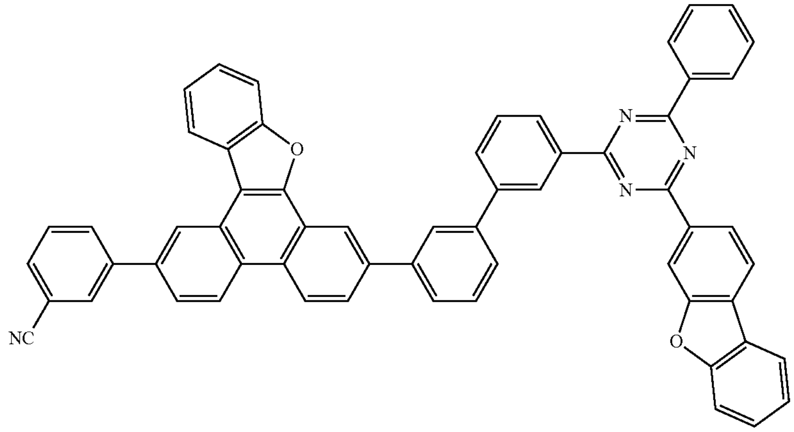
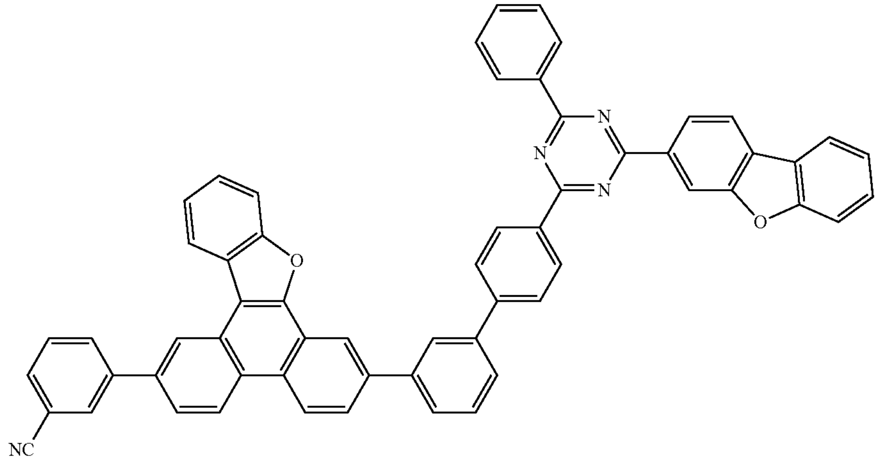

-continued
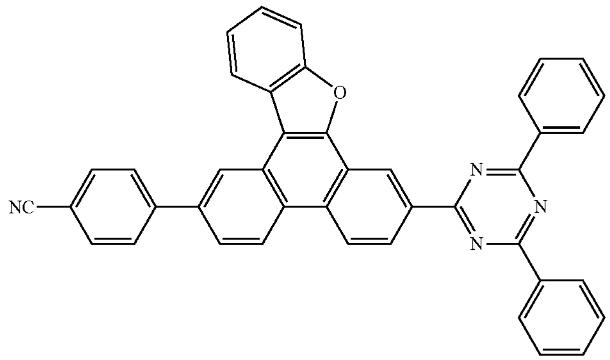
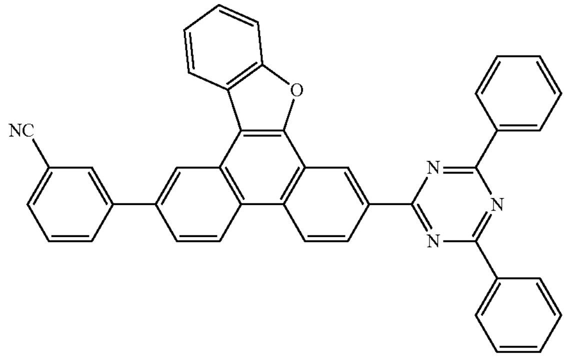
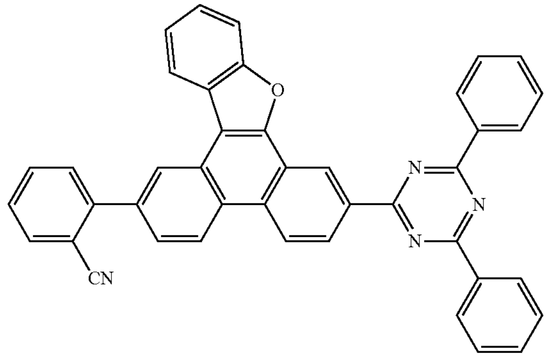
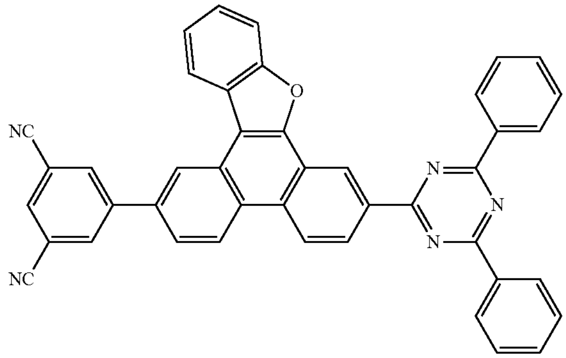
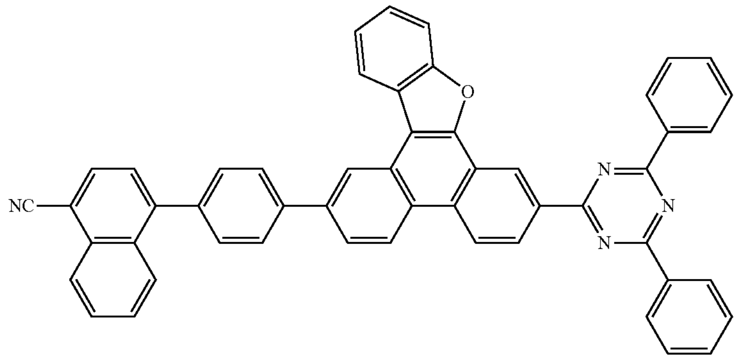

-continued
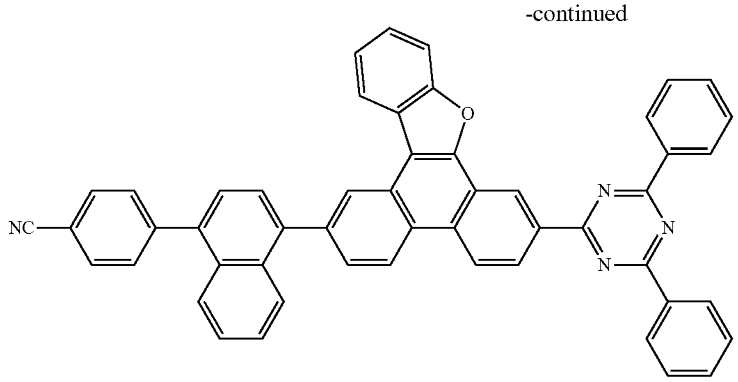
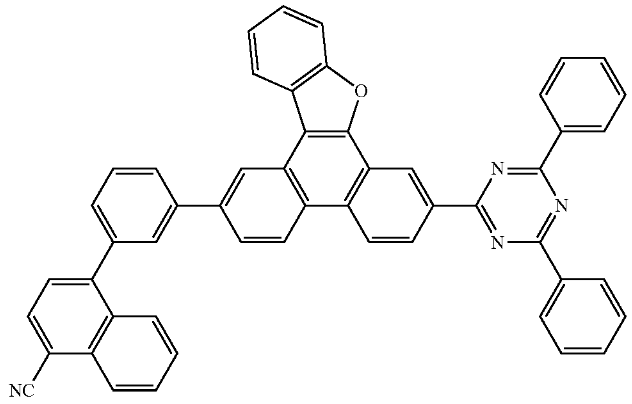
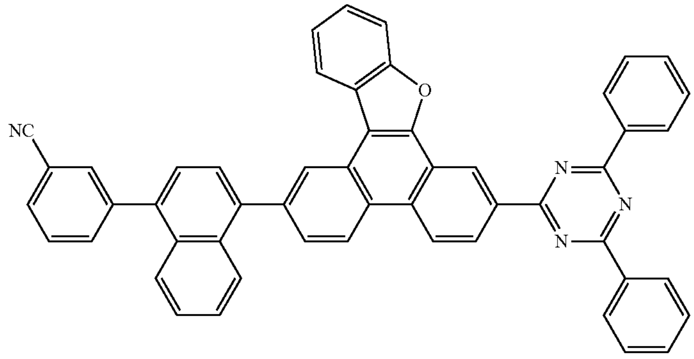
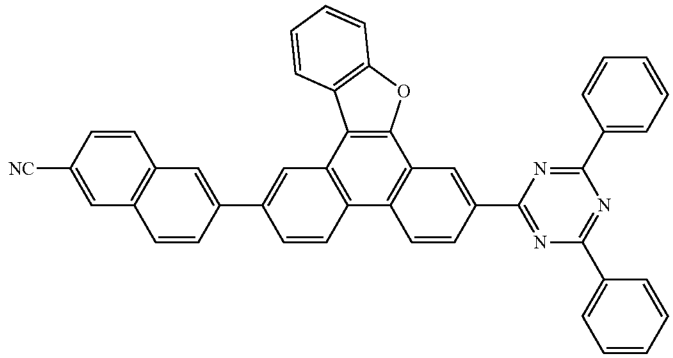

-continued
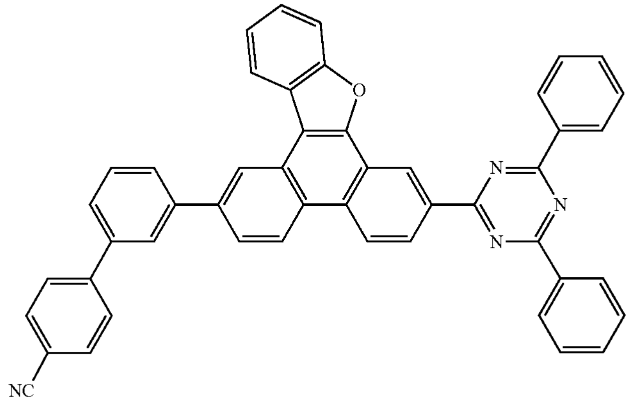
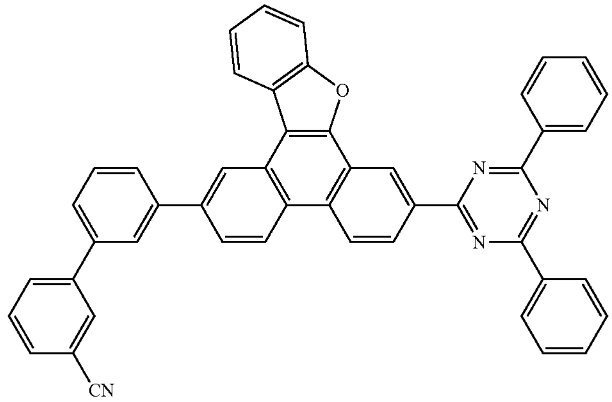
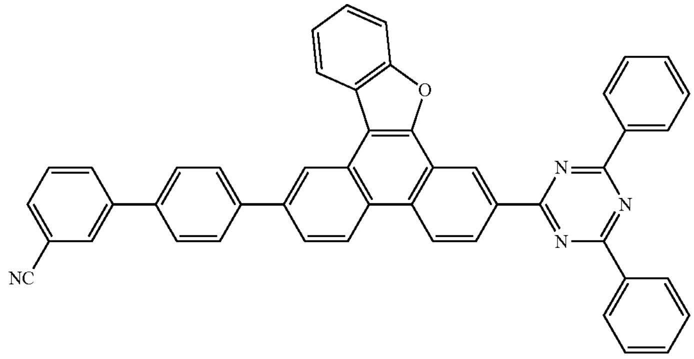
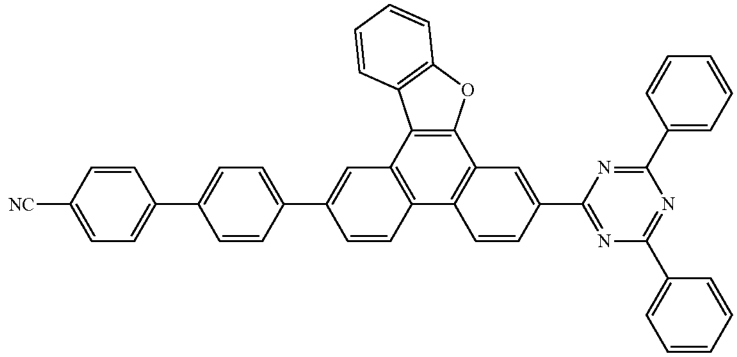

-continued
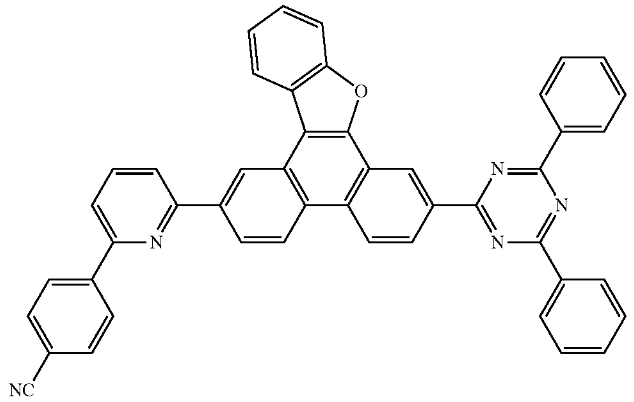
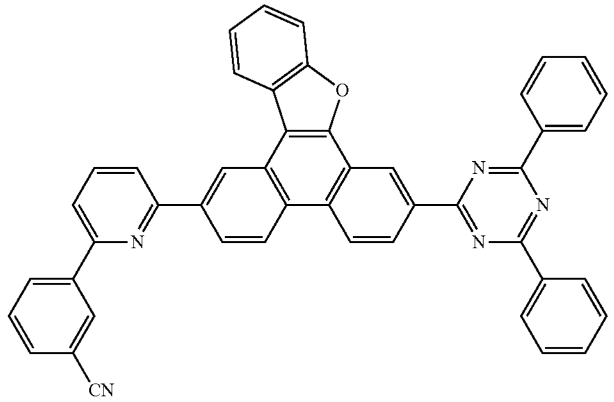
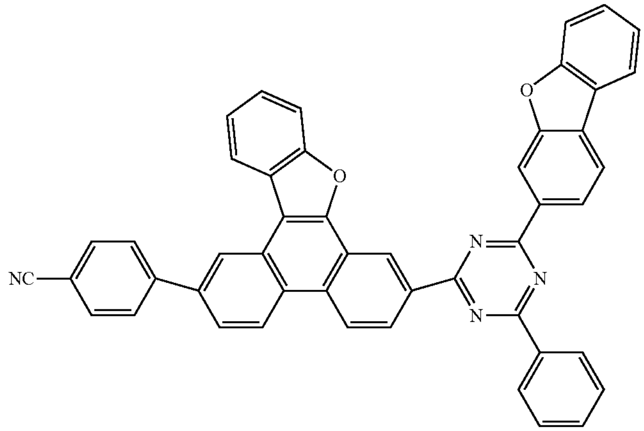
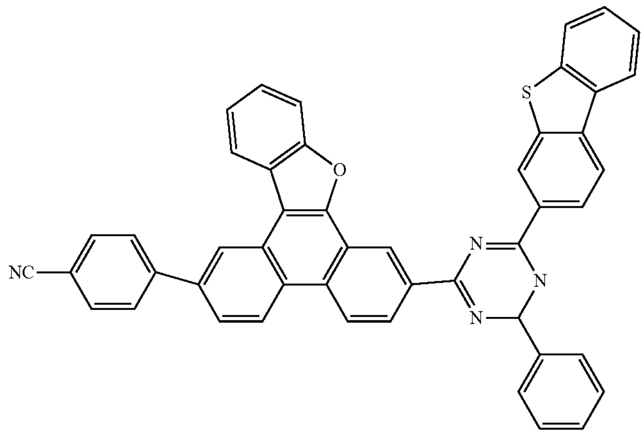

-continued
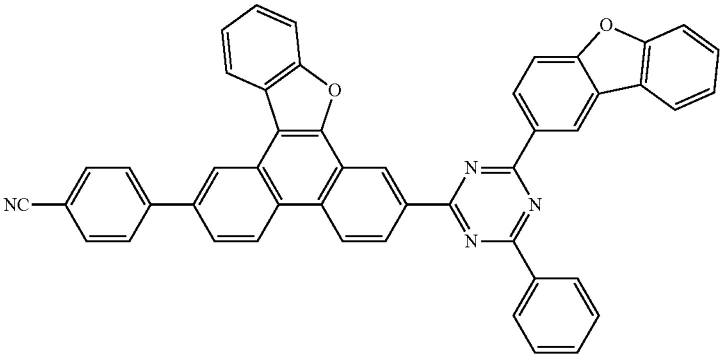
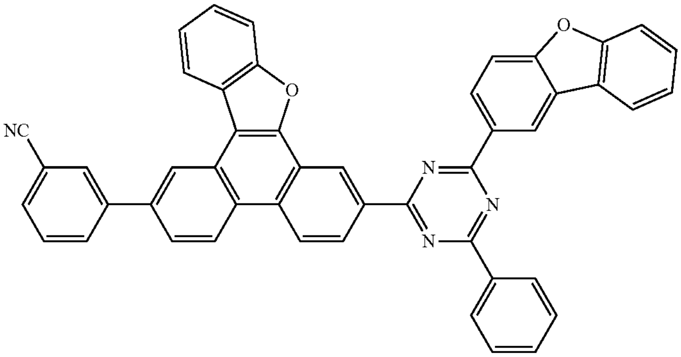
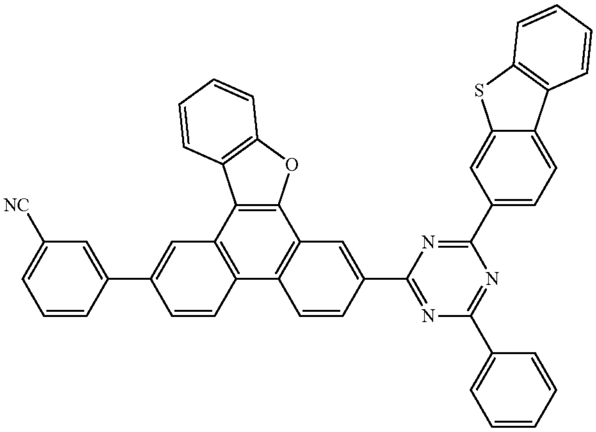
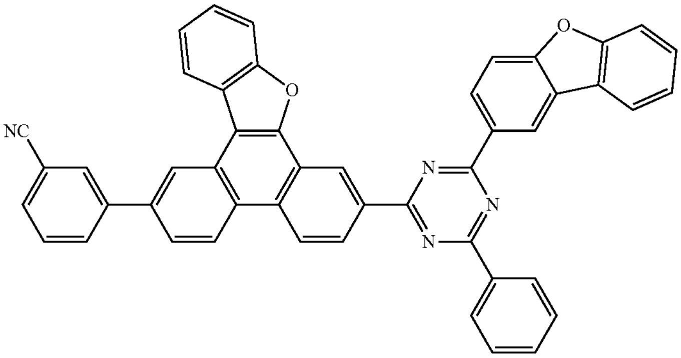

-continued
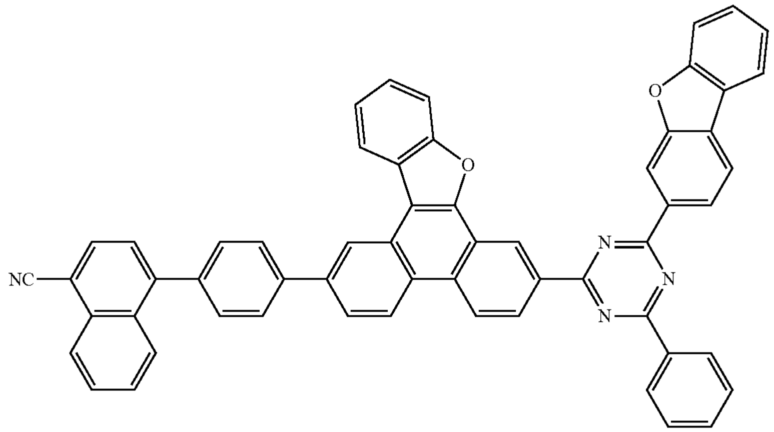
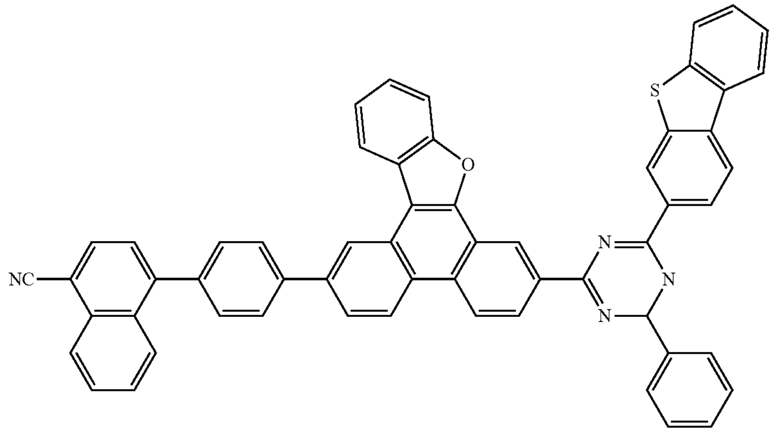
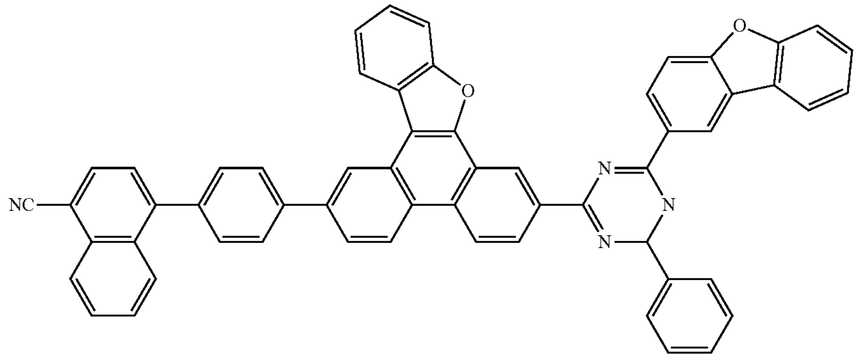
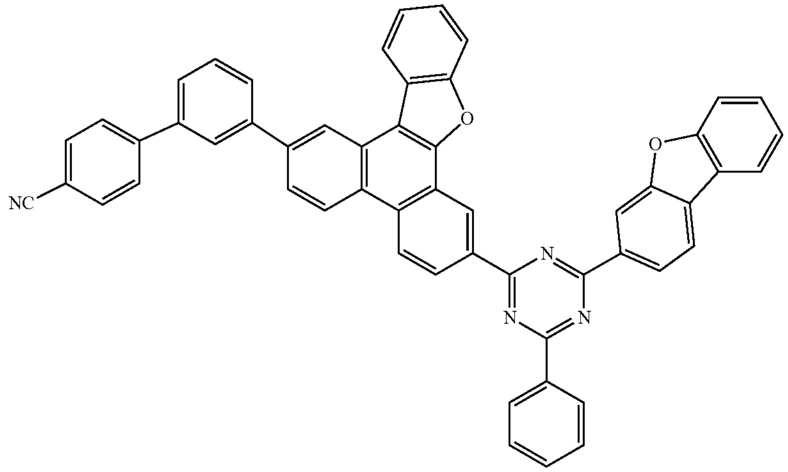

-continued
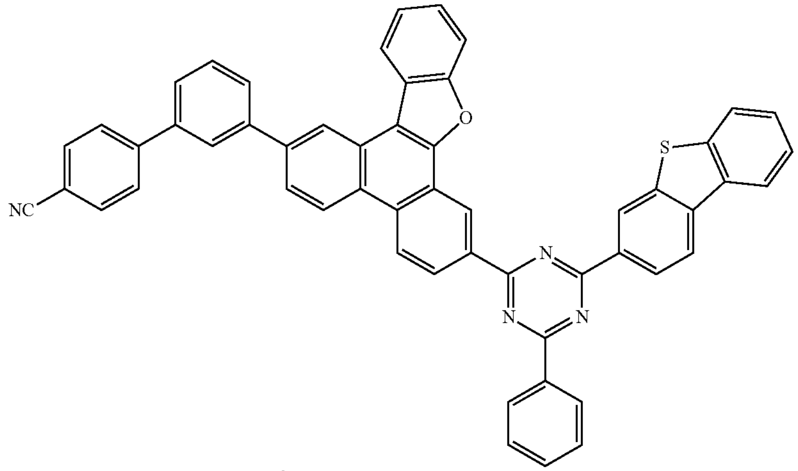
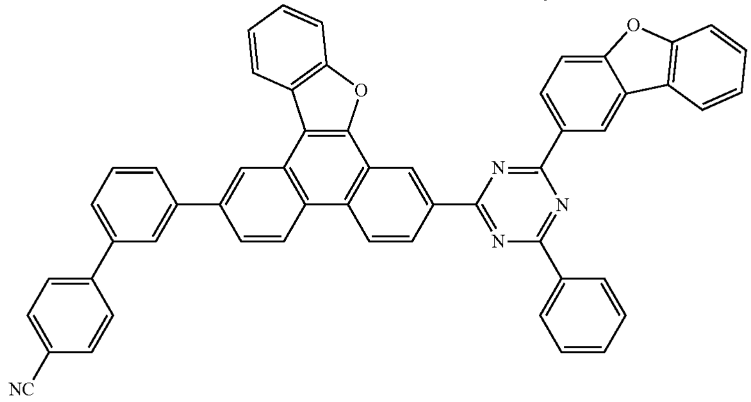
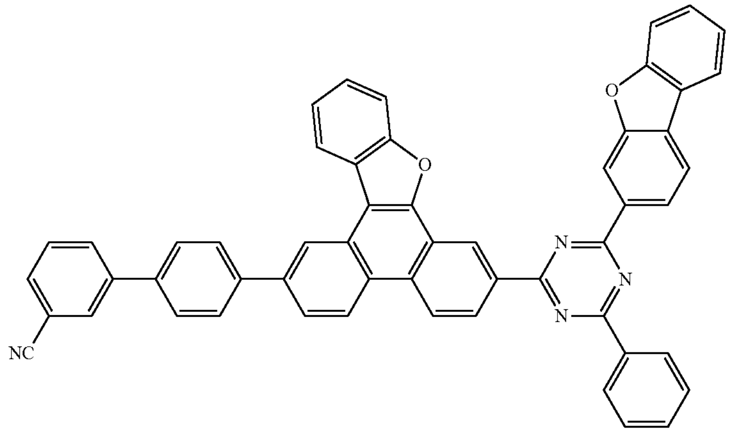
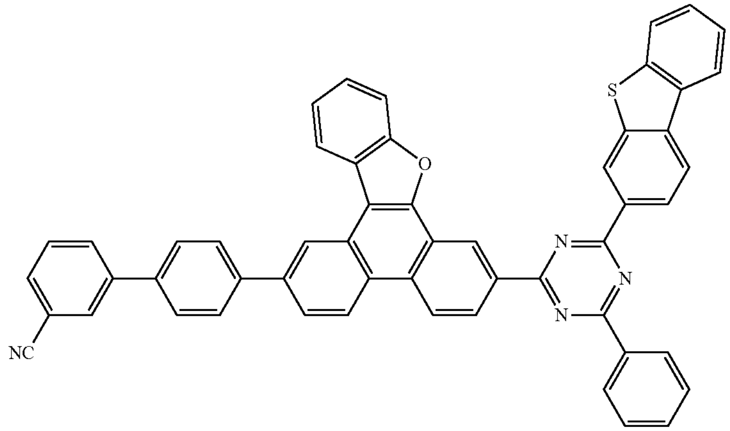

-continued
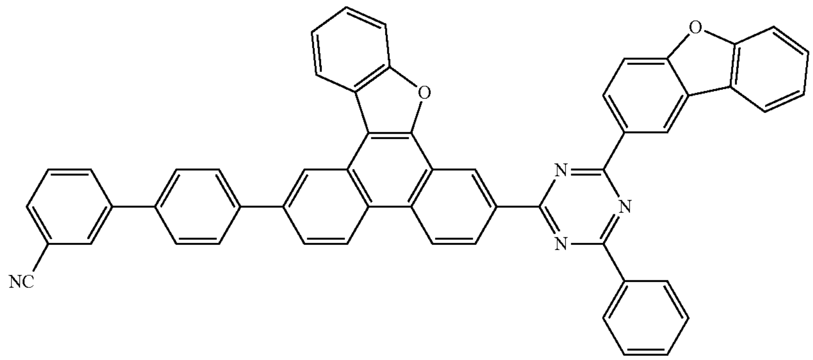
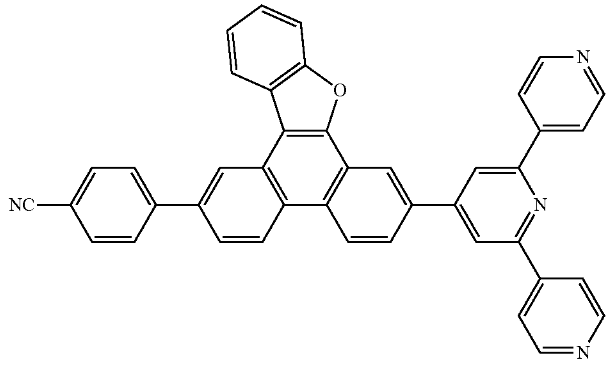
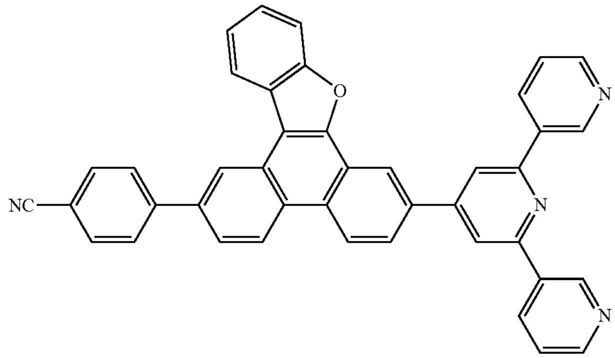
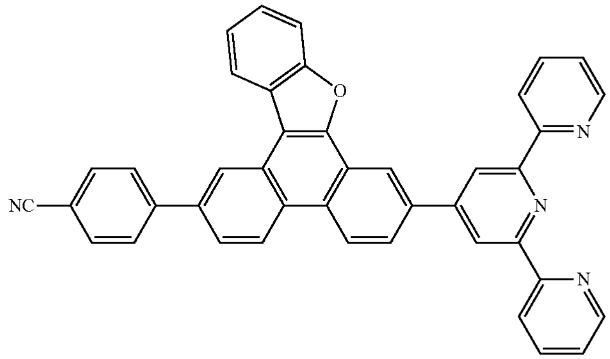

-continued
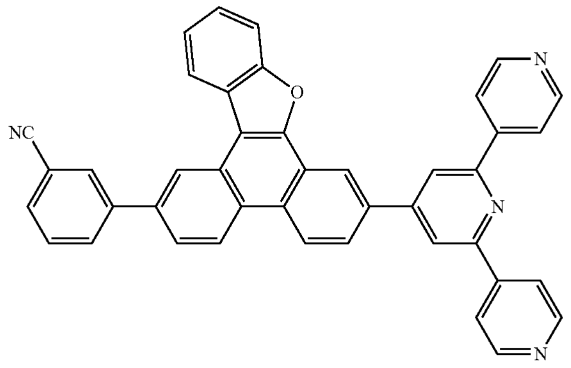
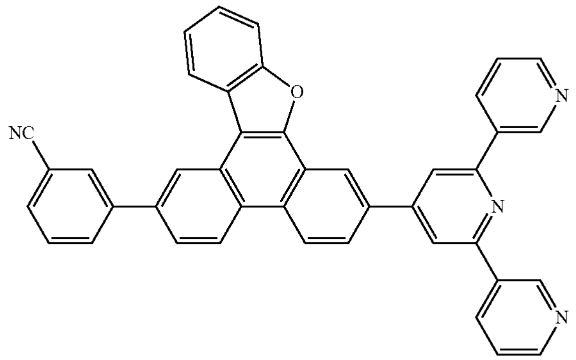
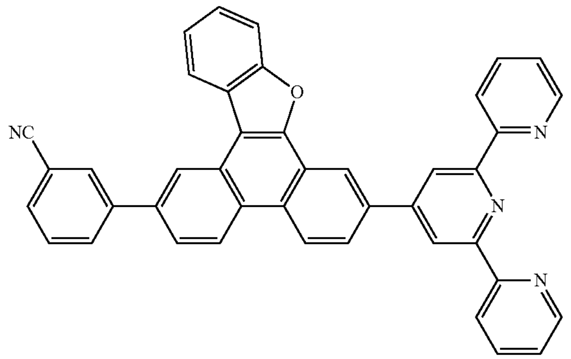
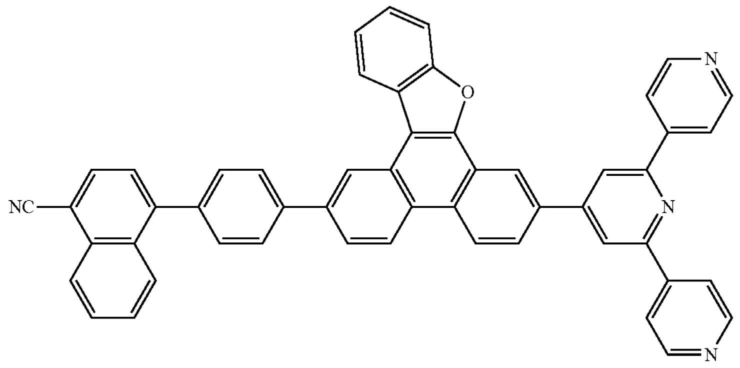

-continued
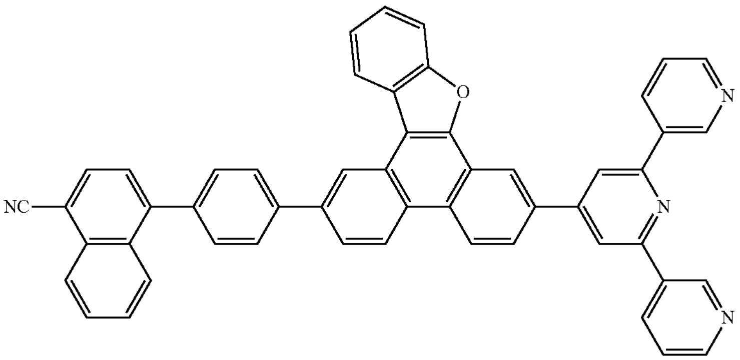
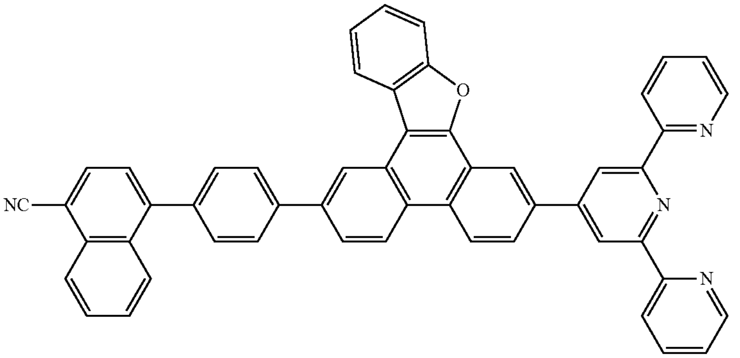
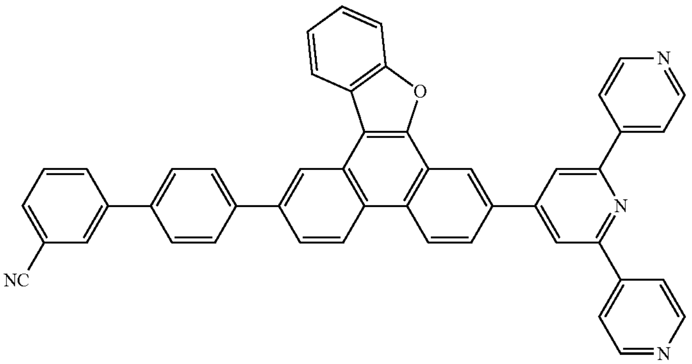
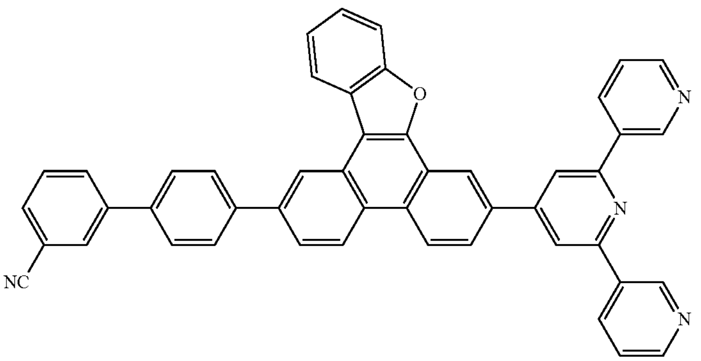

-continued
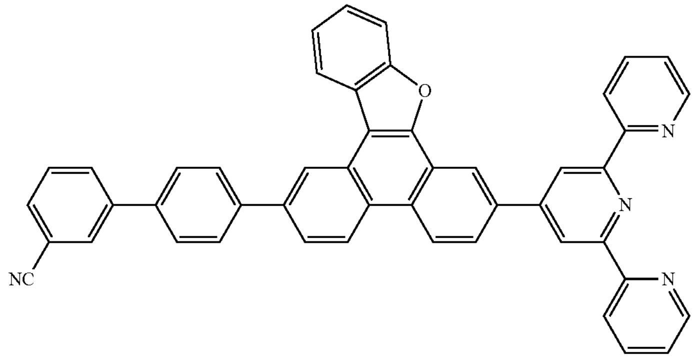
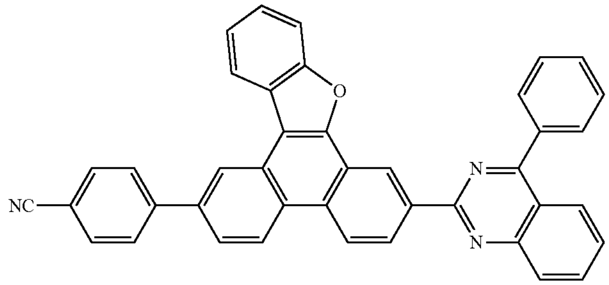
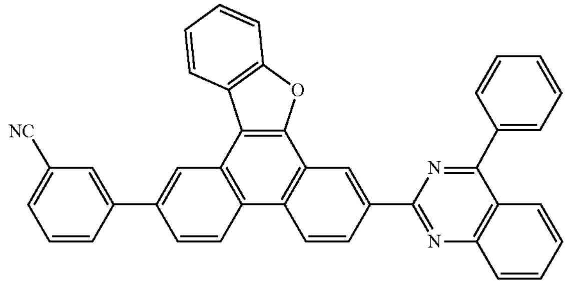
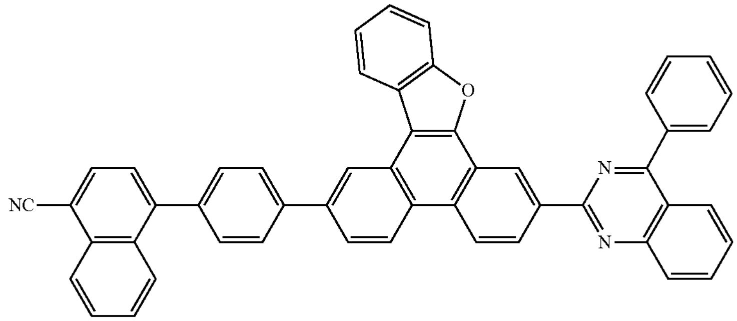
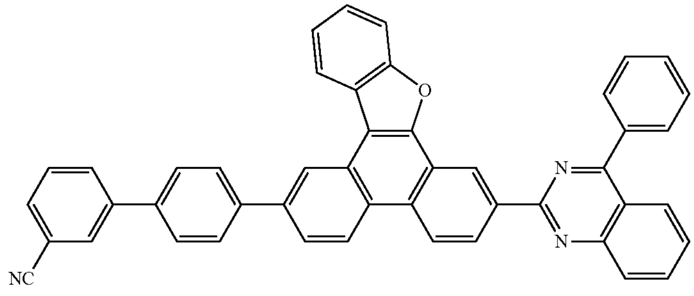

-continued
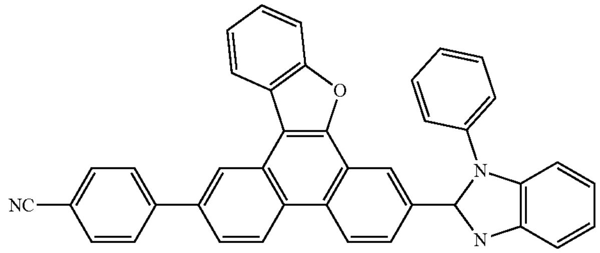
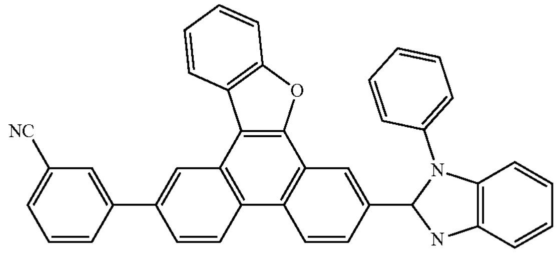
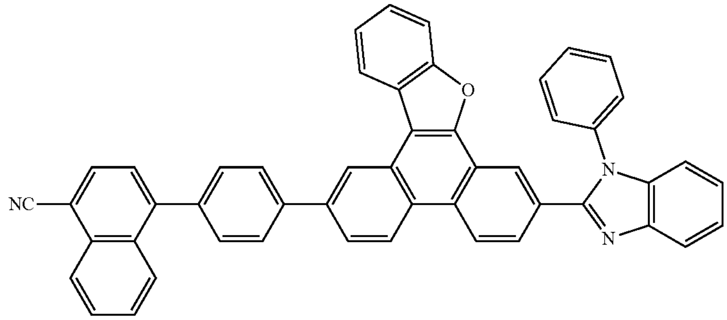
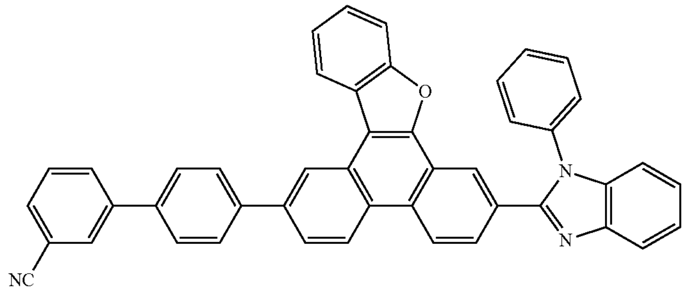
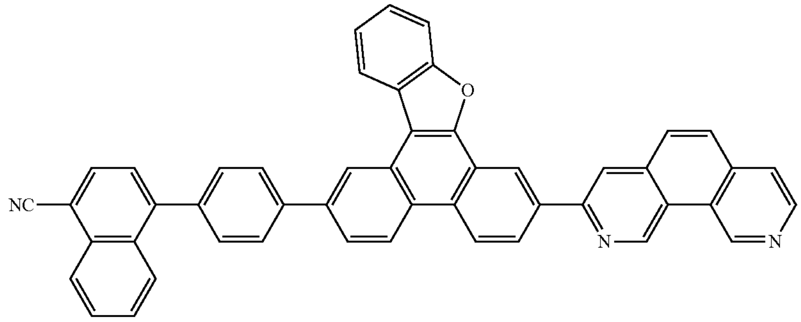

-continued
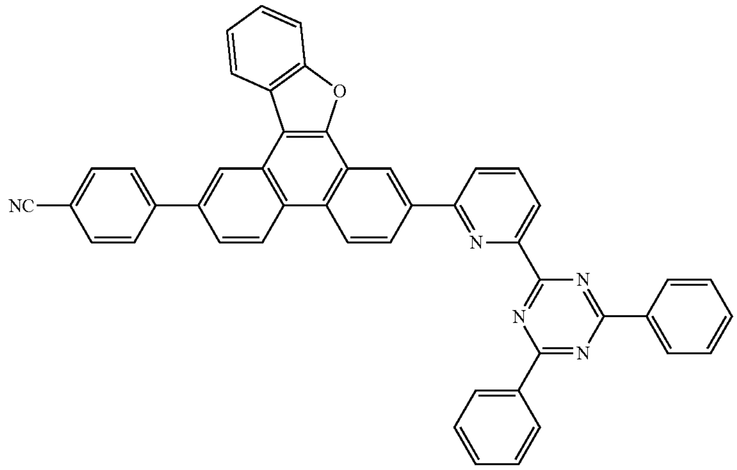
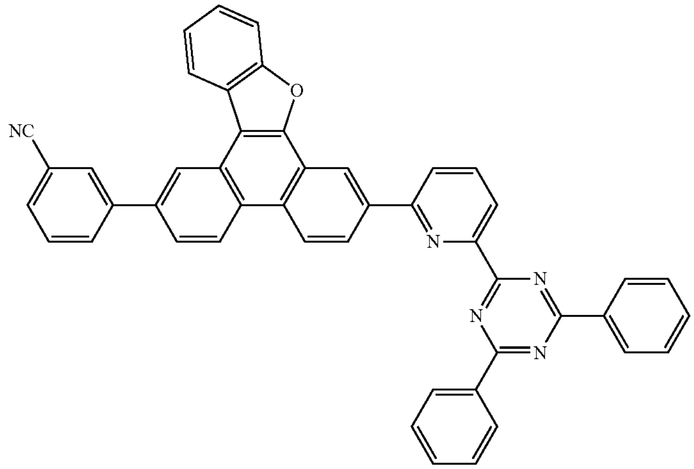
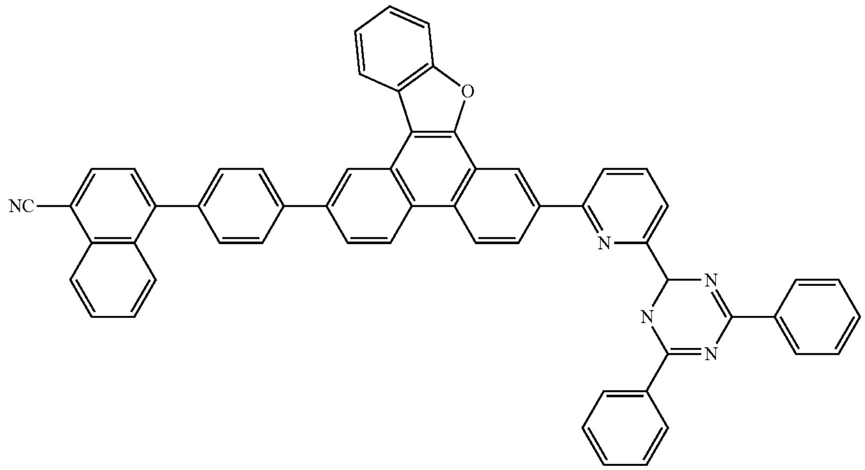

-continued
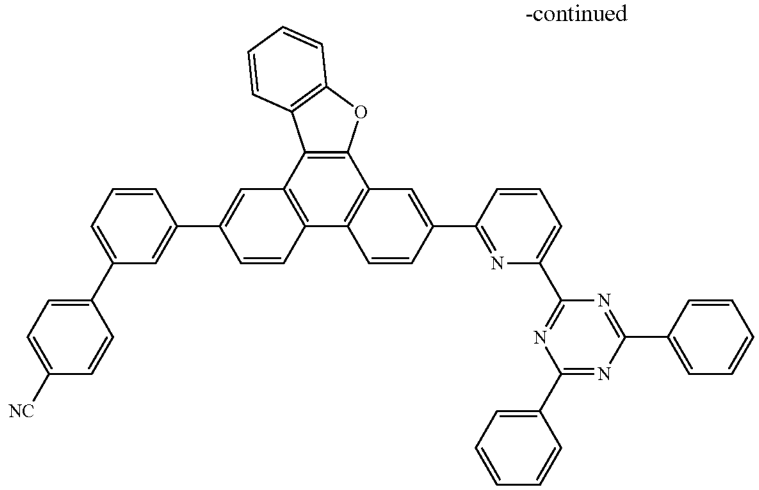
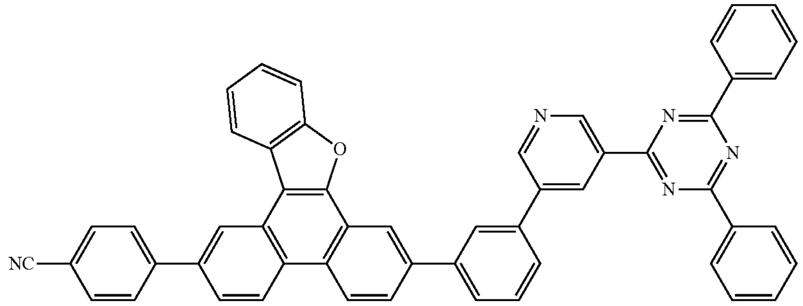
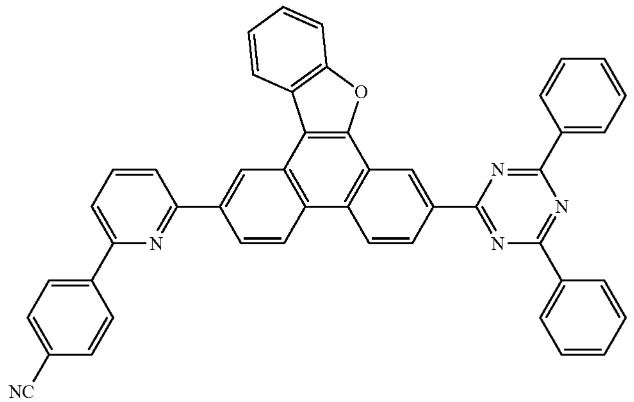
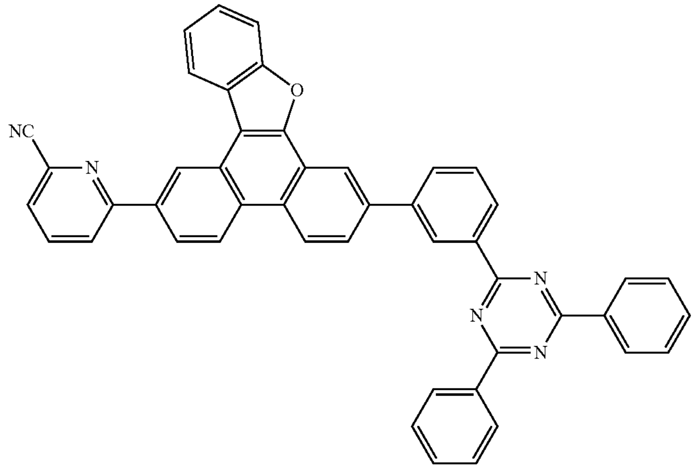

-continued
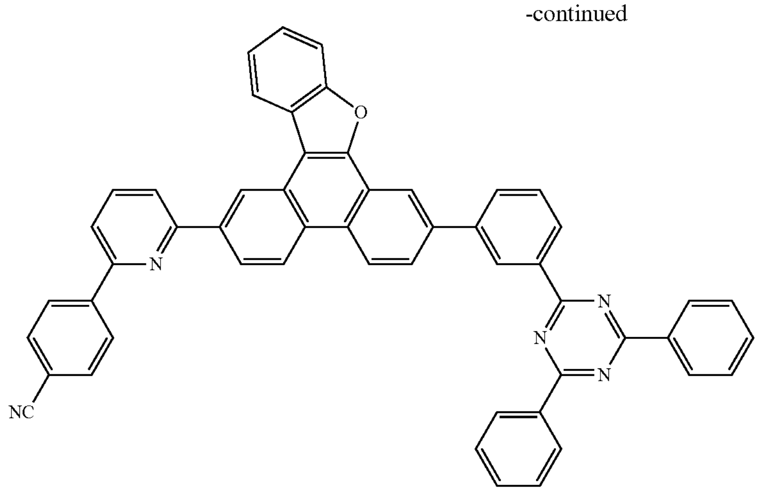
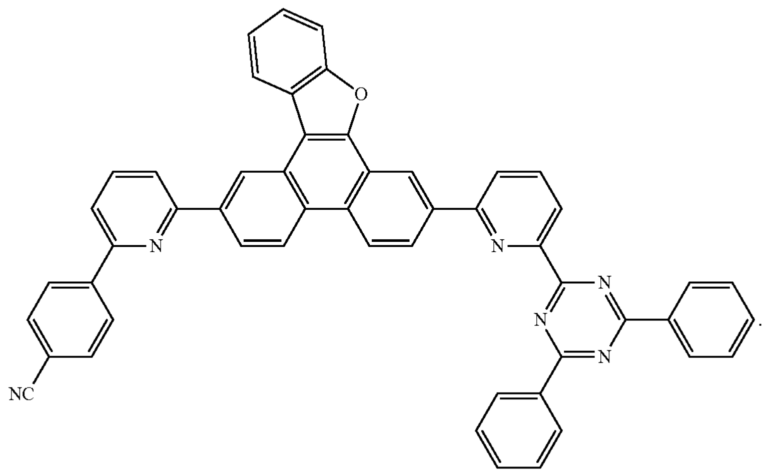
In the present disclosure, the organic compound having the structure represented by Formula I may be prepared by the following synthesis route:
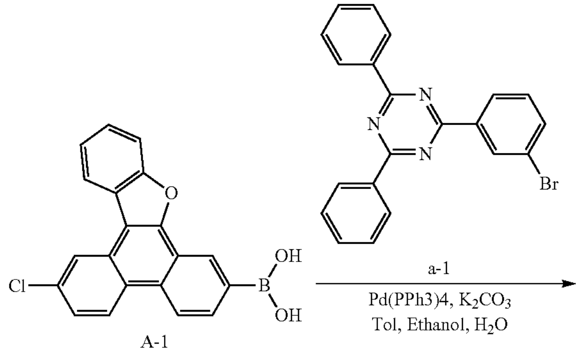
A-1
-continued
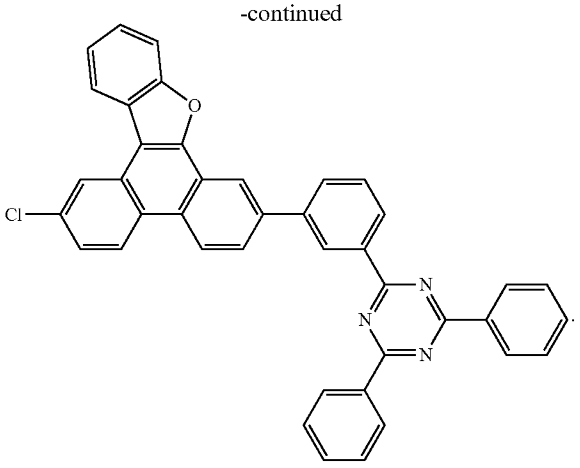
B-1

$X_1$, $X_2$, $X_3$, L, $R_1$, $R_2$, A and $n_1$ are limited within the same ranges as in Formula I, and W is selected from halogen (for example, fluorine, chlorine, bromine or iodine).

A second aspect of the present disclosure is to provide an electron transport layer material. The electron transport layer material includes the organic compound according to the first aspect.

A third aspect of the present disclosure is to provide a hole blocking layer material. The hole blocking layer material includes the organic compound according to the first aspect.

A fourth aspect of the present disclosure is to provide an OLED device. The OLED device includes an anode, a cathode and an organic thin film disposed between the anode and the cathode, wherein a material of the organic thin film includes at least one of the organic compounds each according to the first aspect.

In an embodiment, the organic thin film includes an electron transport layer, wherein a material of the electron transport layer includes at least one of the organic compounds each according to the first aspect.

In an embodiment, the organic thin film includes a hole blocking layer, wherein a material of the hole blocking layer includes the organic compound according to the first aspect.

In the OLED device provided by the present disclosure, an anode material may be a metal, a metal oxide or a conductive polymer. The metal includes copper, gold, silver, iron, chromium, nickel, manganese, palladium, platinum or the like and alloys thereof. The metal oxide includes indium tin oxide (ITO), indium zinc oxide (IZO), zinc oxide, indium gallium zinc oxide (IGZO) or the like. The conductive polymer includes polyaniline, polypyrrole, poly(3-methythiophene) or the like. In addition to the above materials that facilitate hole injection and combinations thereof, the anode material further includes known materials suitable for use as the anode.

In the OLED device, a cathode material may be a metal or a multilayer metal material. The metal includes aluminum, magnesium, silver, indium, tin, titanium or the like and alloys thereof. The multilayer metal material includes LiF/Al, $LiO_2$/Al, $BaF_2$/Al or the like. In addition to the above materials that facilitate electron injection and combinations thereof, the cathode material further includes known materials suitable for use as the cathode.

In the OLED device, the organic thin film includes at least one light-emitting layer (EML) and any one or a combination of at least two of a hole injection layer (HIL), a hole transport layer (HTL), an electron blocking layer (EBL), a hole blocking layer (HBL), an electron transport layer (ETL) or an electron injection layer (EIL), which may be disposed on two sides of the light-emitting layer. In addition to the organic compound according to the first aspect of the present disclosure, the hole/electron injection layer and the hole/electron transport layer may be a carbazole compound, an arylamine compound, a benzimidazole compound, a metallic compound or the like. A capping layer (CPL) may also be optionally disposed on the cathode of the OLED device (on a side of the cathode facing away from the anode).

As shown in the FIGURE which is a schematic diagram of the OLED device, the OLED device includes an anode 101, a cathode 102, a light-emitting layer 103 disposed between the anode 101 and the cathode 102, and a first organic thin film 104 and a second organic thin film 105 respectively disposed on two sides of the light-emitting layer 103. The first organic thin film 104 is any one or a combination of at least two of a hole injection layer (HIL), a hole transport layer (HTL) or an electron blocking layer (EBL), and the second organic thin film 105 includes any one or a combination of at least two of a hole blocking layer (HBL), an electron transport layer (ETL) or an electron injection layer (EIL). A capping layer (CPL) may also be optionally disposed on the cathode 102 (on a side of the cathode 102 facing away from 105).

The OLED device may be prepared by the following method: forming the anode on a transparent or opaque smooth substrate, forming the organic thin film layer on the anode, and forming the cathode on the organic thin film layer. The organic thin film layer may be formed by a known film formation method such as evaporation, sputtering, spin coating, impregnation and ion plating.

A fifth aspect of the present disclosure is to provide a display panel. The display panel includes the OLED device according to the fourth aspect.

A sixth aspect of the present disclosure is to provide an electronic device. The electronic device includes the display panel according to the fifth aspect.

Exemplarily, several preparation examples of the organic compounds of the present disclosure are listed below.

Preparation Examples: Preparation of Compound 1 to Compound 9

(1)

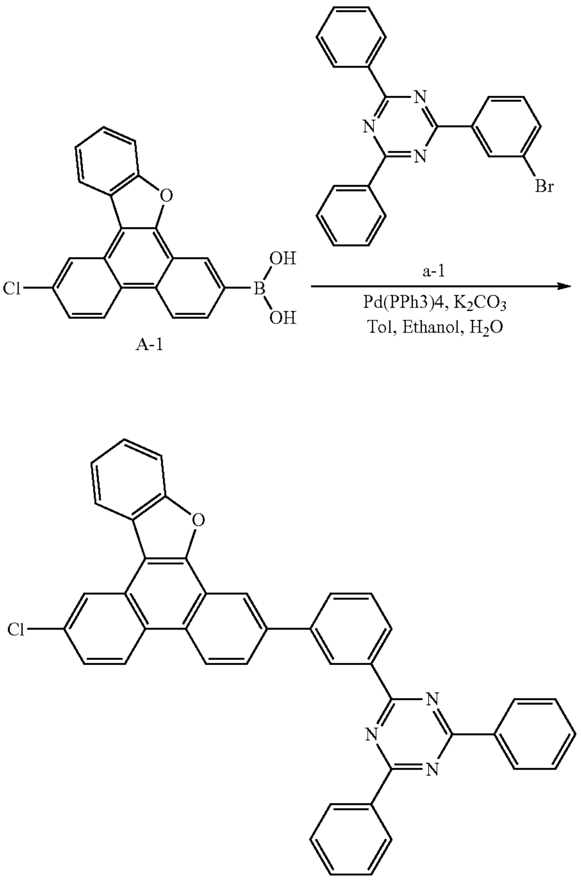

A-1

B-1

Under a nitrogen atmosphere, reaction solvents, toluene, ethanol and water were added to a reaction flask at a ratio of 7:2:1. Then, $K_2CO_3$ (10 mmol) aq, a reactant A-1 (5 mmol), a reactant a-1 (5 mmol) and $Pd(PPh_3)_4$ (0.25 mmol) were sequentially added. The system was warmed to 80° C. and reacted overnight. After the reaction was completed, the system was cooled to room temperature and extraction was performed with dichloromethane/$H_2O$. The collected organic phase was dried over anhydrous $Na_2SO_4$, suction-filtered to collect a filtrate, and subjected to rotary evaporation to remove the solvents and the residuum was purified through column chromatography to obtain an intermediate B-1 (with a yield of 75%).

MALDI-TOF (m/z): C41H24ClN3O: calculated value: 610.11; measured value: 610.32.

(2)

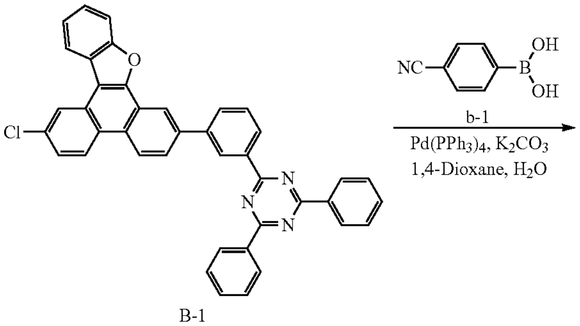

B-1

-continued

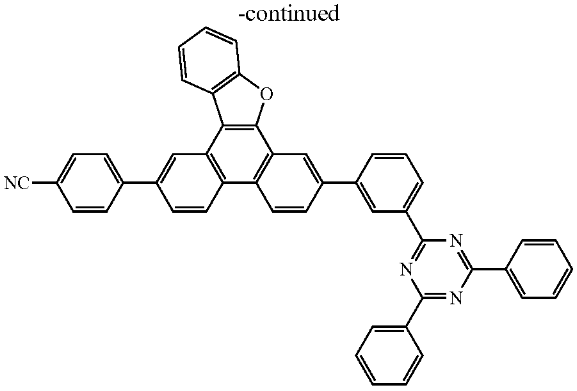

Compound 1

Under a nitrogen atmosphere, 1,4-dioxane was added to a reaction flask. Then, $K_2CO_3$ (8 mmol) aq, the intermediate B-1 (4 mmol), a reactant b-1 (4 mmol) and $Pd(PPh_3)_4$ (0.2 mmol) were sequentially added. The system was warmed to 100° C. and reacted overnight. After the reaction was completed, the system was cooled to room temperature and extraction was performed with dichloromethane/$H_2O$. The collected organic phase was dried over anhydrous $Na_2SO_4$, suction-filtered to collect a filtrate, and subjected to rotary evaporation to remove the solvents and the residuum was purified through column chromatography to obtain Compound 1 (with a yield of 69%).

MALDI-TOF (m/z): C48H28N4O: calculated value: 676.78; measured value: 676.95.

Elemental analysis (EA) (%): $C_{48}H_{28}N_4O$: calculated values: C, 85.19, H, 4.17, N, 8.28, O 2.36; measured values: C, 85.20, H, 4.16, N, 8.29, O 2.38.

The intermediates/products in Table 1 were synthesized by a method similar to the preceding method.

TABLE 1

| Raw Material/Intermediate | Raw Material/Intermediate |
|---|---|
| 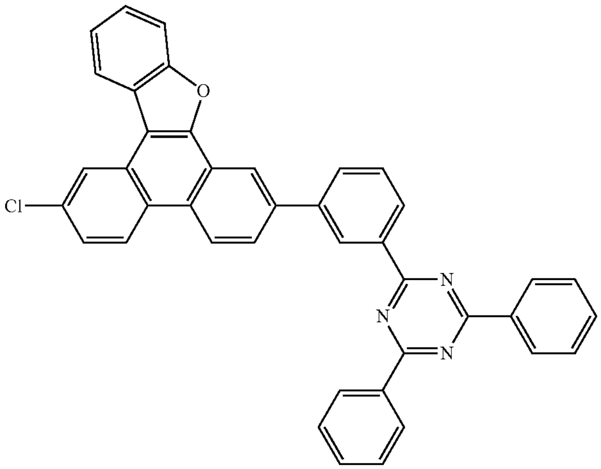 B-1 | 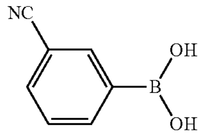 b-2 |

TABLE 1-continued
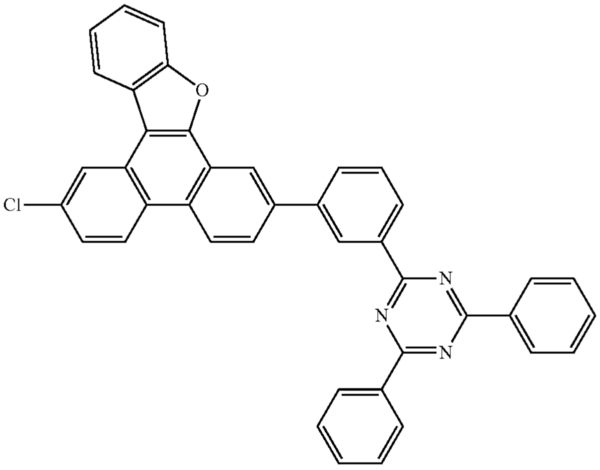
B-1
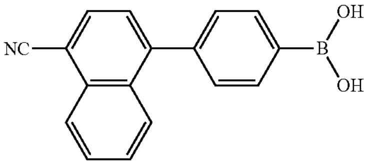
b-3
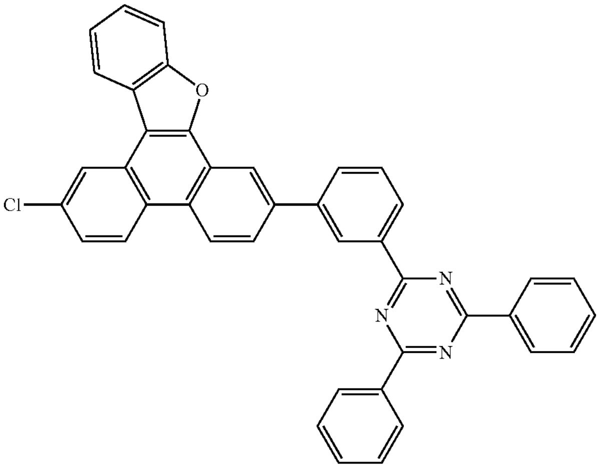
B-1
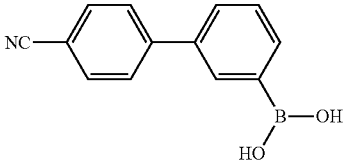
b-4
| Intermediate/Product | Yield (%) | (1) MALDI-TOF (m/z) (2) EA (%) |
|---|---|---|
| 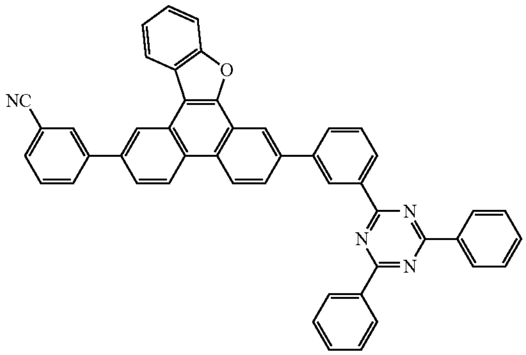 Compound 2 | 71 | C48H28N4O: (1) calculated value: 676.78; measured value: 676.99 (2) calculated values: C 85.19, H 4.17, N 8.28, O 2.36; measured values: C 85.20, H 4.16, N 8.29, O 2.37. |

TABLE 1-continued

| | | |
|---|---|---|
| 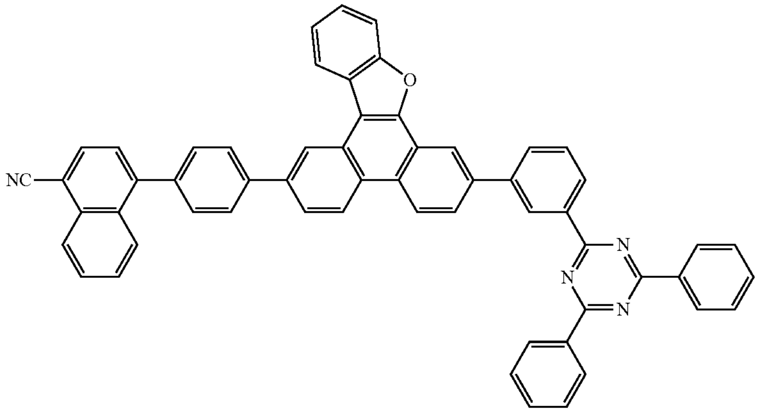<br>Compound 3 | 73 | C58H34N4O: (1) calculated value: 802.93; measured value: 802.97 (2) calculated values: C 86.76, H 4.27, N 6.98, O 1.99; measured values: C 86.77, H 4.26, N 6.99, O 1.97. |
| 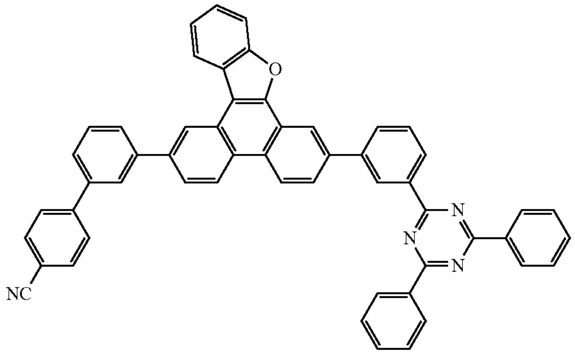<br>Compound 4 | 74 | C54H32N4O: (1) calculated value: 752.87; measured value: 752.95 (2) calculated values: C 86.15, H 4.28, N 7.44, O 2.13; measured values: C 86.16, H 4.27, N 7.46, O 2.12. |

The intermediates/products in Table 2 were synthesized by a method similar to the preceding method.

TABLE 2

| Reaction 1 | | Reaction 2 |
|---|---|---|
| Raw Material 1 | Raw Material 2 | Raw Material 3 |
| 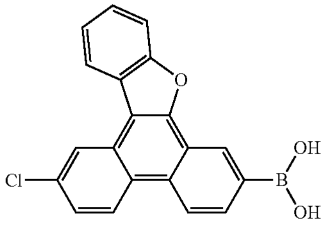<br>A-1 | 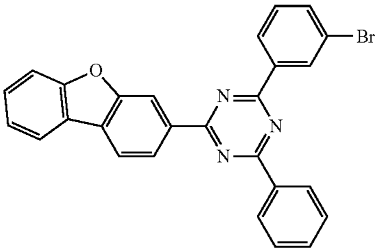<br>a-2 | 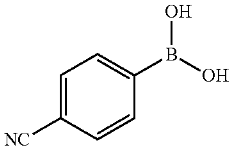<br>b-1 |
| 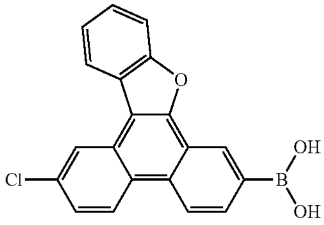<br>A-1 | 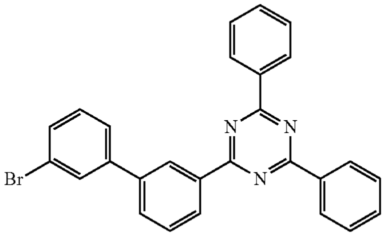<br>a-3 | 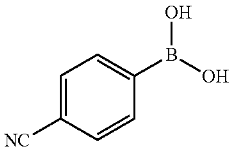<br>b-1 |

TABLE 2-continued
| | | |
|---|---|---|
| 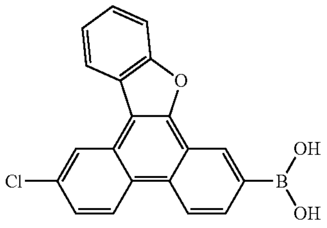 A-1 | 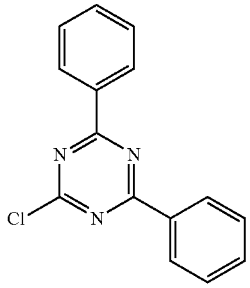 a-4 | 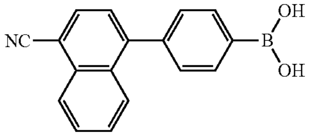 b-3 |
| 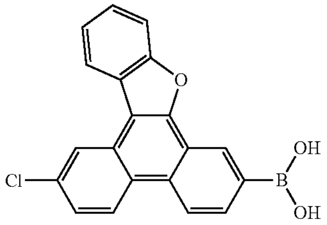 A-1 | 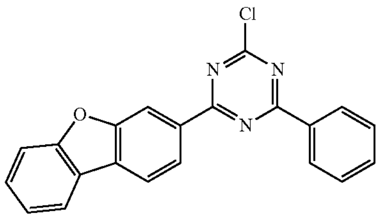 a-5 | 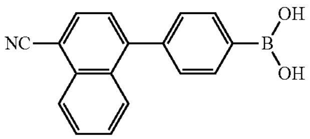 b-3 |
| 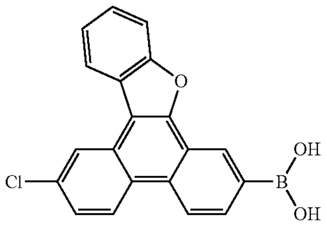 A-1 | 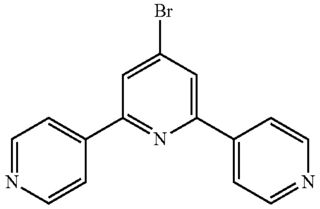 a-6 | 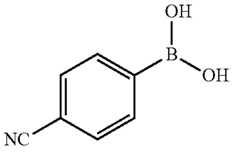 b-1 |
Reaction 2
| Intermediate/Product | Yield (%) | (1) MALDI-TOF (m/z) (2) EA (%) |
|---|---|---|
| 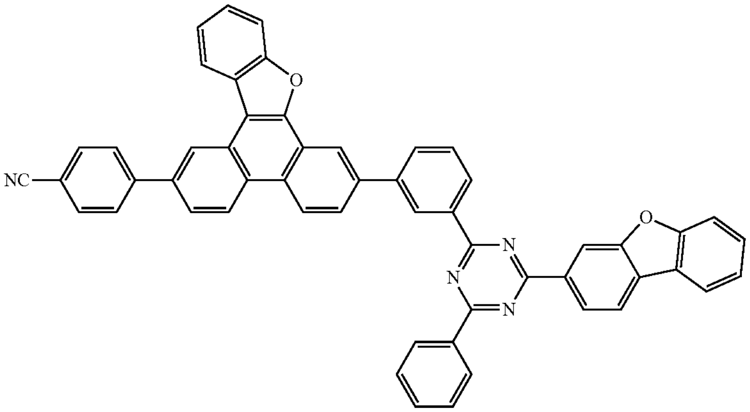 Compound 5 | 72 | C54H30N4O2: (1) calculated value: 766.86; measured value: 766.98 (2) calculated values: C 84.58, H 3.94, N 7.31, O 4.17; measured values: C 84.59, H 3.93, N 7.33, O 4.16. |

TABLE 2-continued

| | | |
|---|---|---|
| 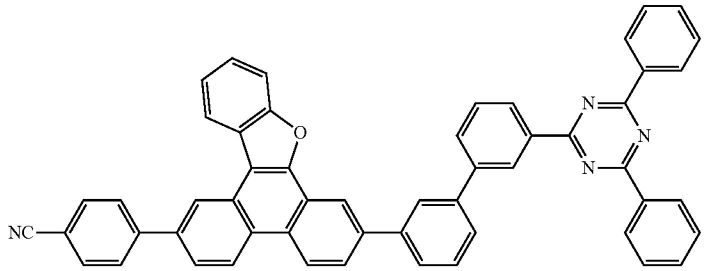 Compound 6 | 71 | C54H32N4O: (1) calculated value: 752.87; measured value: 752.96 (2) calculated values: C 86.15, H 4.28, N 7.44, O 2.13; measured values: C 86.16, H 4.27, N 7.46, O 2.12. |
| 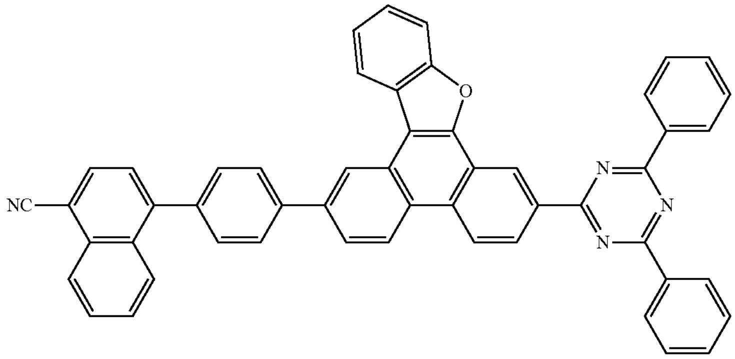 Compound 7 | 73 | C52H30N4O: (1) calculated value: 726.84; measured value: 726.98 (2) calculated values: C 85.93, H 4.16, N 7.71, O 2.20; measured values: C 85.94, H 4.15, N 7.74, O 2.19. |
| 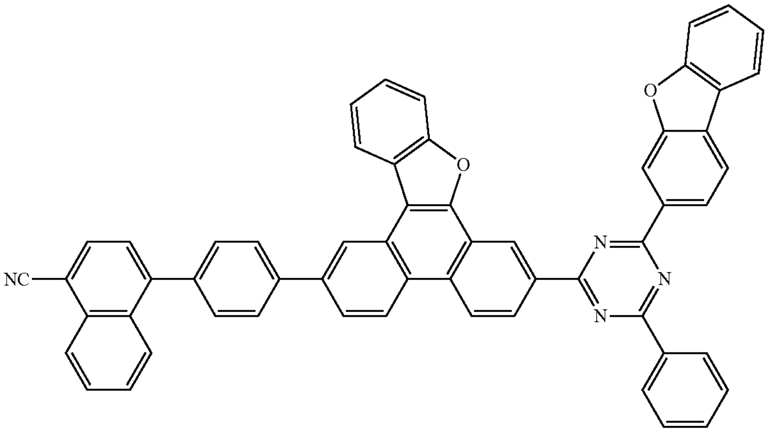 Compound 8 | 75 | C58H32N4O2: (1) calculated value: 816.92; measured value: 816.99 (2) calculated values: C 85.28, H 3.95, N 6.86, O 3.92; measured values: C 85.29, H 3.94, N 6.88, O 3.91. |
| 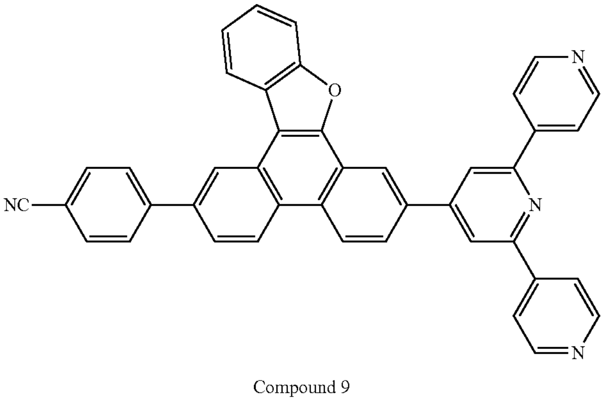 [SMILES: N#Cc1ccc(-c2ccc3c4ccc(-c5cc(-c6ccncc6)nc(-c6ccncc6)c5)cc4c4oc5ccccc5c4c3c2)cc1] Compound 9 | 70 | C42H24N4O: (1) calculated value: 600.68; measured value: 600.92 (2) calculated values: C 83.98, H 4.03, N 9.33, O 2.66; measured values: C 83.99, H 4.02, N 9.36, O 2.65. |

Simulated Calculations of Energy Levels of Compounds

By use of a density-functional theory (DFT), for the organic compounds provided in the examples of the present disclosure, the distribution of molecular frontier orbitals (HOMO and LUMO) was optimized and calculated by using a Gaussian 09 package (Gaussian Inc.) at a calculation level of B3LYP/6-31G(d). Moreover, a lowest singlet energy level Si and a lowest triplet energy level Ti of a molecule of the compound were simulated and calculated based on a time-dependent density-functional theory (TD-DFT). The results are shown in Table 3.

TABLE 3

| Compound | HOMO (eV) | LUMO (eV) | $E_{S1}$ (eV) | $E_{T1}$ (eV) |
|---|---|---|---|---|
| Compound 1 | −5.78 | −2.04 | 3.19 | 2.50 |
| Compound 2 | −5.78 | −2.03 | 3.20 | 2.50 |
| Compound 3 | −5.72 | −2.07 | 3.18 | 2.49 |
| Compound 4 | −5.80 | −2.02 | 3.21 | 2.50 |
| Compound 5 | −5.77 | −2.01 | 3.20 | 2.49 |
| Compound 6 | −5.70 | −2.00 | 3.23 | 2.51 |
| Compound 7 | −5.70 | −1.98 | 3.21 | 2.49 |
| Compound 8 | −5.70 | −1.99 | 3.20 | 2.49 |
| Compound 9 | −5.65 | −1.91 | 3.20 | 2.50 |

As can be seen from Table 3, the compounds provided by the present disclosure each have a relatively deep LUMO energy level (−1.91 to −2.07 eV), which may reduce a potential barrier of electron transport, improve an electron injection capability and effectively reduce a voltage of an OLED device. The compounds each have a relatively deep HOMO energy level (−5.65 to −5.80 eV), which may effectively block holes so that more holes and electrons are recombined in a light-emitting region, achieving relatively high luminescence efficiency.

Several application examples of the organic compounds of the present disclosure applied to OLED devices are listed below.

Application Example 1

The present application example provides an OLED device whose structure is shown in the FIGURE. The OLED device includes a substrate 1, an anode 2, a hole injection layer 3, a hole transport layer 4, an electron blocking layer 5, a light-emitting layer 6, a hole blocking layer 7, an electron transport layer 8, an electron injection layer 9 and a cathode 10 which are stacked in sequence. An arrow in the FIGURE represents a direction of light emission of the device.

The above OLED device is prepared through specific steps described below.

(1) A glass substrate 1 with an indium tin oxide (ITO) anode 2 (with a thickness of 100 nm) was sonicated in isopropanol and deionized water for 30 min, separately and cleaned under ozone for about 10 min. The cleaned glass substrate 1 was installed onto a vacuum deposition device.

(2) Compound a was deposited by means of vacuum evaporation on the ITO anode 2 as a hole injection layer 3 with a thickness of 10 nm.

(3) Compound b was deposited by means of vacuum evaporation on the hole injection layer 3 as a hole transport layer 4 with a thickness of 40 nm.

(4) Compound c was deposited by means of vacuum evaporation on the hole transport layer 4 as an electron blocking layer 5 with a thickness of 10 nm.

(5) Compound d and Compound e were co-deposited at a doping ratio of 5% (mass ratio) by means of vacuum evaporation on the electron blocking layer 5 as a light-emitting layer 6 with a thickness of 20 nm.

(6) Compound f was deposited by means of vacuum evaporation on the light-emitting layer 6 as a hole blocking layer 7 with a thickness of 10 nm.

(7) Compound 1 provided in Preparation Example 1 was deposited by means of vacuum evaporation on the hole blocking layer 7 as an electron transport layer 8 with a thickness of 30 nm.

(8) Compound LiF was deposited by means of vacuum evaporation on the electron transport layer 8 as an electron injection layer 9 with a thickness of 2 nm.

(9) An aluminum electrode was deposited by means of vacuum evaporation on the electron injection layer 9 as a cathode 10 with a thickness of 100 nm.

The compounds used for preparing the above OLED device are as follows:

Compound a

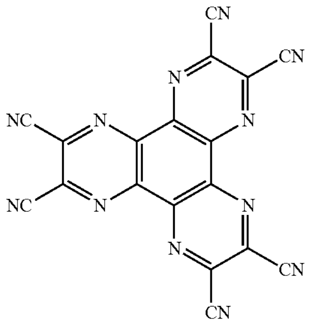

Compound b

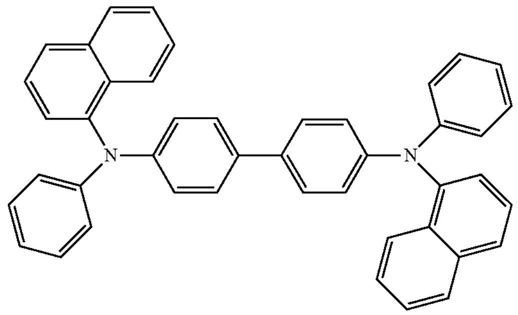

Compound c

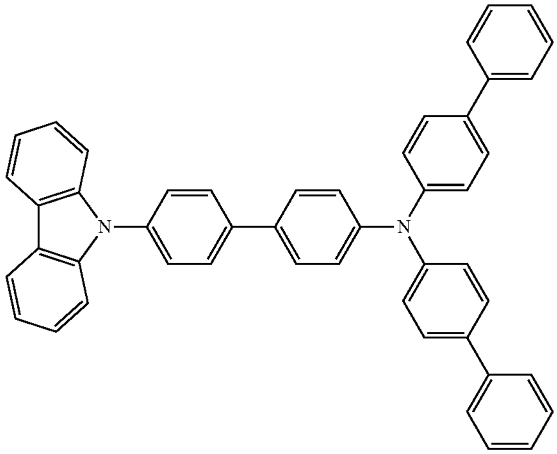

-continued

Compound d

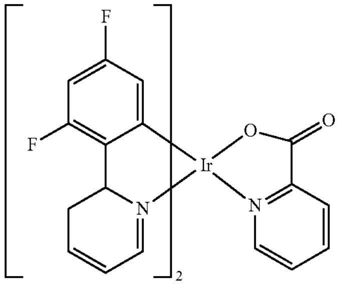

Compound e

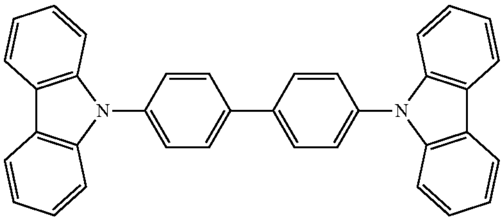

Compound f

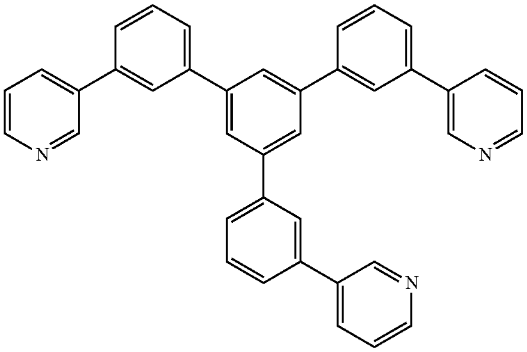

Comparative Compound 1

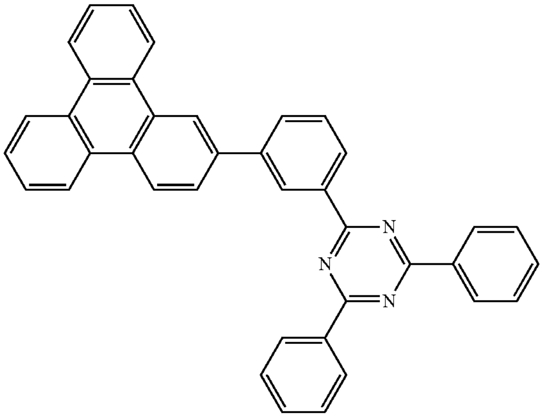

-continued

Comparative Compound 2

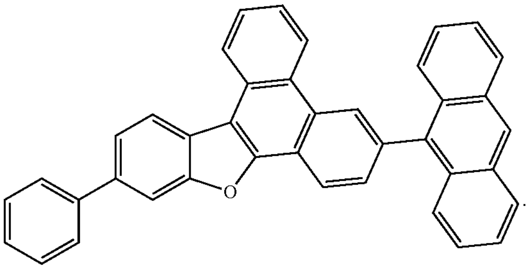

Application Examples 2 to 9 and Comparative Examples 1 and 2

Each of Application Examples 2 to 9 and Comparative Examples 1 and 2 differs from Application Example 1 only in that Compound 1 in step (7) was replaced with a respective compound shown in Table 3.

Performance Evaluation of OLED Devices

According to the current densities and brightness of the OLED device at different voltages, a working voltage V and current efficiency CE (cd/A) at a certain current density (10 mA/cm$^2$) were obtained. A lifetime LT95 (h) was obtained by measuring the time taken for the OLED device to reach 95% of initial brightness (under a condition of 50 mA/cm$^2$). The test data are shown in Table 4.

TABLE 4

| OLED Device | Electron Transport Layer | V (V) | CE (cd/A) | LT95 (h) |
|---|---|---|---|---|
| Application Example 1 | Compound 1 | 3.89 | 16.3 | 83 |
| Application Example 2 | Compound 2 | 3.89 | 16.4 | 82 |
| Application Example 3 | Compound 3 | 3.85 | 16.5 | 85 |
| Application Example 4 | Compound 4 | 3.90 | 15.9 | 78 |
| Application Example 5 | Compound 5 | 3.93 | 15.6 | 76 |
| Application Example 6 | Compound 6 | 3.93 | 15.4 | 75 |
| Application Example 7 | Compound 7 | 3.98 | 15.5 | 73 |
| Application Example 8 | Compound 8 | 4.00 | 15.3 | 70 |
| Application Example 9 | Compound 9 | 4.08 | 15.1 | 67 |
| Comparative Example 1 | Comparative Compound 1 | 4.18 | 14.6 | 59 |
| Comparative Example 2 | Comparative Compound 2 | 7.54 | 3.6 | 0.5 |

As can be seen from Table 4, the OLED devices provided by Examples 1 to 9 of the present disclosure each have a relatively low drive voltage, relatively high luminescence efficiency and a relatively long lifetime, where the working voltage is ≤4.08 V, the current efficiency (CE) is ≥15.1 cd/A and the lifetime LT95 is ≥67 h. Compared with Comparative Example 1, Examples 1 to 9 using the compounds of the present disclosure each have a reduced working voltage, improved efficiency and an extended lifetime, which may result from a relatively deep LUMO energy level of Compound 1 to Compound 9 of the present disclosure so that the electron injection is easy and the working voltage of the device is reduced. Moreover, the compound has a relatively deep HOMO value, which may effectively block holes so that the holes are confined in a light-emitting region and recombined with electrons, being conducive to widening a light-emitting recombination region and improving the luminescence efficiency of the device. Moreover, the organic compound provided by the present disclosure has good thermal stability and film forming ability, which is conducive to the stability of the device and extending the lifetime of the device. Even if the compound of the present disclosure, which is used by the OLED device in Example 9, does not have a deep LUMO energy level, the compound still has a better electron injection capability than the compound in Comparative Example 1 so that more holes and electrons are recombined, thereby improving the efficiency of the device.

In particular, it is to be noted that both sides of the structure in Comparative Example 2 were merely made up of carbon atoms. A lack of an efficient electron transport structure results in very poor electron injection and transport capabilities. Therefore, the preceding device data shows a significant increase in voltage. Moreover, the really poor electron transport capability causes carriers in the structure of the device to seriously deviate from an equilibrium state, resulting in relatively low device efficiency and a relatively short lifetime. This further indicates the necessity and rationality of the requirement that "$X_1$ to $X_3$ are independently selected from a C atom or a N atom, and at least one of $X_1$ to $X_3$ is N" in the present disclosure.

The applicant states that although the organic compound and the application thereof of the present disclosure are described through the preceding examples, the present disclosure is not limited to the preceding examples, which means that the implementation of the present disclosure does not necessarily depend on the preceding examples. Those skilled in the art are to understand that any improvements made to the present disclosure, equivalent substitutions of raw materials of products, additions of adjuvant ingredients, selections of specific manners or the like in the present disclosure all fall within the protection scope and the disclosure scope of the present disclosure.

What is claimed is:

1. An organic compound having a structure represented by Formula I:

Formula I

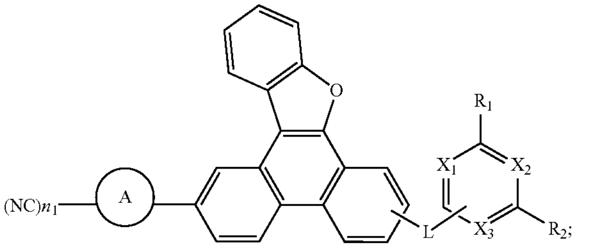

wherein the ring A is any one of phenylene, biphenylene, naphthylene, terphenylene, pyridinylene or phenylene-naphthylene;

wherein L is selected from a single bond, substituted or unsubstituted C6-C30 aryl, or substituted or unsubstituted C5-C30 heteroaryl;

wherein $X_1$ to $X_3$ are independently selected from a C atom or a N atom, and at least one of $X_1$ to $X_3$ is N;

wherein $R_1$ and $R_2$ are independently selected from substituted or unsubstituted C6-C30 aryl, or substituted or unsubstituted C5-C30 heteroaryl; and wherein $n_1$ is an integer from 1 to 3.

2. The organic compound according to claim 1, wherein the organic compound has a structure represented by Formula II:

Formula II

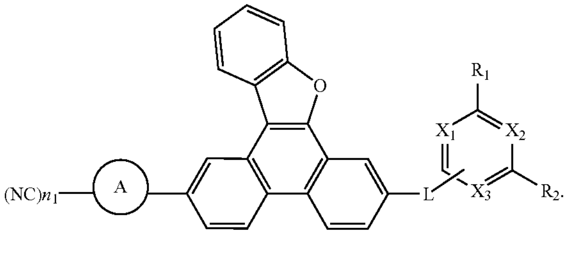

3. The organic compound according to claim 1, wherein when substituted or unsubstituted C6-C30 aryl or substituted or unsubstituted C5-C30 heteroaryl contains a substituent, the substituent is selected from at least one of deuterium, cyano, halogen, unsubstituted or halogenated C1-C10 linear or branched alkyl, unsubstituted or halogenated C1-C10 alkoxy, C1-C10 alkylthio, C6-C20 aryl, C5-C20 heteroaryl or C6-C18 arylamine.

4. The organic compound according to claim 1, wherein L is selected from any one of a single bond, phenylene, biphenylene, naphthylene, terphenylene, or pyridinylene.

5. The organic compound according to claim 1, wherein two of $X_1$ to $X_3$ are N or each of $X_1$ to $X_3$ is N.

6. The organic compound according to claim 1, wherein $R_1$ and $R_2$ are independently selected from any one of the following groups:

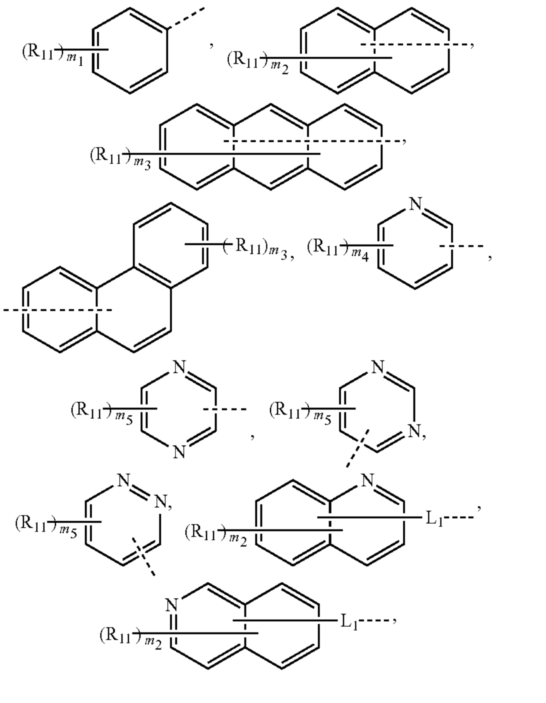

-continued

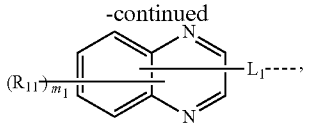
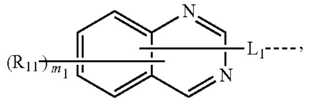
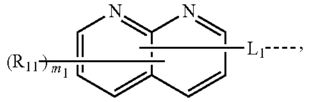
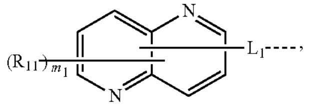
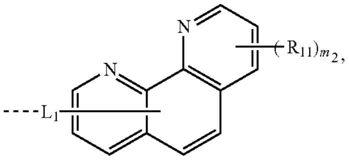
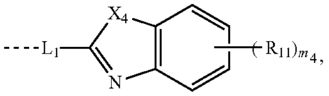
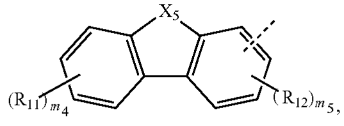
and
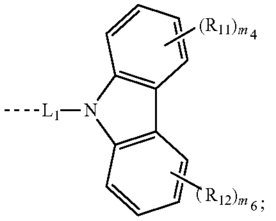

wherein the dashed line represents a linkage site of the group;

wherein $L_1$ is selected from any one of a single bond or substituted or unsubstituted C6-C20 arylene;

wherein $X_4$ is selected from O, S or $NR_{N1}$;

wherein $X_5$ is selected from O, S, $NR_{N2}$ or $CR_{C3}R_{C4}$;

wherein $R_{N1}$, $R_{N2}$, $R_{C3}$ and $R_{C4}$ are each independently selected from any one of hydrogen, substituted or unsubstituted C1-C20 linear or branched alkyl, substituted or unsubstituted C6-C20 aryl, or substituted or unsubstituted C5-C20 heteroaryl;

wherein $R_{11}$ and $R_{12}$ are each independently selected from any one of deuterium, cyano, halogen, unsubstituted or halogenated C1-C10 linear or branched alkyl, unsubstituted or halogenated C1-C10 alkoxy, C1-C10 alkylthio, C6-C20 aryl, C5-C20 heteroaryl or C6-C18 arylamine;

wherein $m_1$ is selected from an integer from 0 to 5;

wherein $m_2$ is selected from an integer from 0 to 6;

wherein $m_3$ is selected from an integer from 0 to 9;

wherein $m_4$ and $m_6$ are each independently selected from an integer from 0 to 4; and wherein $m_5$ is selected from an integer from 0 to 3.

7. The organic compound according to claim 6, wherein $R_1$ and $R_2$ are independently selected from any one of the following groups, or any one of the following groups substituted with a substituent:

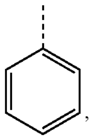,
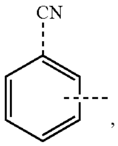,
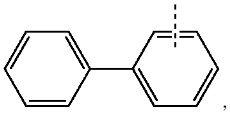,
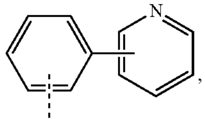,
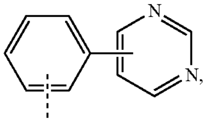
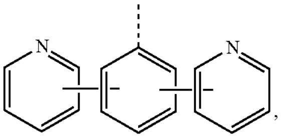
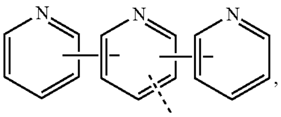
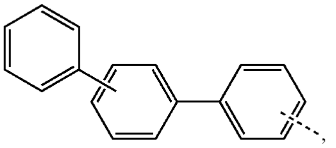
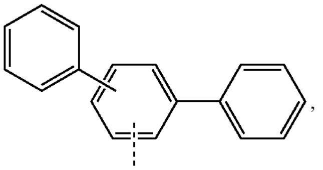,
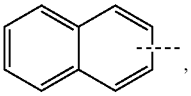
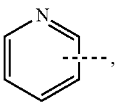,
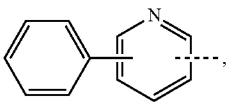
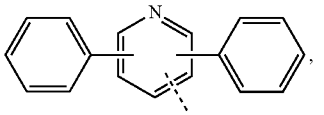,
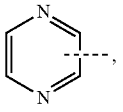
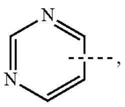,
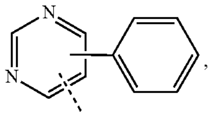
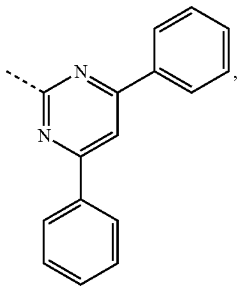,
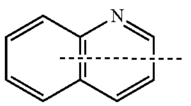
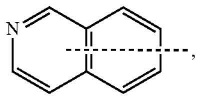,
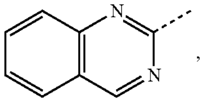, -continued

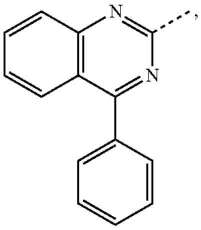, 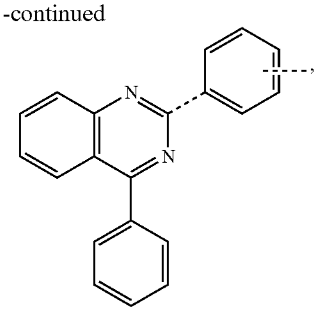, 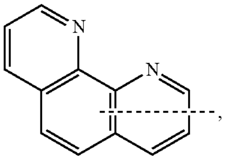, 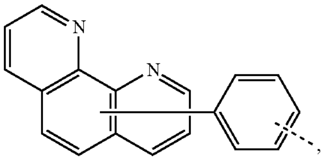, 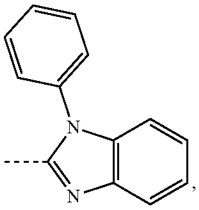, 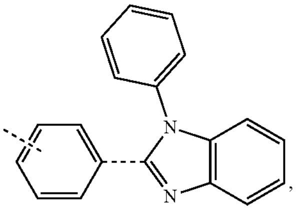, 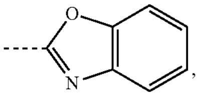, 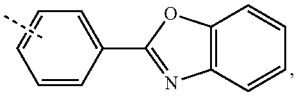, 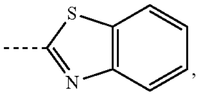, 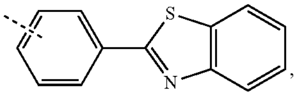, 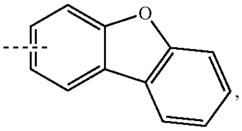, 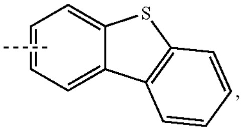, -continued

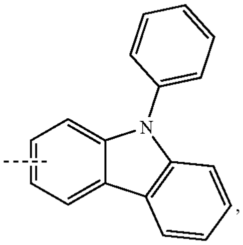, 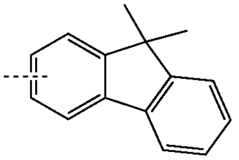, 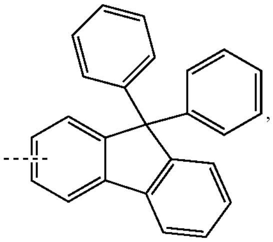, 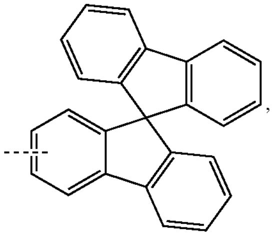, and 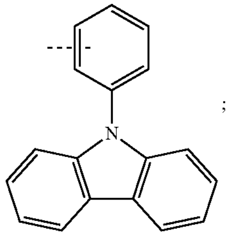;

wherein the dashed line represents a linkage site of the group; and wherein the substituted substituents are each independently selected from at least one of deuterium, cyano, halogen, unsubstituted or halogenated C1-C10 linear or branched alkyl, unsubstituted or halogenated C1-C10 alkoxy, C1-C10 alkylthio, C6-C20 aryl, C2-C20 heteroaryl or C6-C18 arylamine.

8. The organic compound according to claim 1, wherein the organic compound is selected from any one of the following compounds:

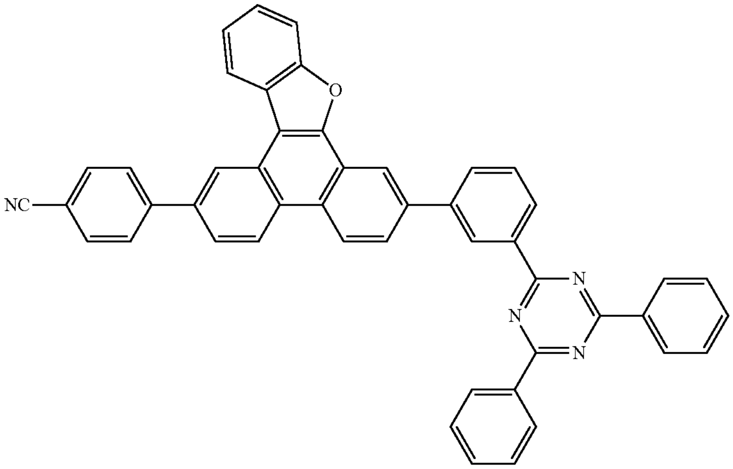

-continued
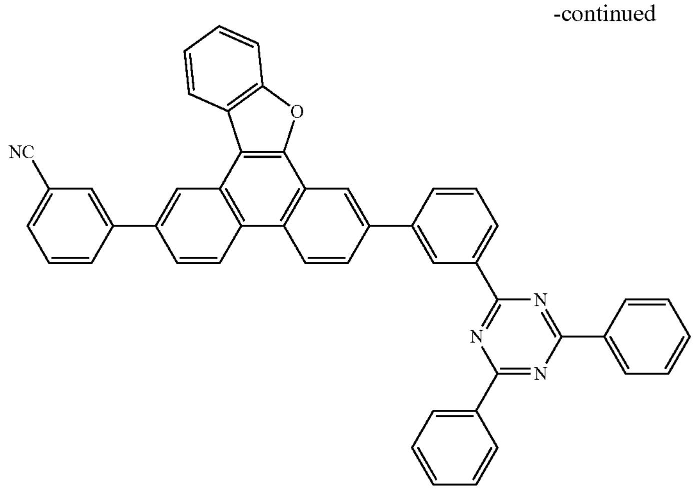
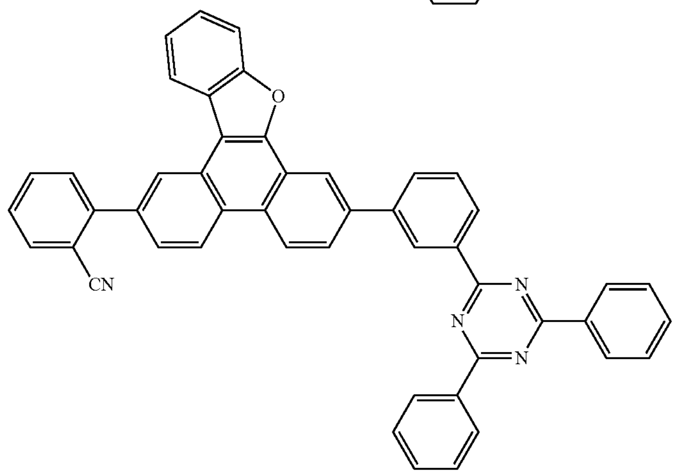
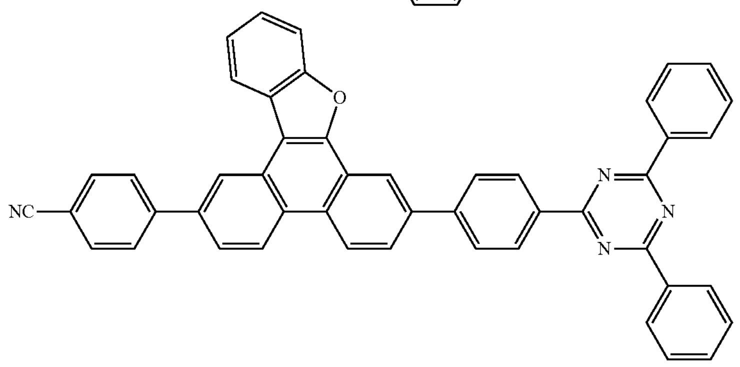
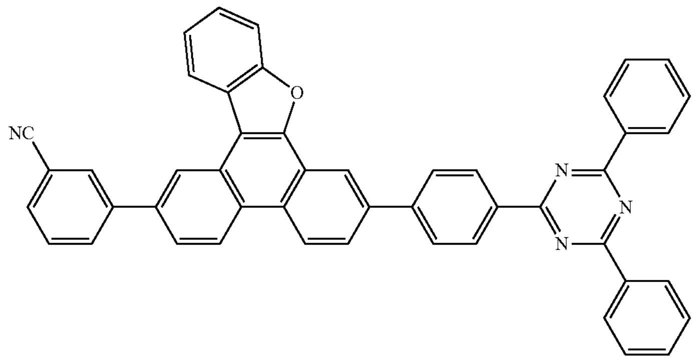

-continued
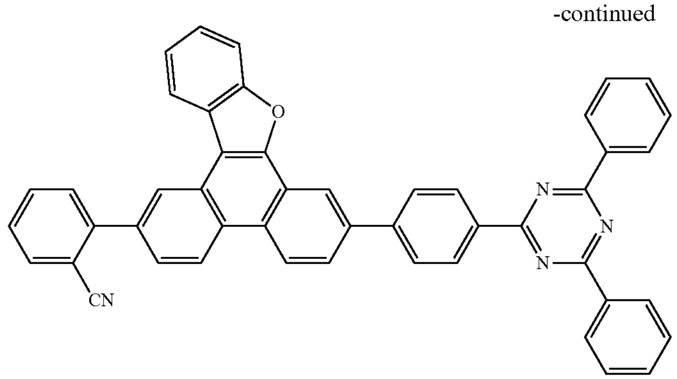
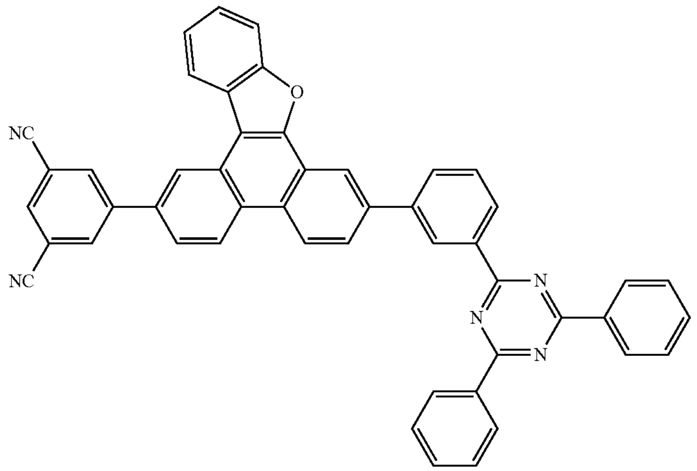
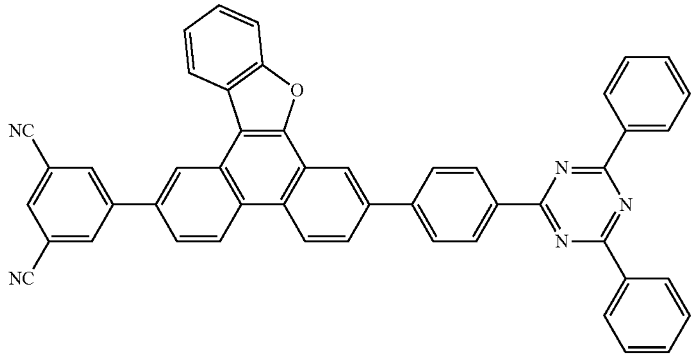
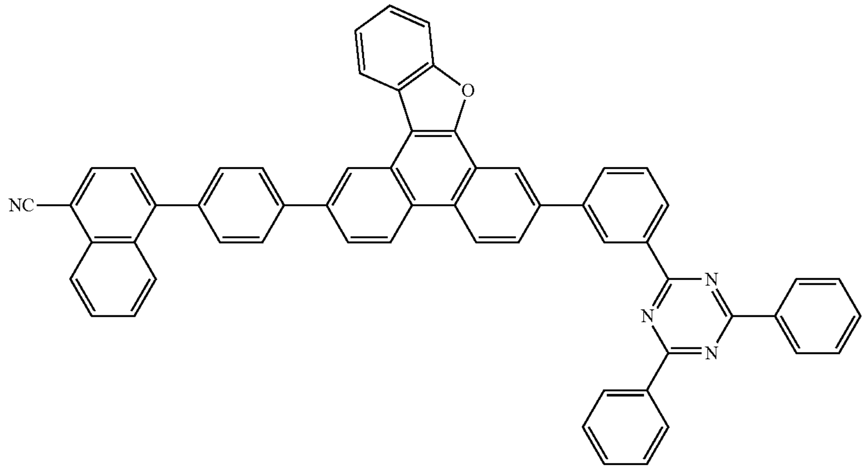

-continued
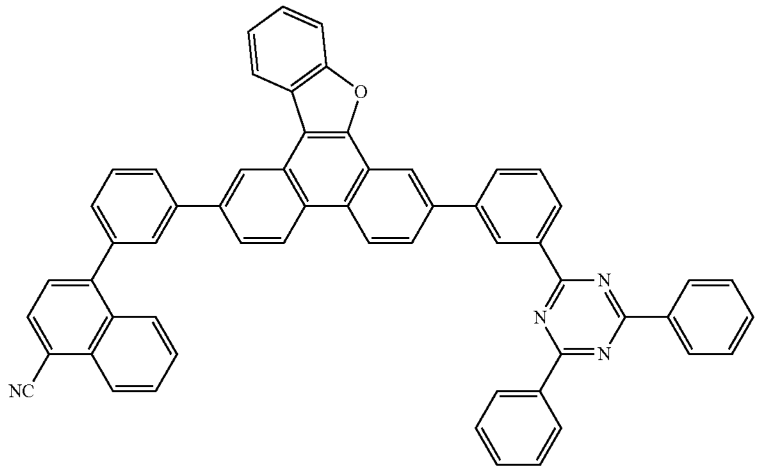
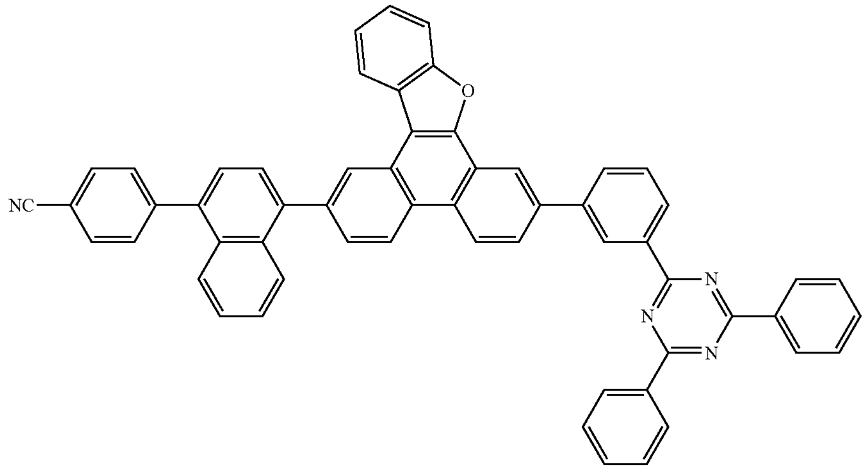
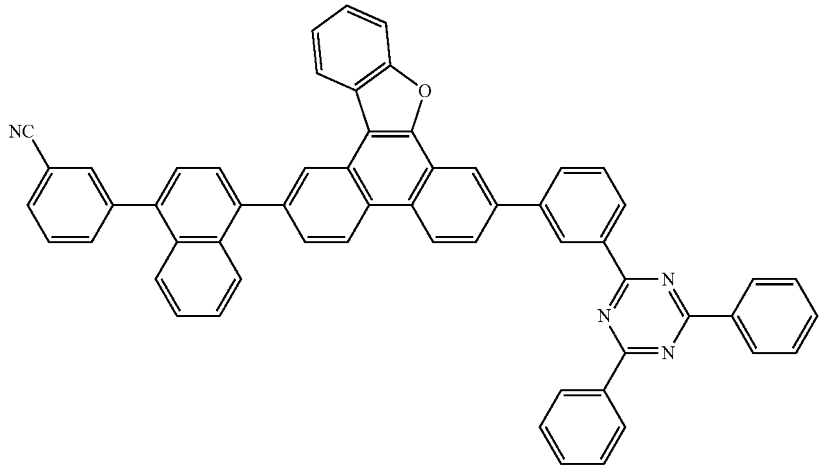

-continued
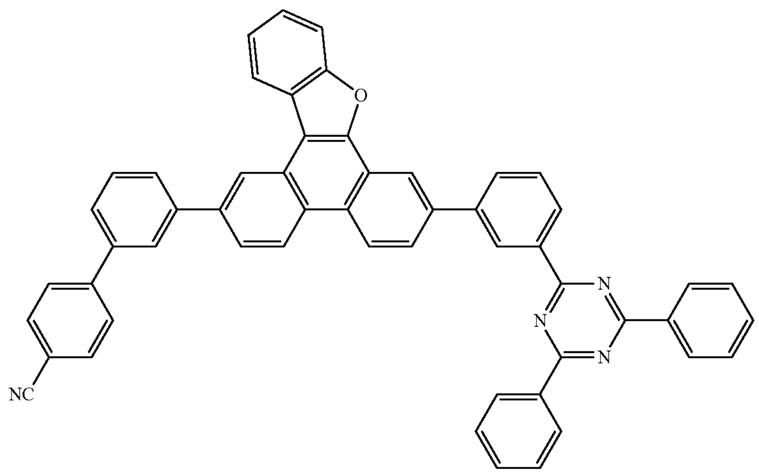
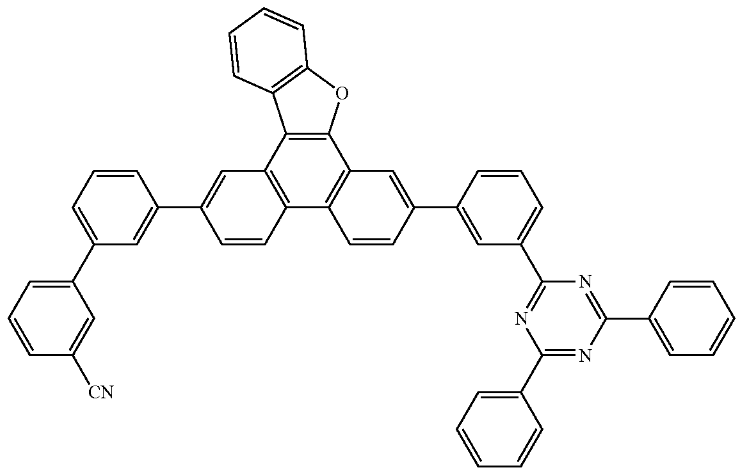
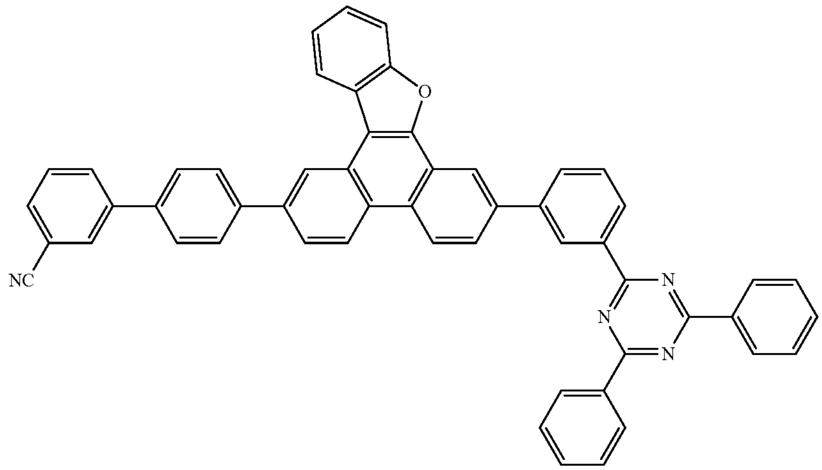

-continued
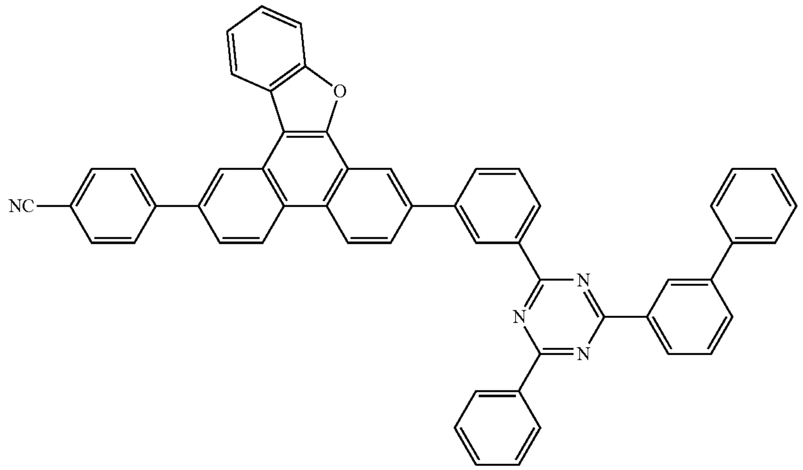
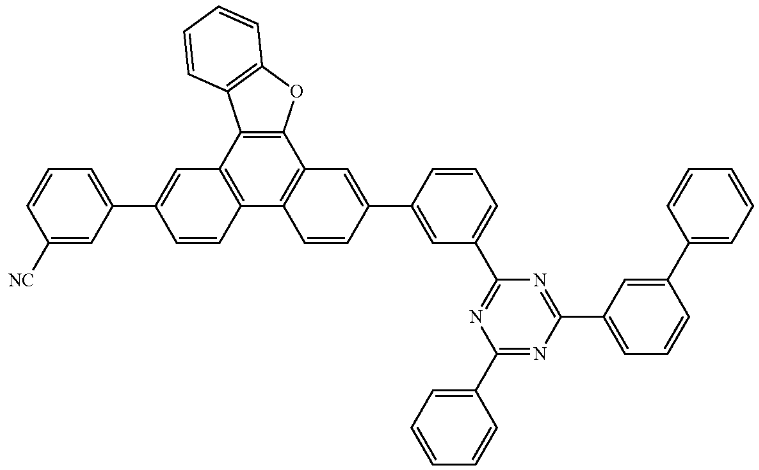
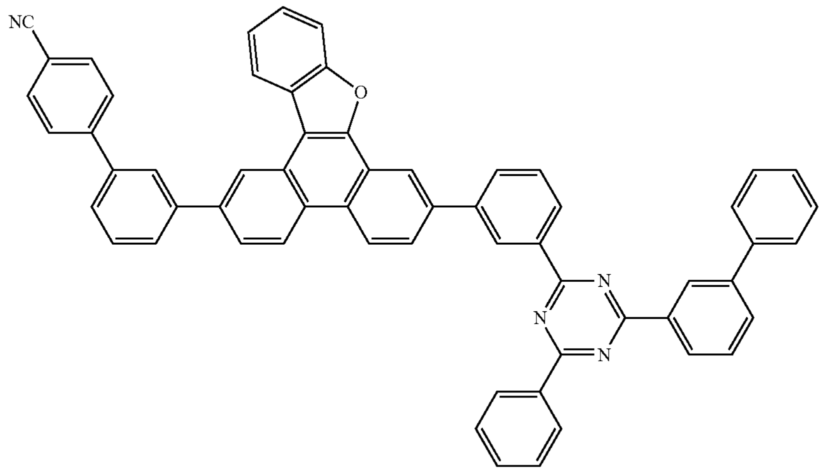

-continued
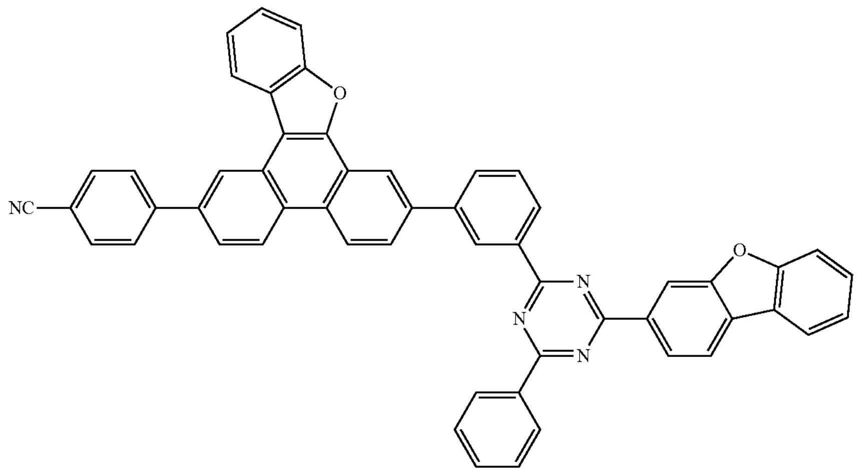
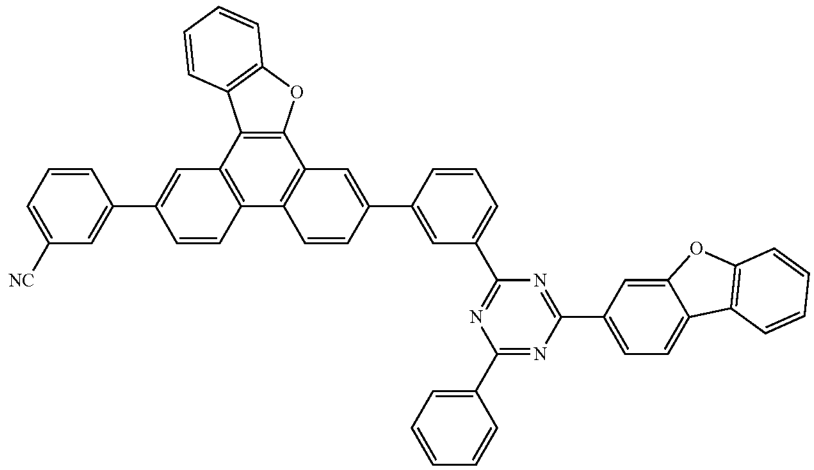
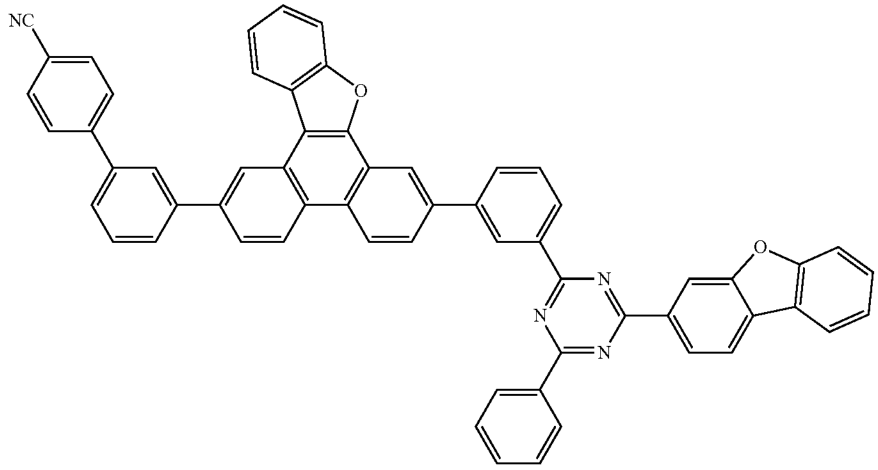

-continued
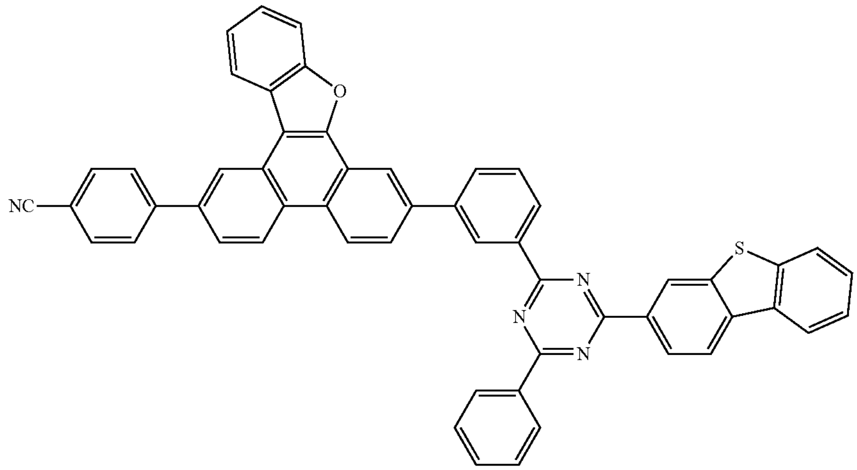
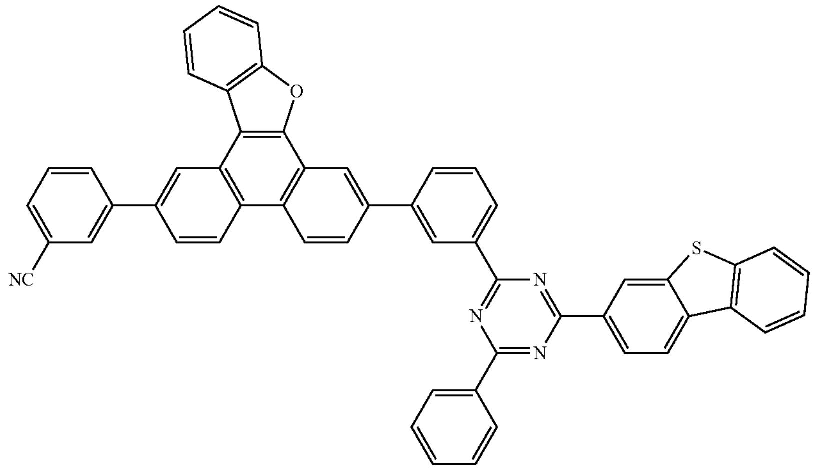
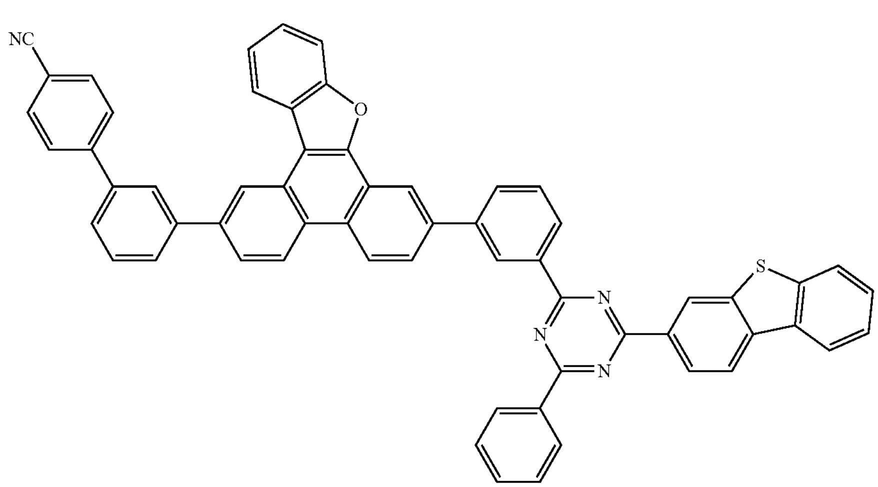

-continued
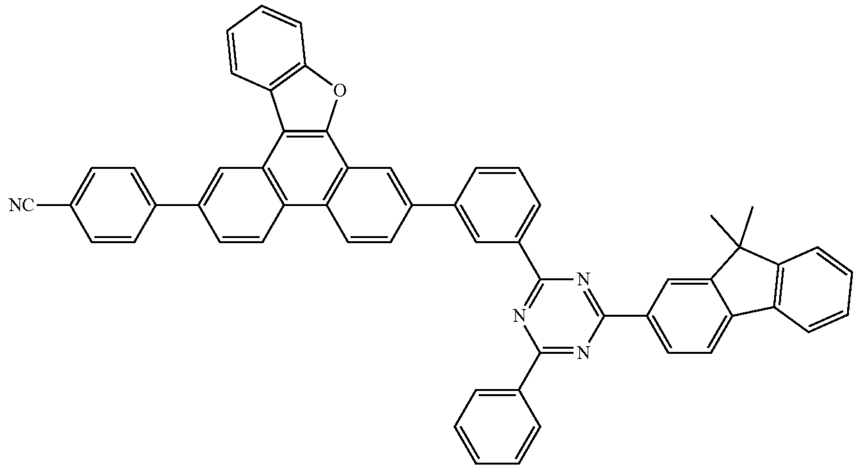
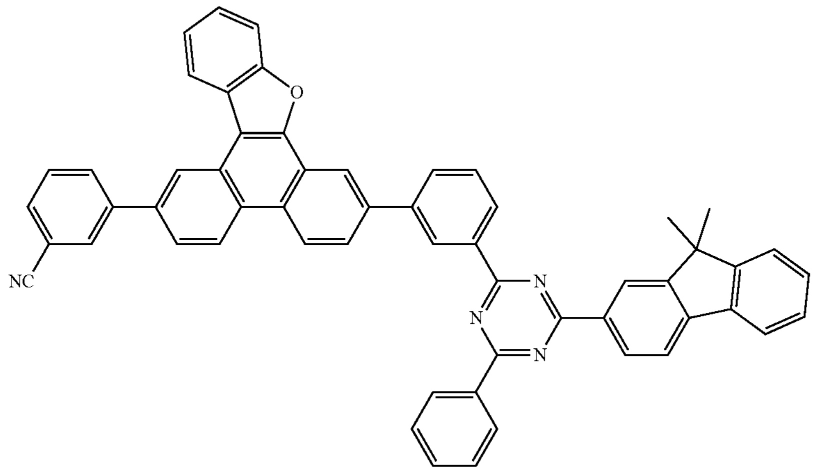
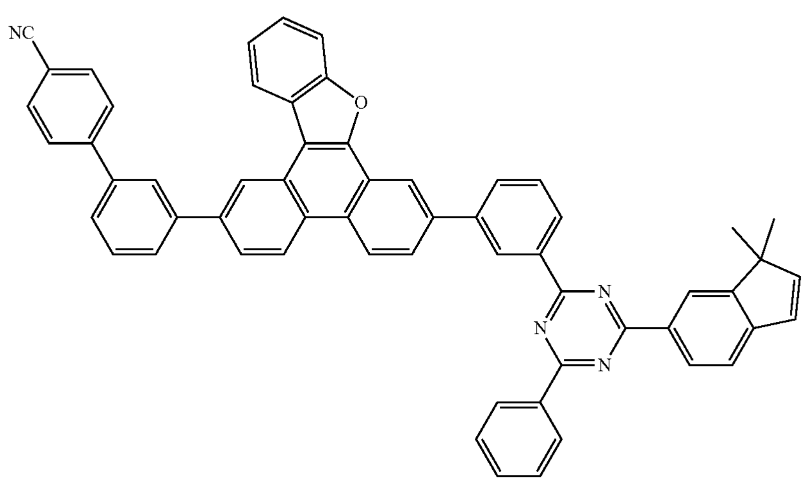

-continued
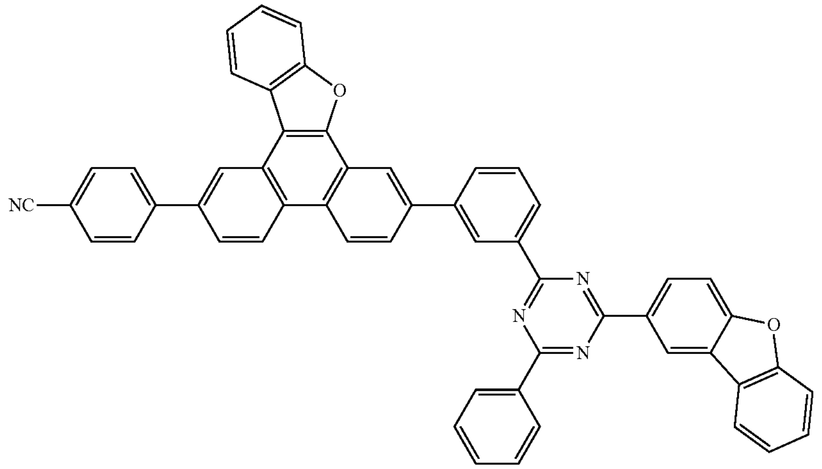
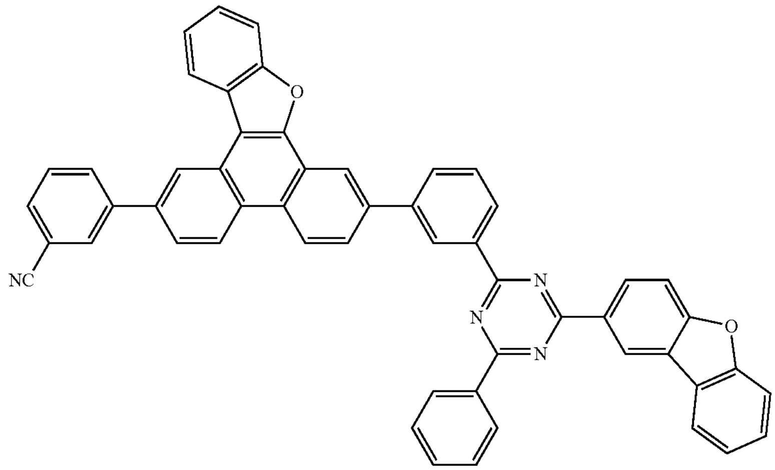
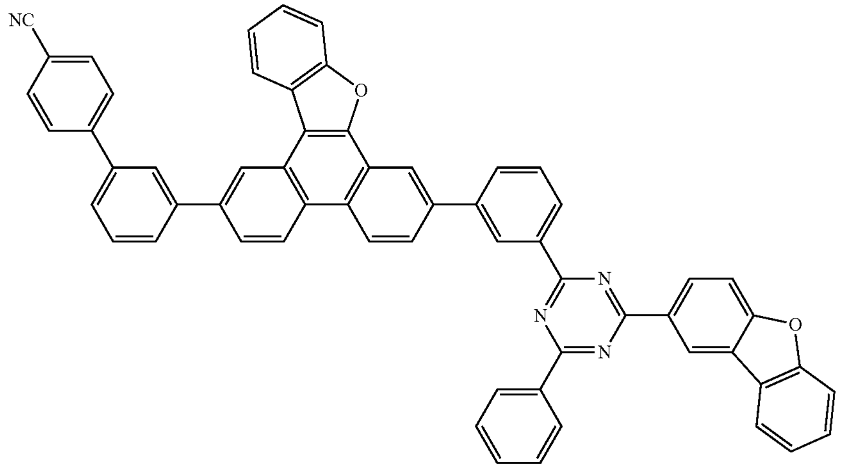

-continued
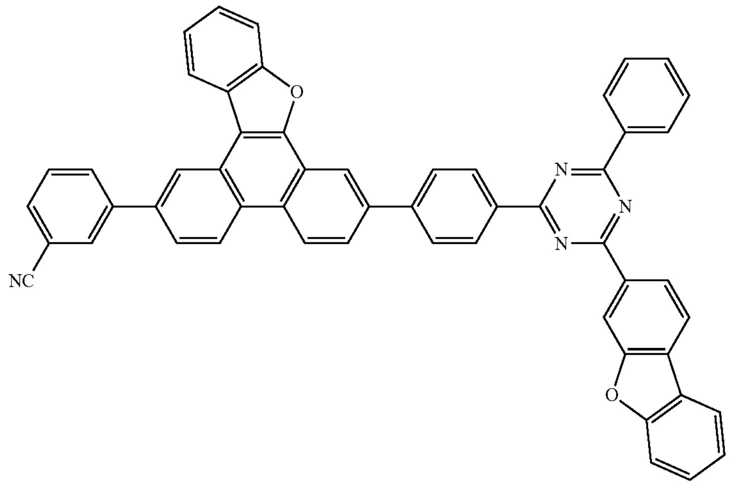
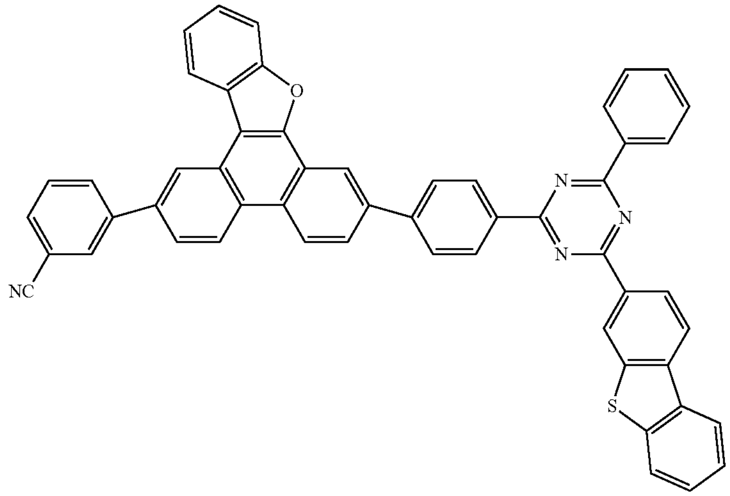
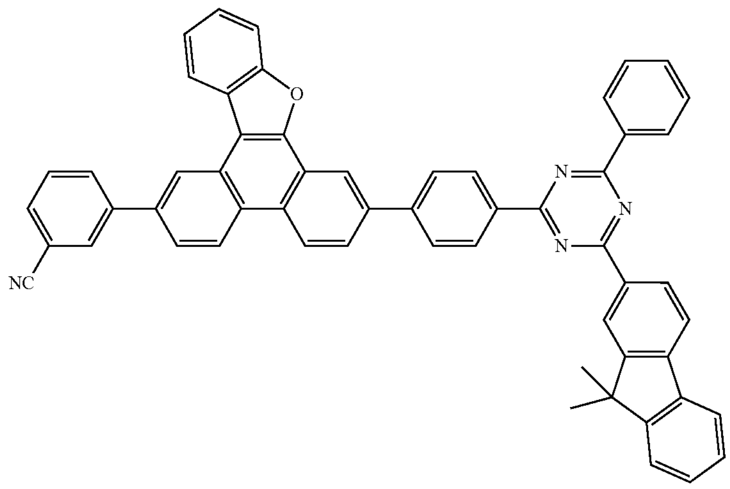

-continued
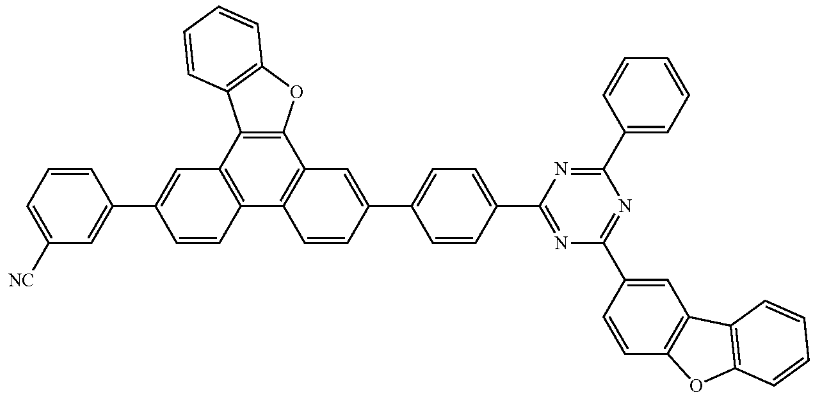
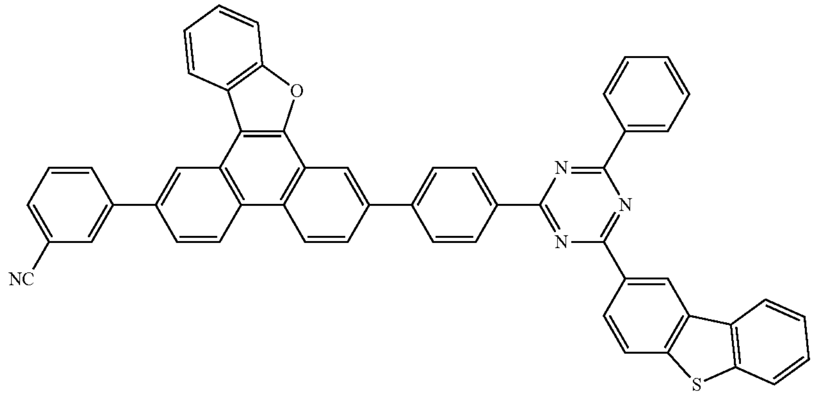
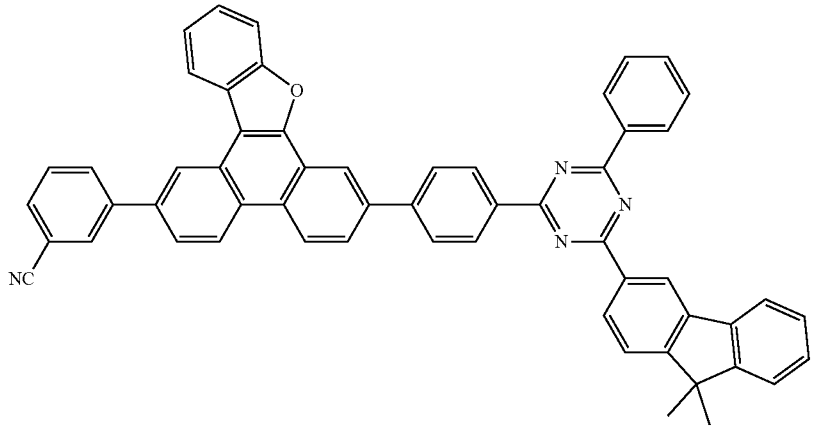
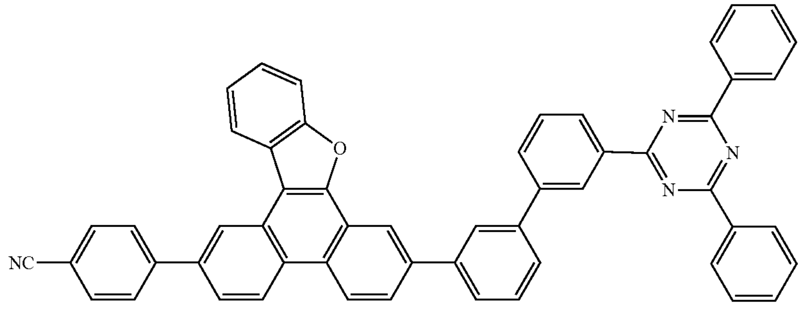

-continued
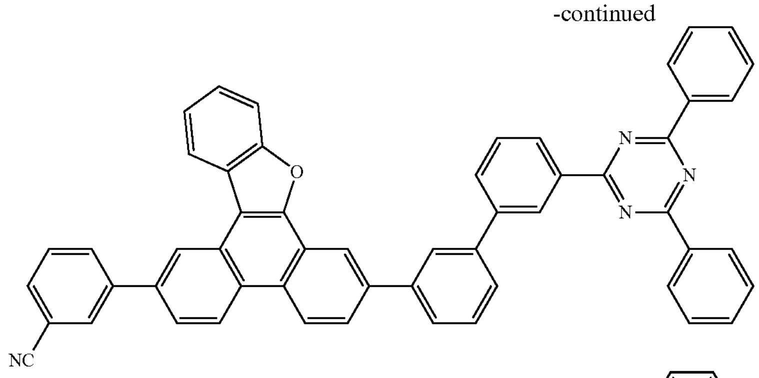
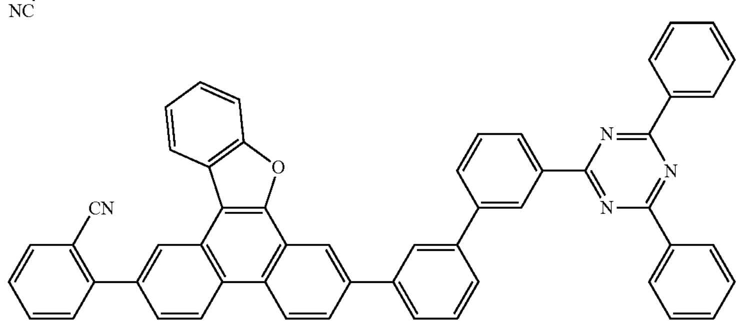
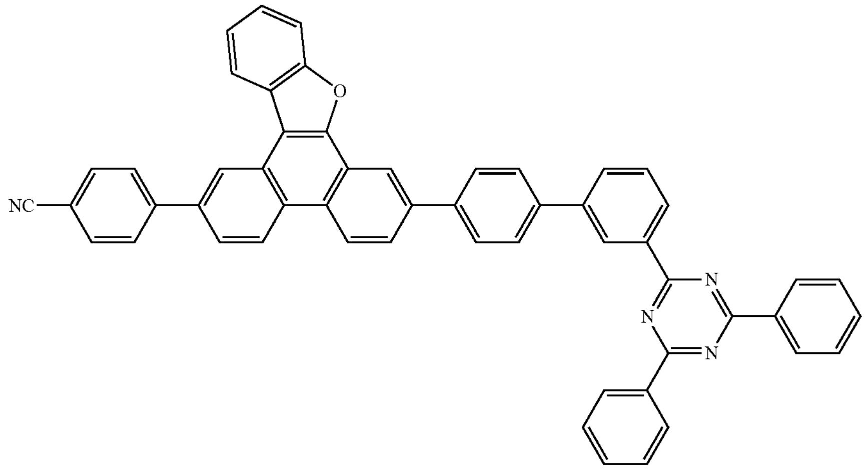
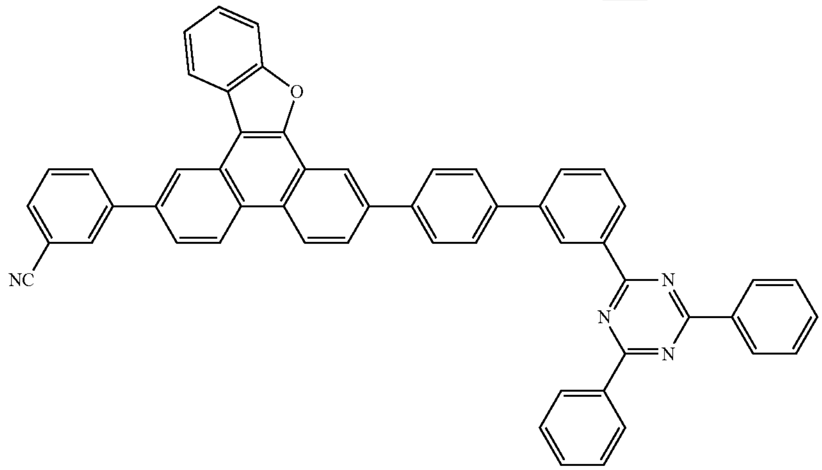

-continued
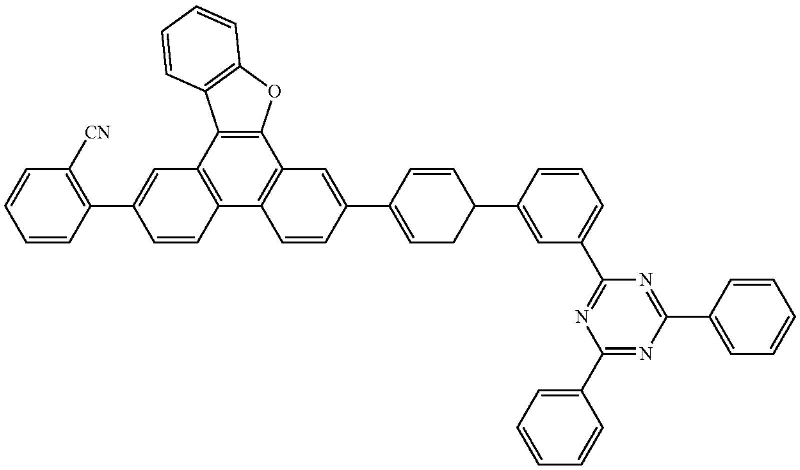
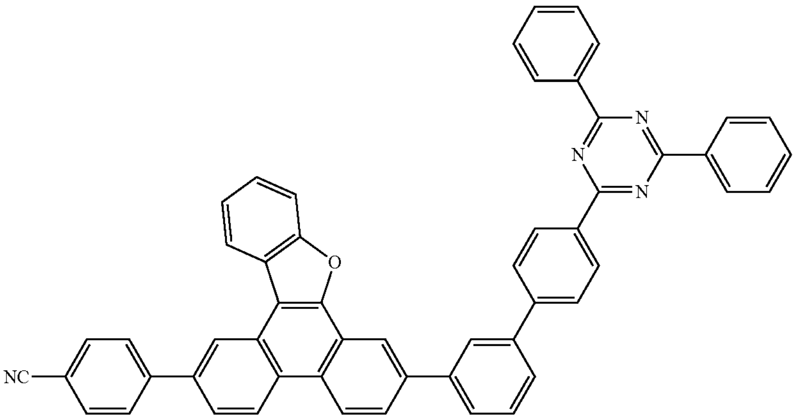
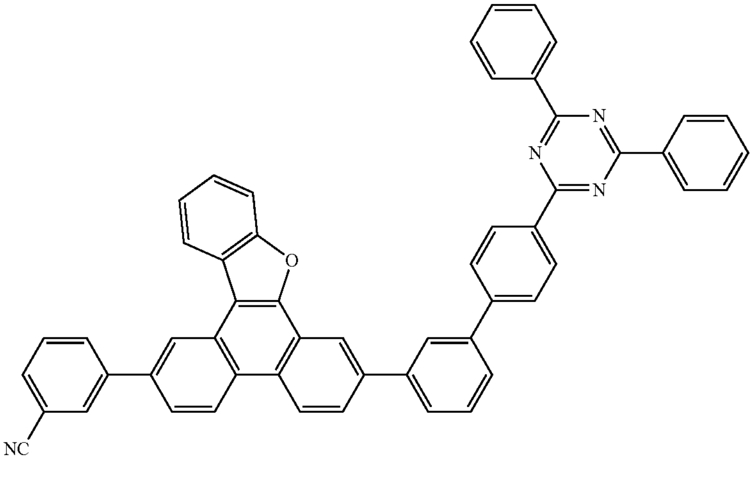

-continued
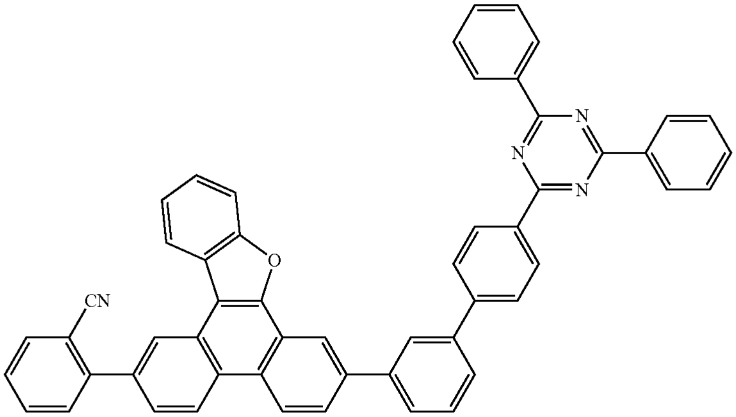
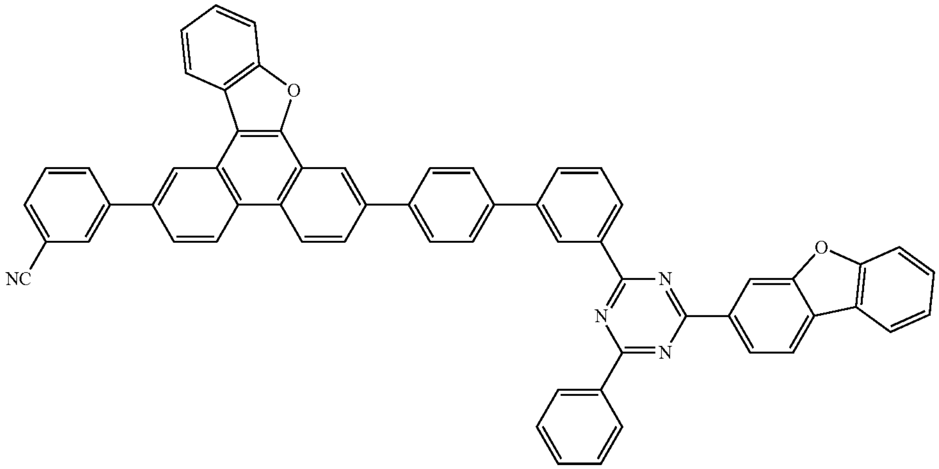
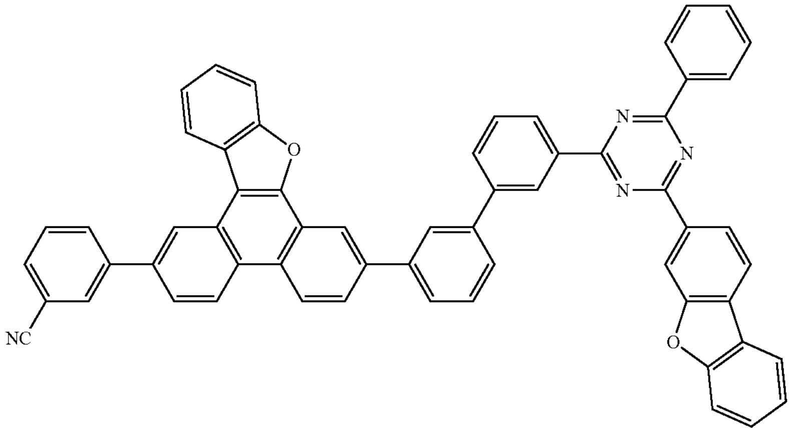

-continued
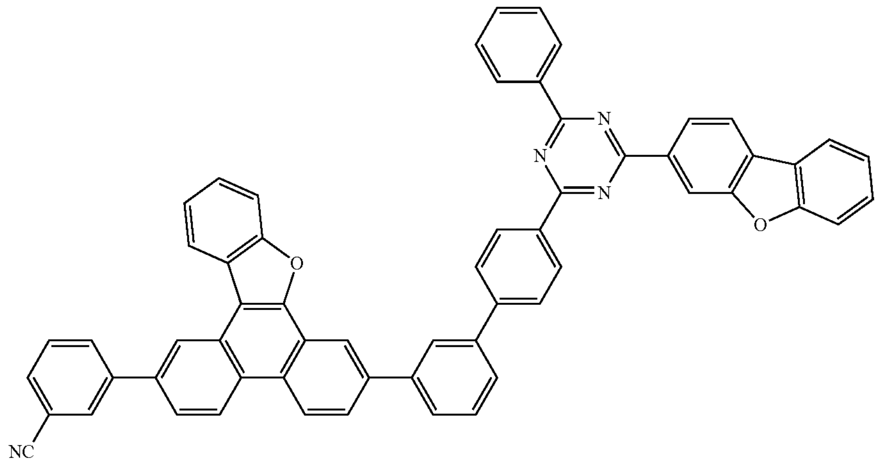
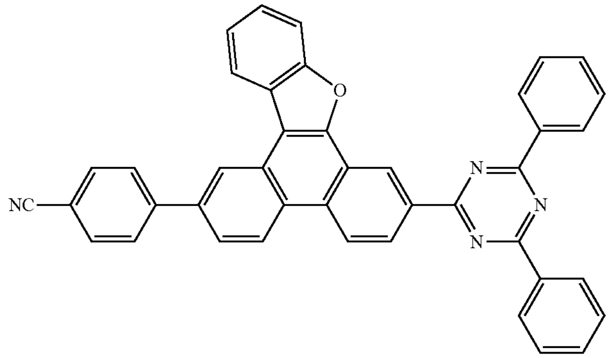
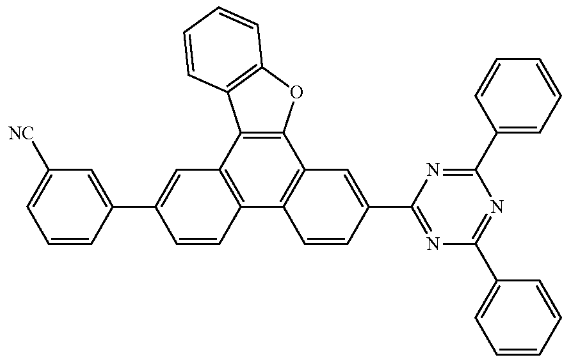
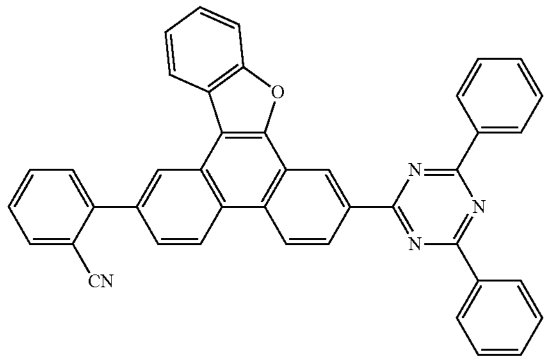
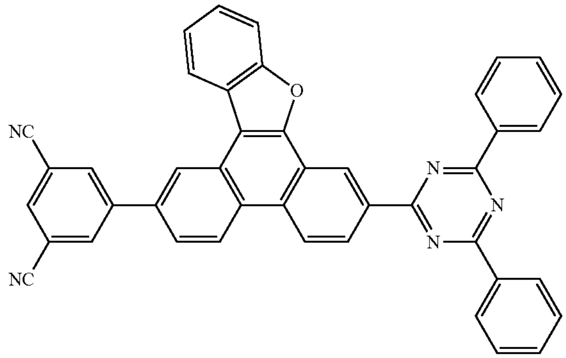

-continued
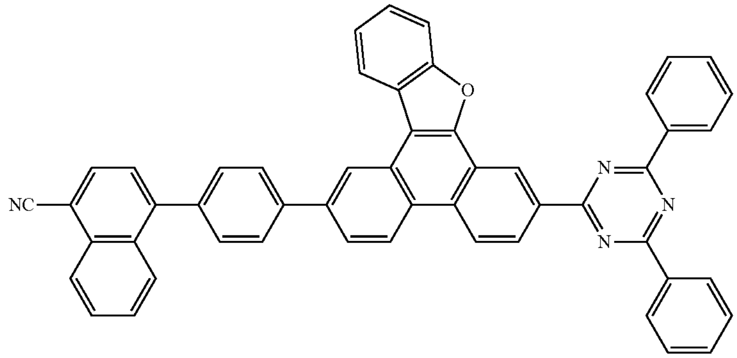
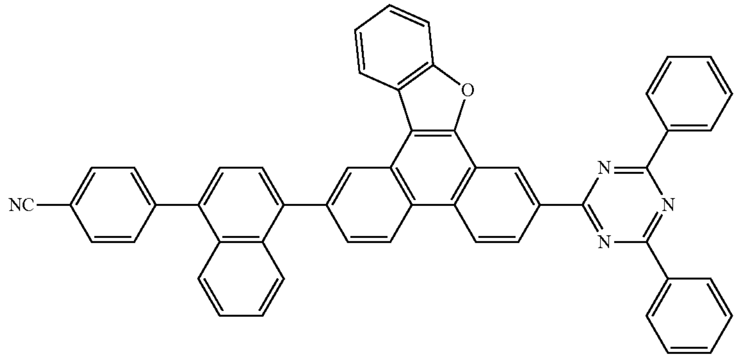
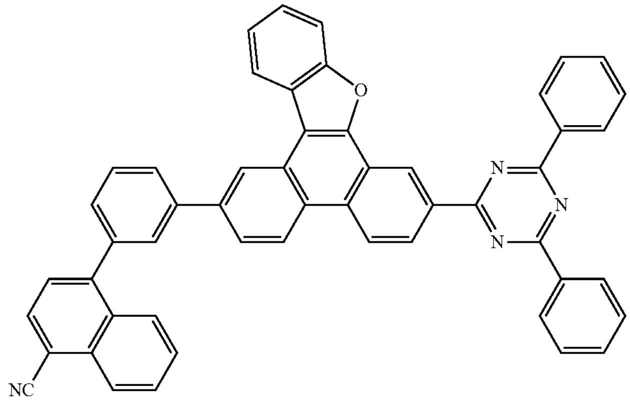
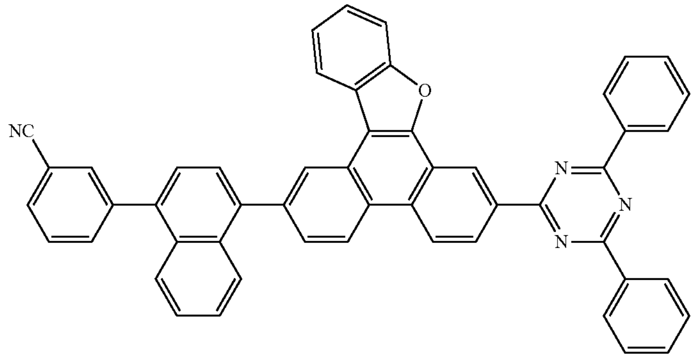

-continued
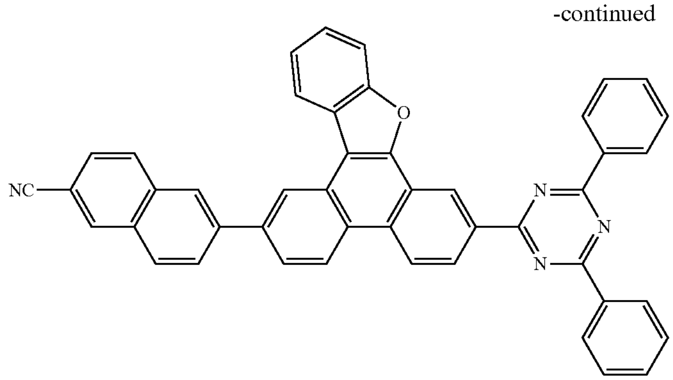
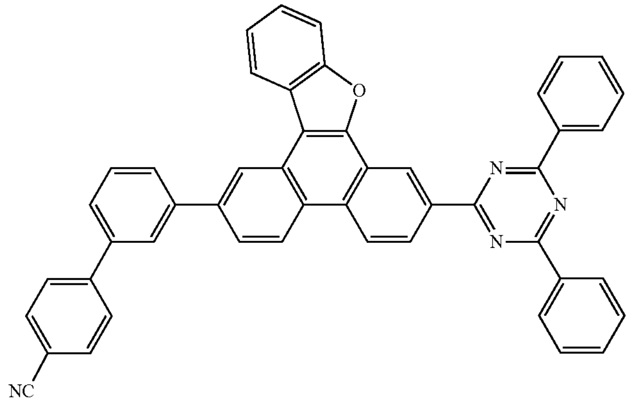
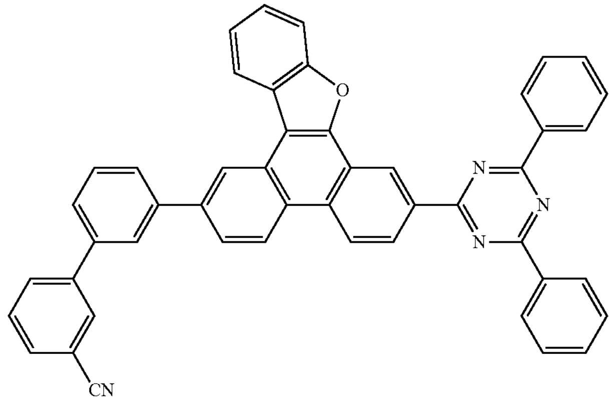
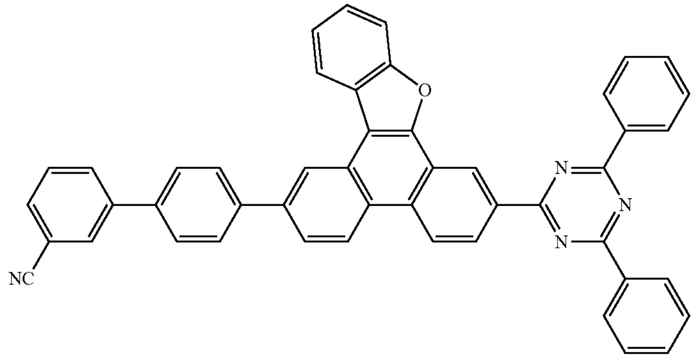

-continued
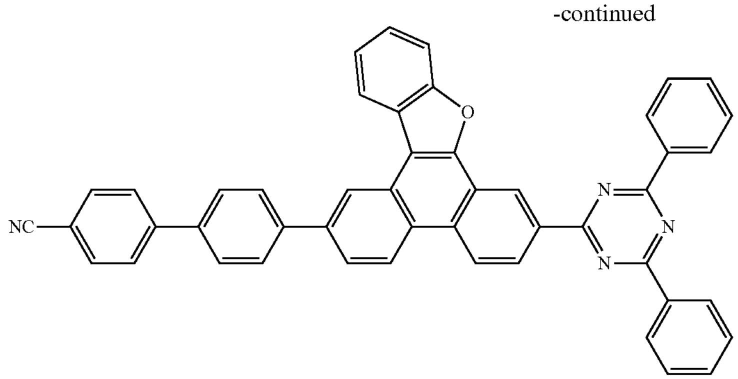
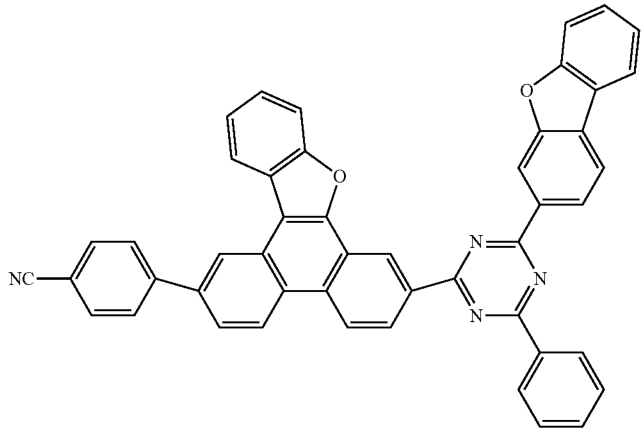
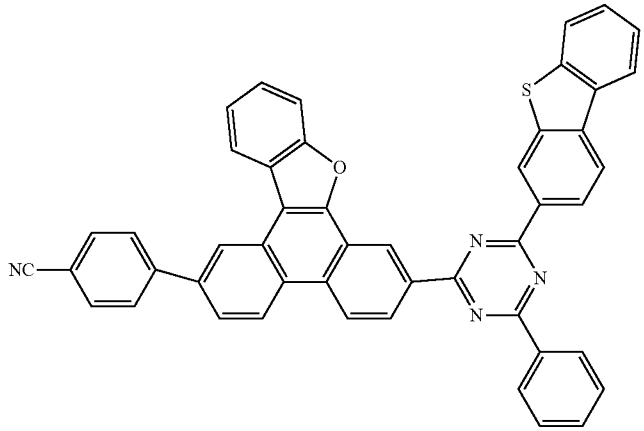
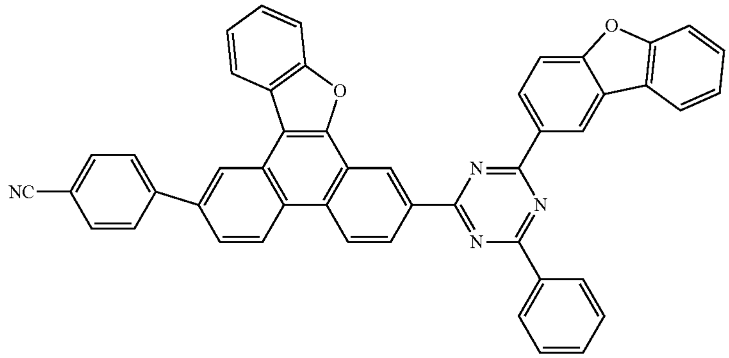

-continued
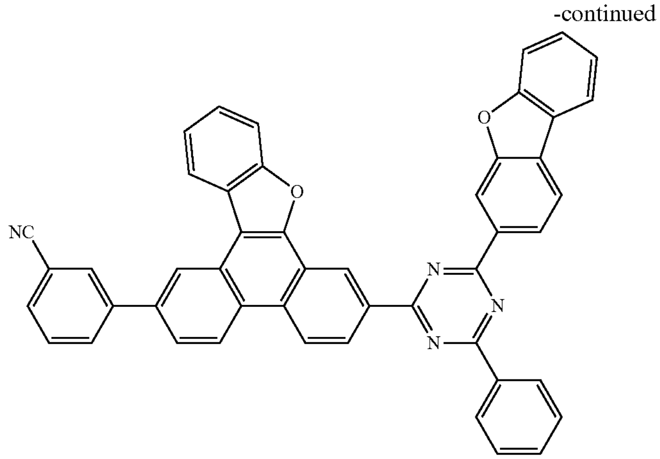
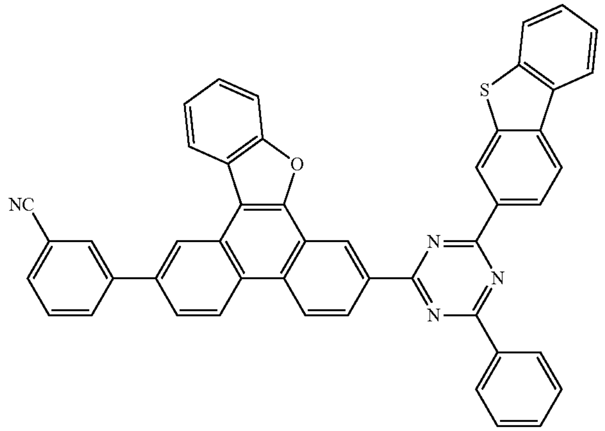
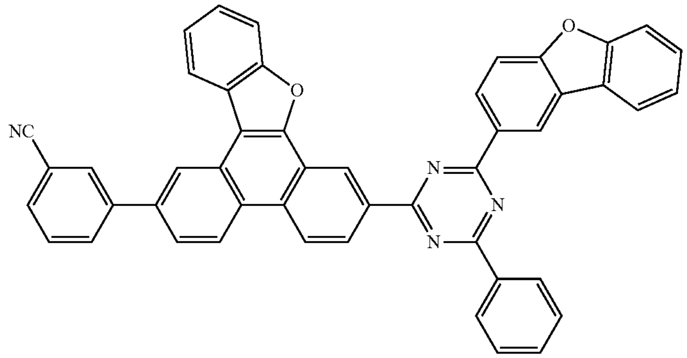
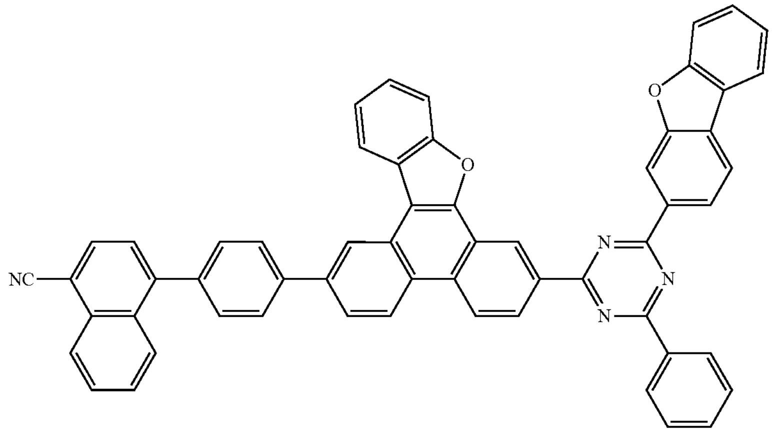

-continued
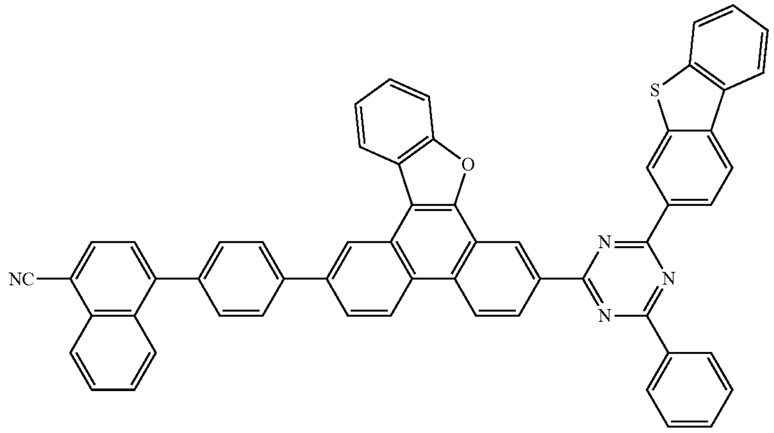
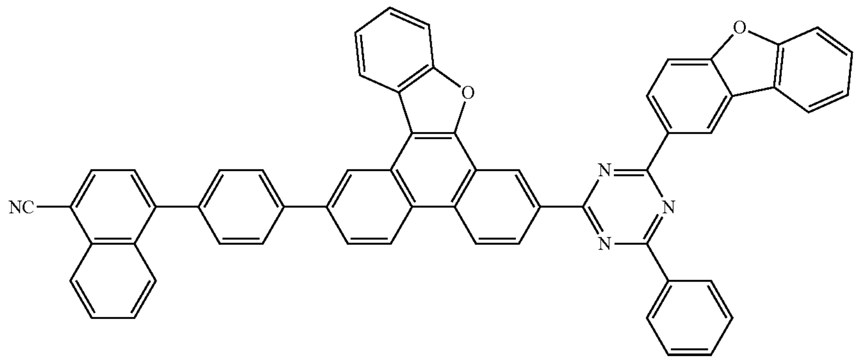
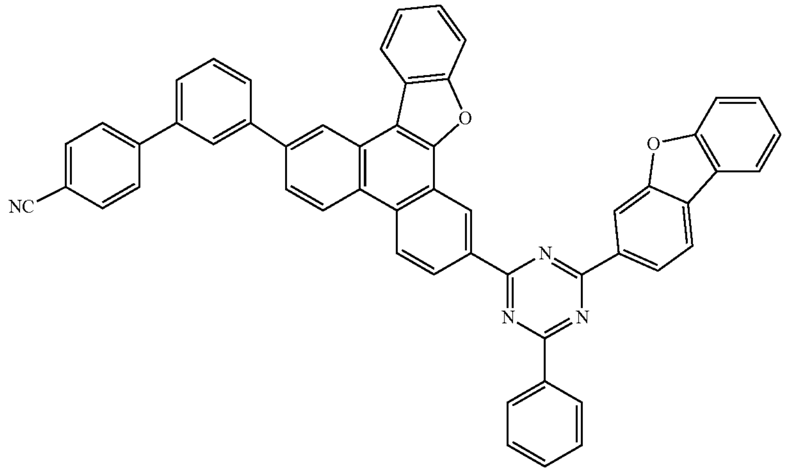

-continued
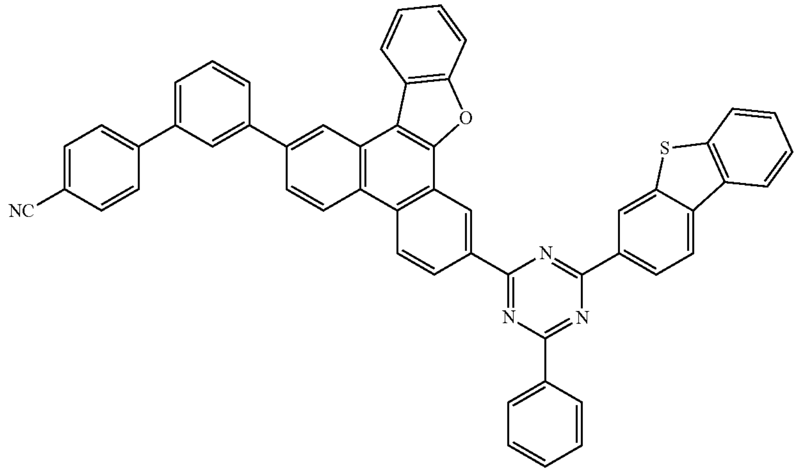
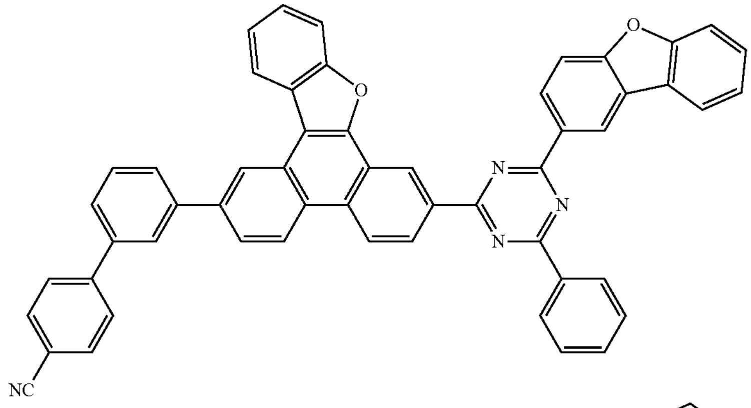
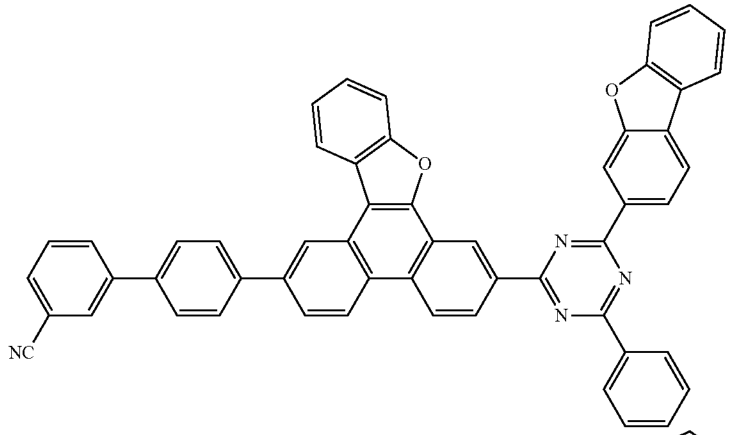
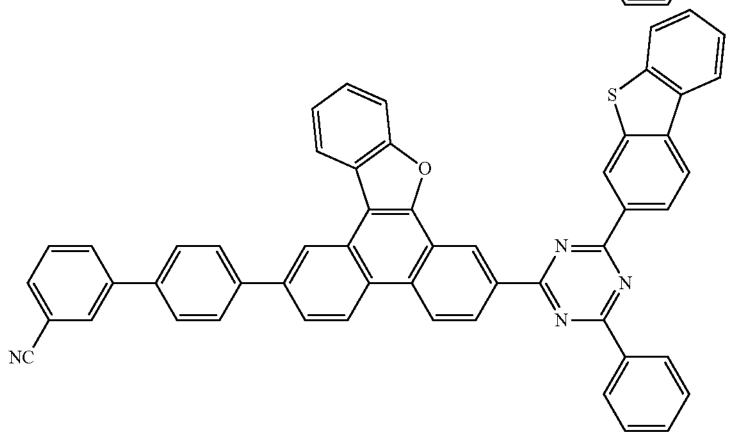

-continued
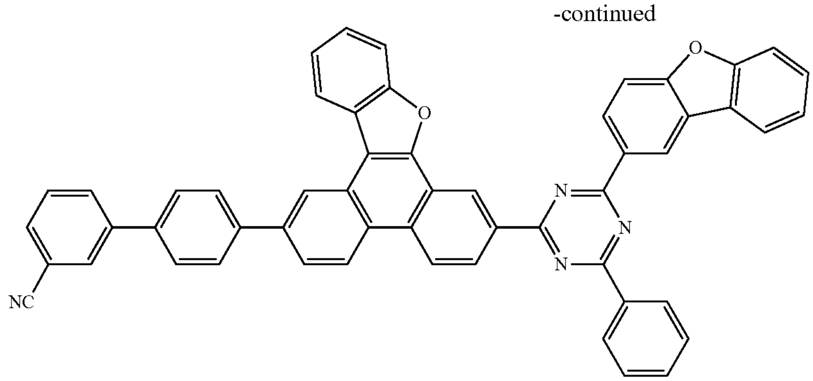
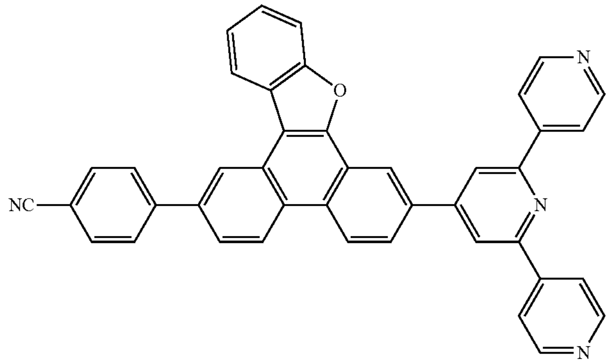
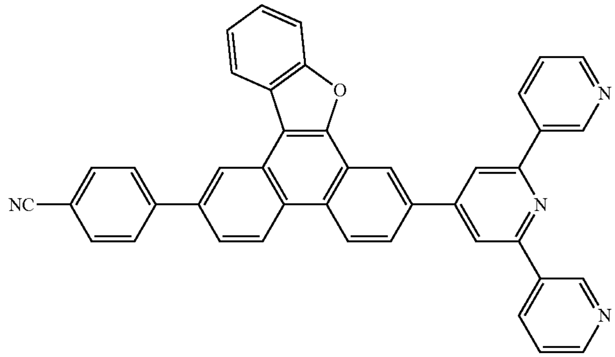
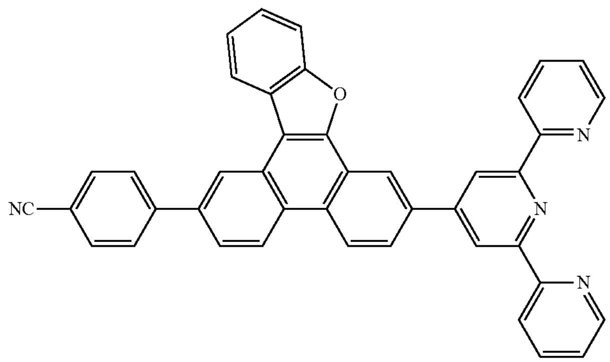
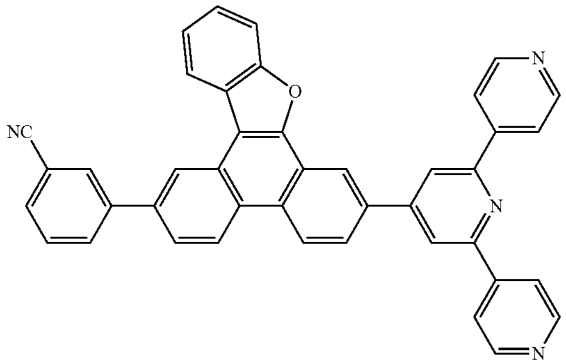

-continued
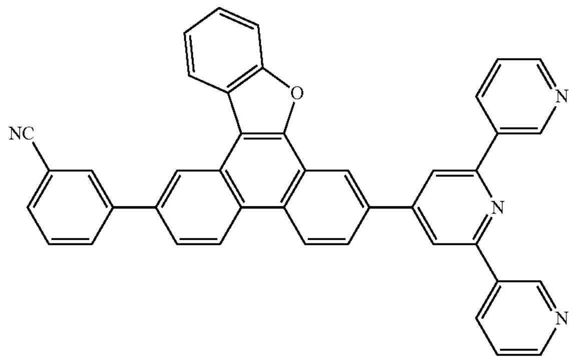
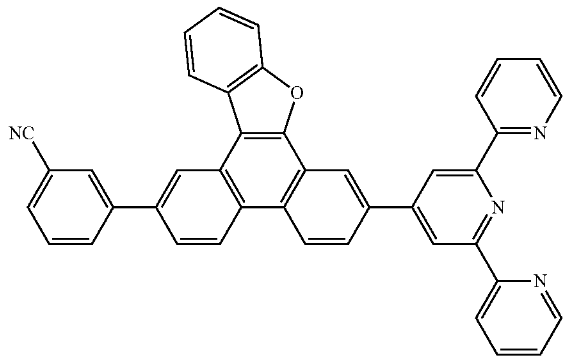
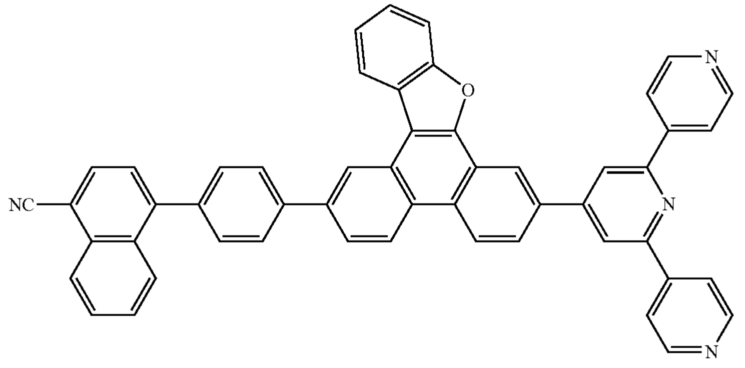
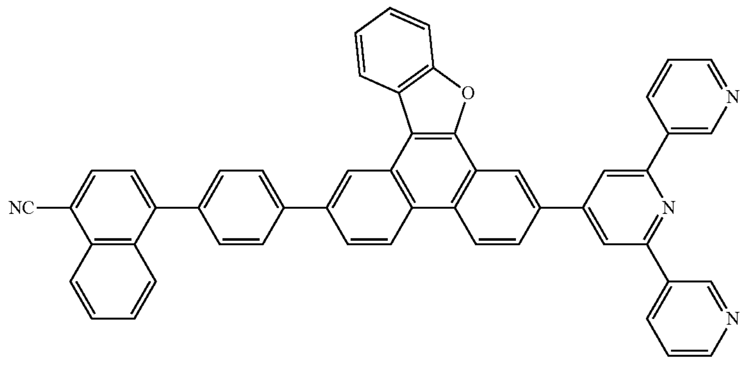
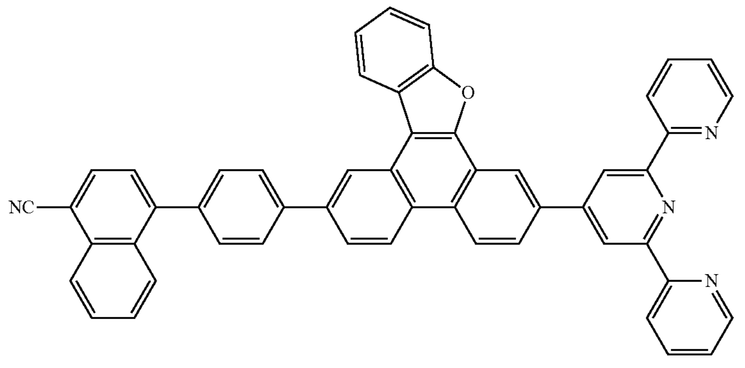

-continued
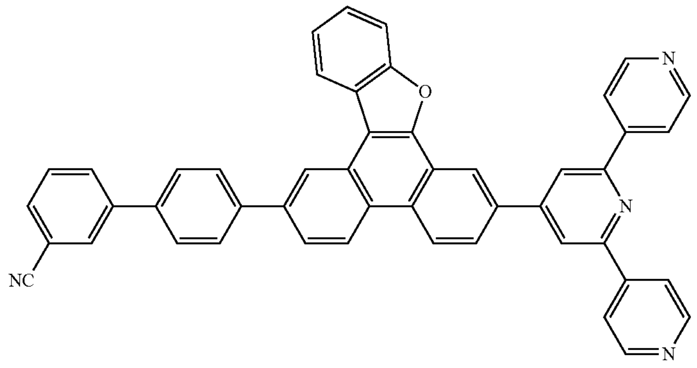
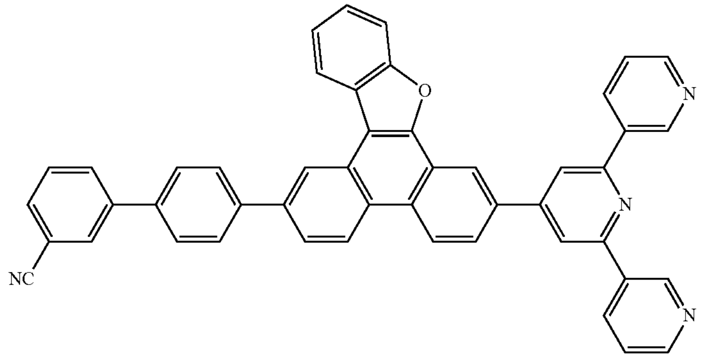
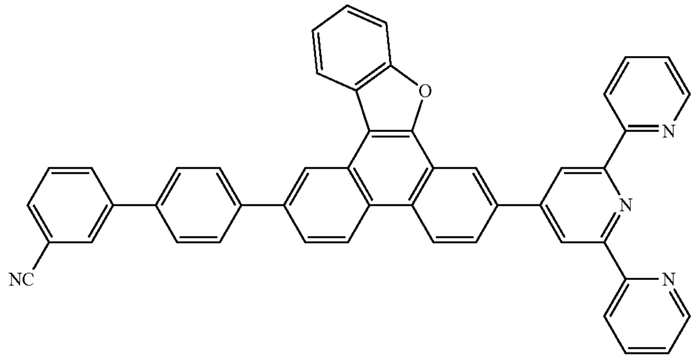
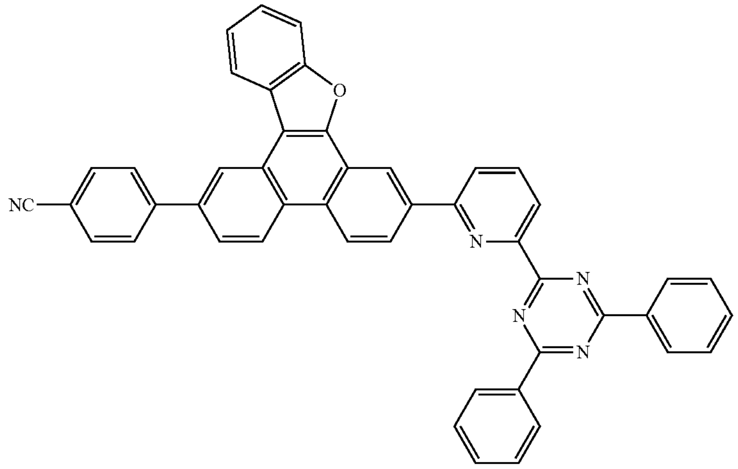

-continued
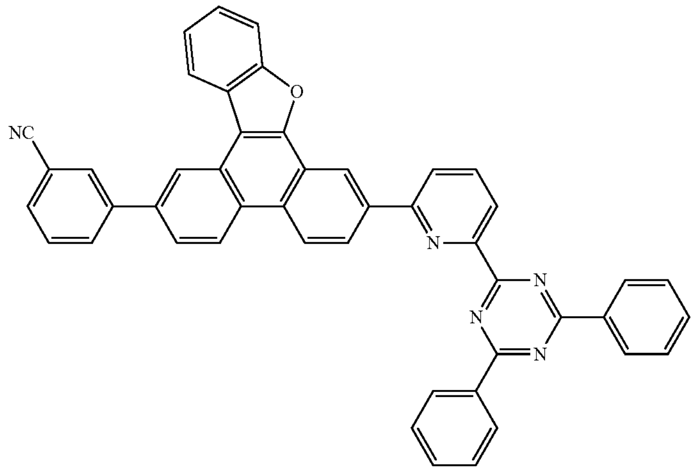
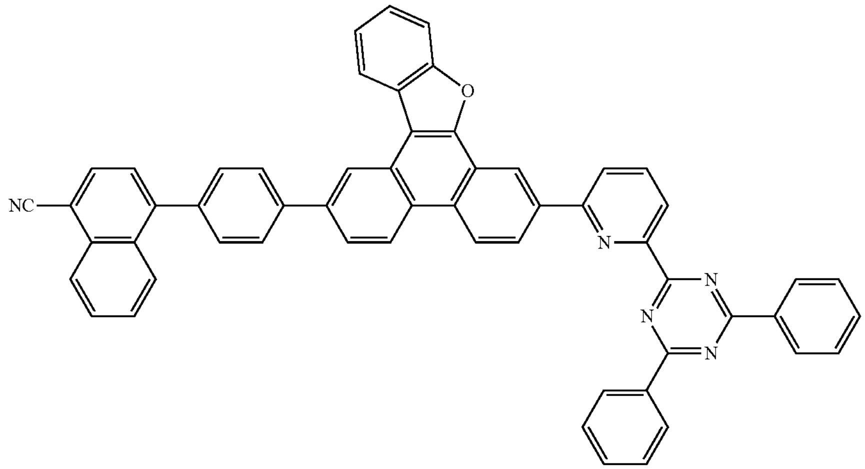
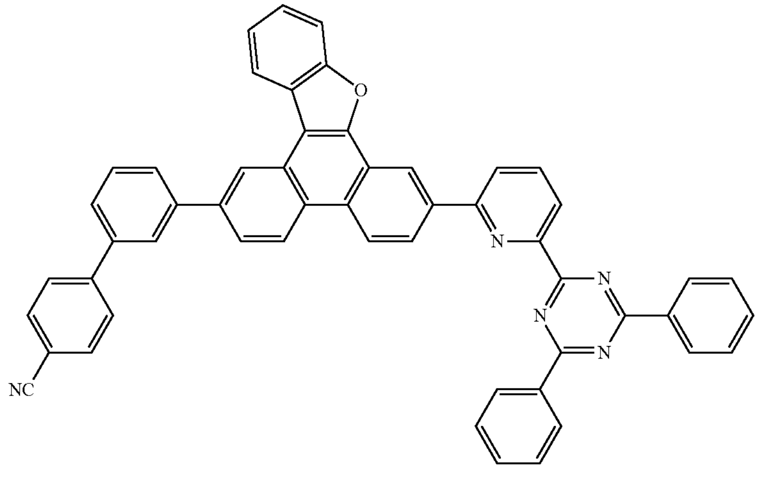

-continued

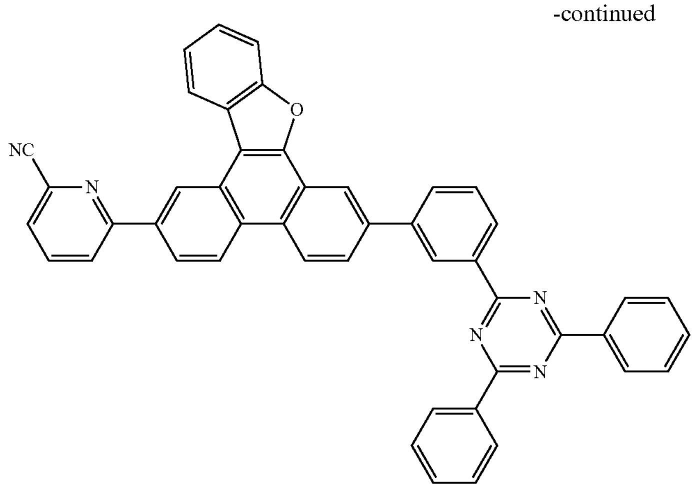

9. An electron transport layer material comprising the organic compound according to claim 1.

10. A hole blocking layer material comprising the organic compound according to claim 1.

11. An organic light-emitting diode (OLED) device, comprising an anode, a cathode and an organic thin film disposed between the anode and the cathode, wherein a material of the organic thin film comprises the organic compound according to claim 1.

12. The OLED device according to claim 11, wherein the organic thin film comprises an electron transport layer, wherein a material of the electron transport layer comprises the organic compound.

13. The OLED device according to claim 12, wherein the organic thin film comprises a hole blocking layer, wherein a material of the hole blocking layer comprises the organic compound.

14. A display panel, comprising the OLED device according to claim 11.

15. An electronic device, comprising the display panel according to claim 14.

* * * * *